(12) United States Patent
Fontayne et al.

(10) Patent No.: US 7,585,307 B2
(45) Date of Patent: Sep. 8, 2009

(54) SURGICAL STAPLING SYSTEM

(75) Inventors: Diego Y. Fontayne, Monroe, NY (US);
John K. Edoga, NorthBeach, NJ (US);
Thierry Richard, Florham Park, NJ (US)

(73) Assignee: Edrich Health Technologies, Inc., Morristown, NJ (US)

( * ) Notice: Subject to any disclaimer, the term of this patent is extended or adjusted under 35 U.S.C. 154(b) by 768 days.

(21) Appl. No.: 11/131,770

(22) Filed: May 17, 2005

(65) Prior Publication Data
US 2005/0283191 A1 Dec. 22, 2005

Related U.S. Application Data

(60) Provisional application No. 60/571,738, filed on May 17, 2004.

(51) Int. Cl.
*A61B 17/08* (2006.01)
(52) U.S. Cl. ...................................................... 606/153
(58) Field of Classification Search ................. 606/153; 227/179.1
See application file for complete search history.

(56) References Cited

U.S. PATENT DOCUMENTS

| | | | | |
|---|---|---|---|---|
| 5,346,115 A * | 9/1994 | Perouse et al. | ........... | 227/179.1 |
| 5,720,755 A * | 2/1998 | Dakov | ......................... | 606/139 |
| 6,248,117 B1 * | 6/2001 | Blatter | ........................ | 606/153 |

* cited by examiner

*Primary Examiner*—(Jackie) Tan-Uyen T. Ho
*Assistant Examiner*—Gregory Anderson
(74) *Attorney, Agent, or Firm*—Wiggin and Dana LLP; Anthony P. Gangemi

(57) ABSTRACT

A system is provided for joining two tubular structures by a surgical stapling procedure. The system includes a series of sizers, a specifically designed graft, a loading unit, a wand, a tourniquet, and a stapling instrument. The sizers are for determining the diameter of a target aorta and the availability of a sufficient transected aortic length to perform a stapling procedure. The loading unit holds the graft in position in the body and deploys a circumferential line of staples through the graft and an overlapping end of the aorta. The graft includes a side port by which the loading unit holds the graft during the stapling procedure, and which may be closed once the stapling procedure has been completed. The wand may be used to introduce the loading unit and graft into the body, to position them within the transected aorta, and to hold them in place during the application of the tourniquet. The tourniquet includes a band formed from a flexible material and having a width greater than its thickness so as to facilitate the formation of an annular loop. With the tourniquet holding the aorta and graft in relative overlapping positions, the wand may be removed from the loading unit and the stapling instrument includes a plurality of anvils, which may be closed to form a circle overlying the aorta, and a trigger mechanism for firing the staples. When fired, the staples are deployed radially outward through the graft and aorta, whereupon their free ends are bent inwardly by staple returns on the anvils. As a result, a plurality of staples may be simultaneously deployed quickly and accurately in a circumferential pattern so as to join together two tubular structures. The system may be used in either an open surgical procedure or laparascopically.

14 Claims, 44 Drawing Sheets

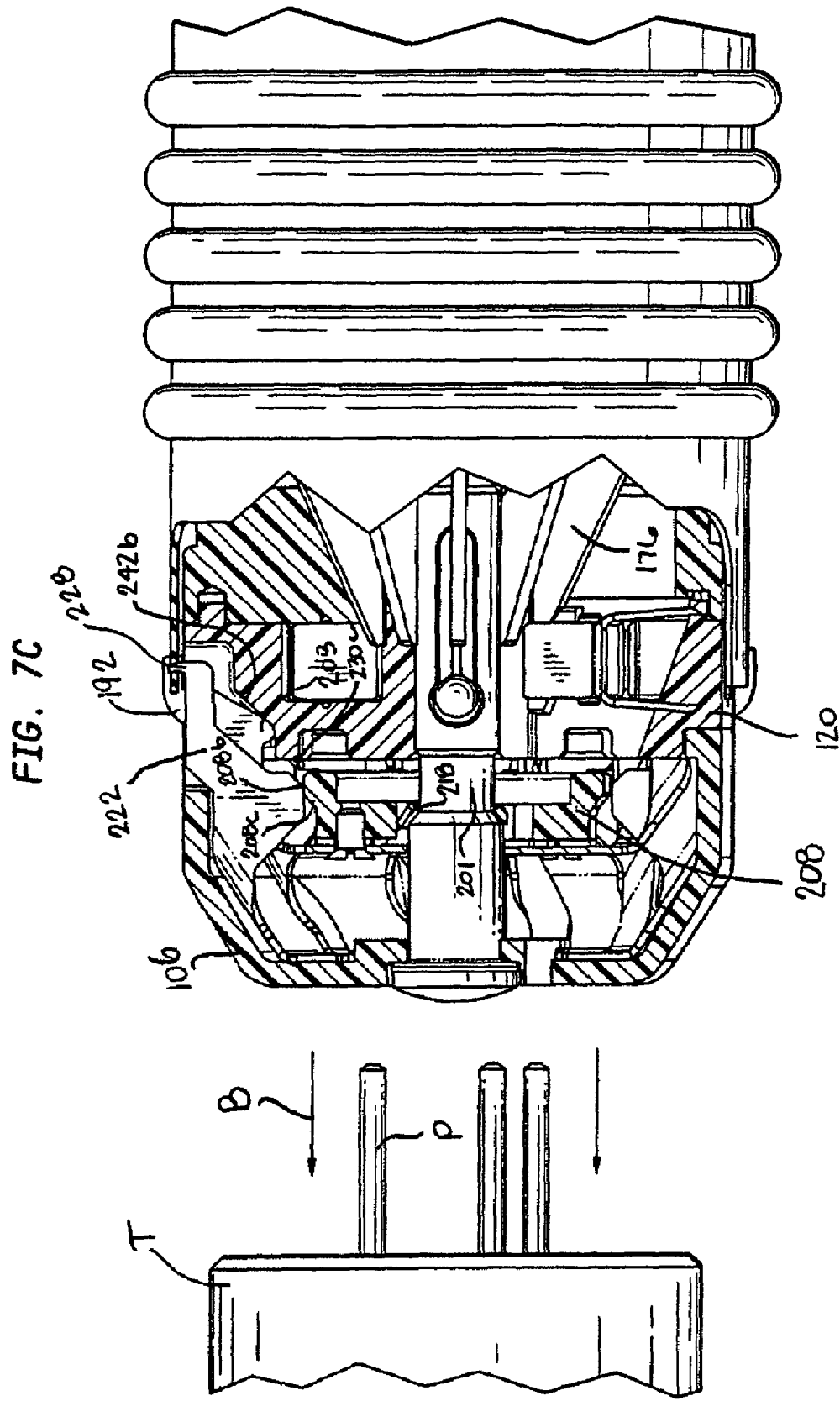

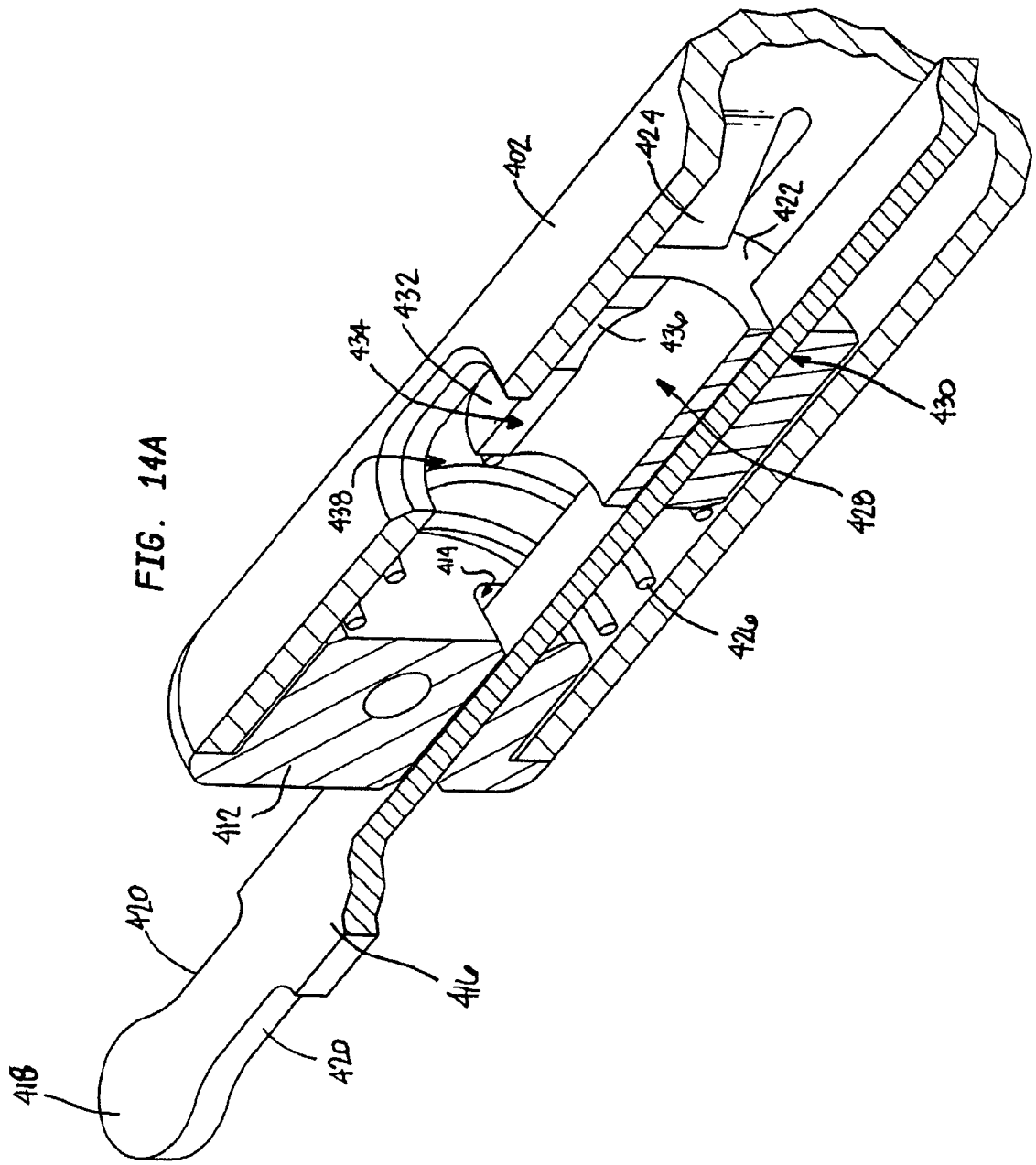

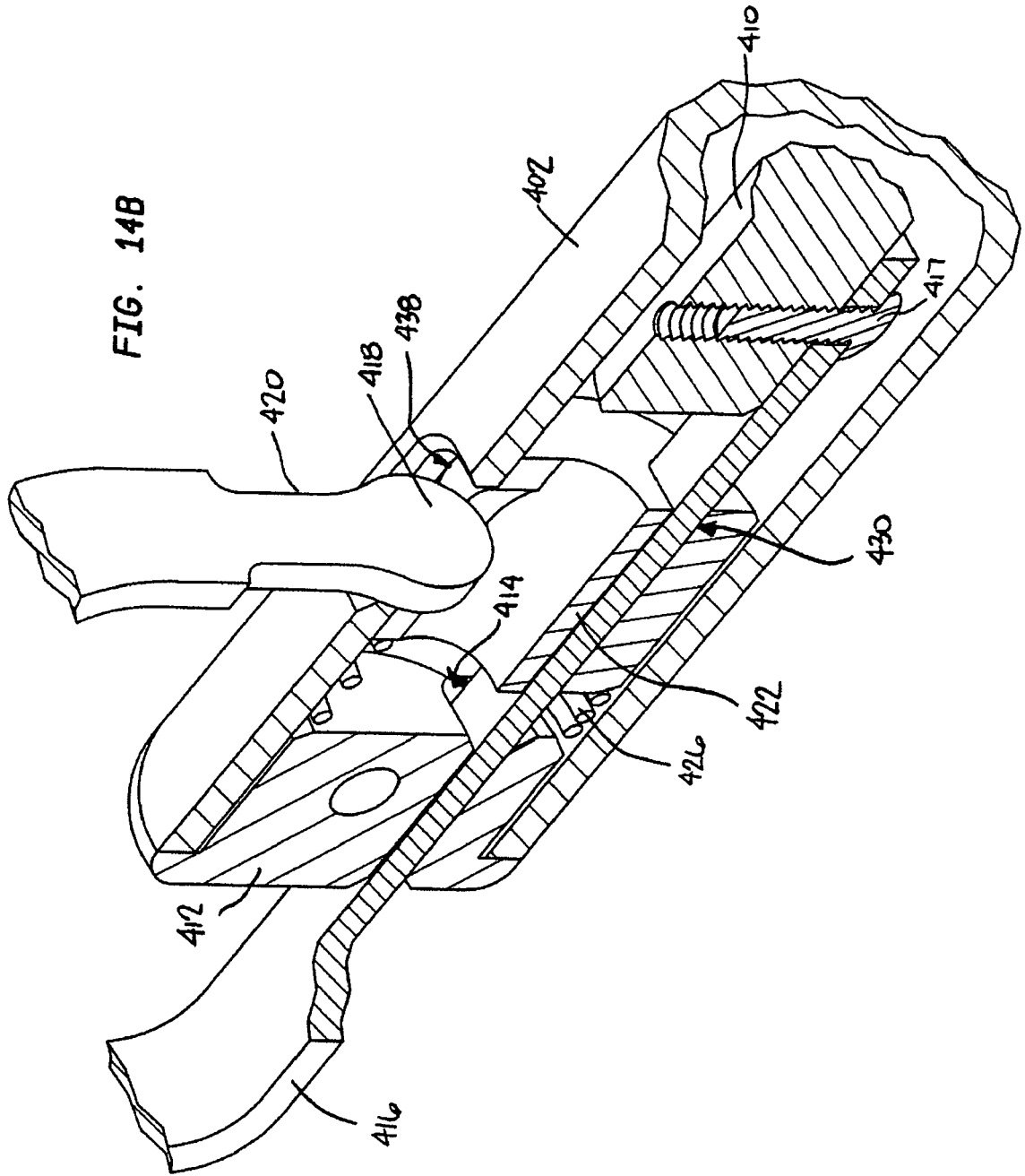

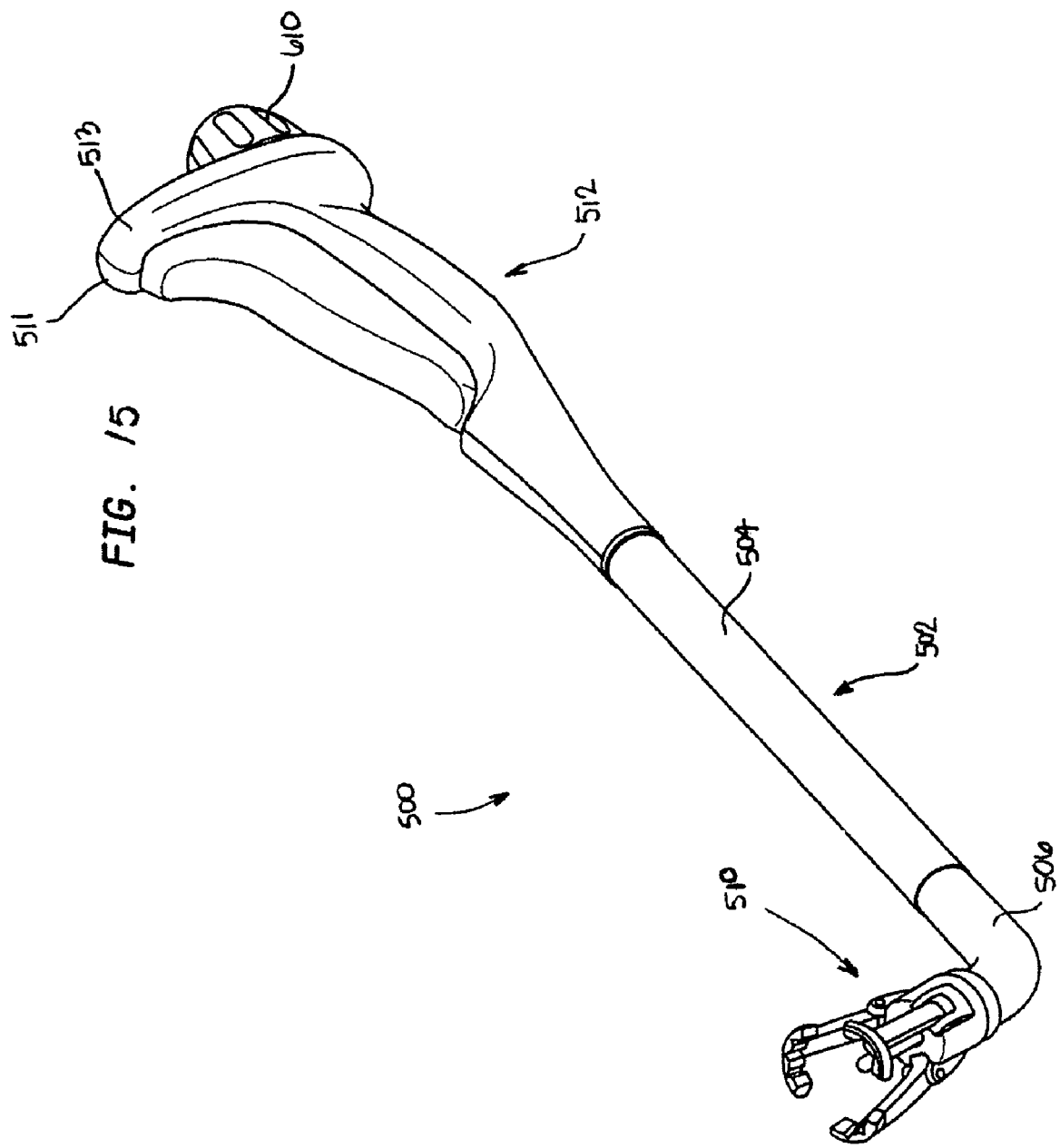

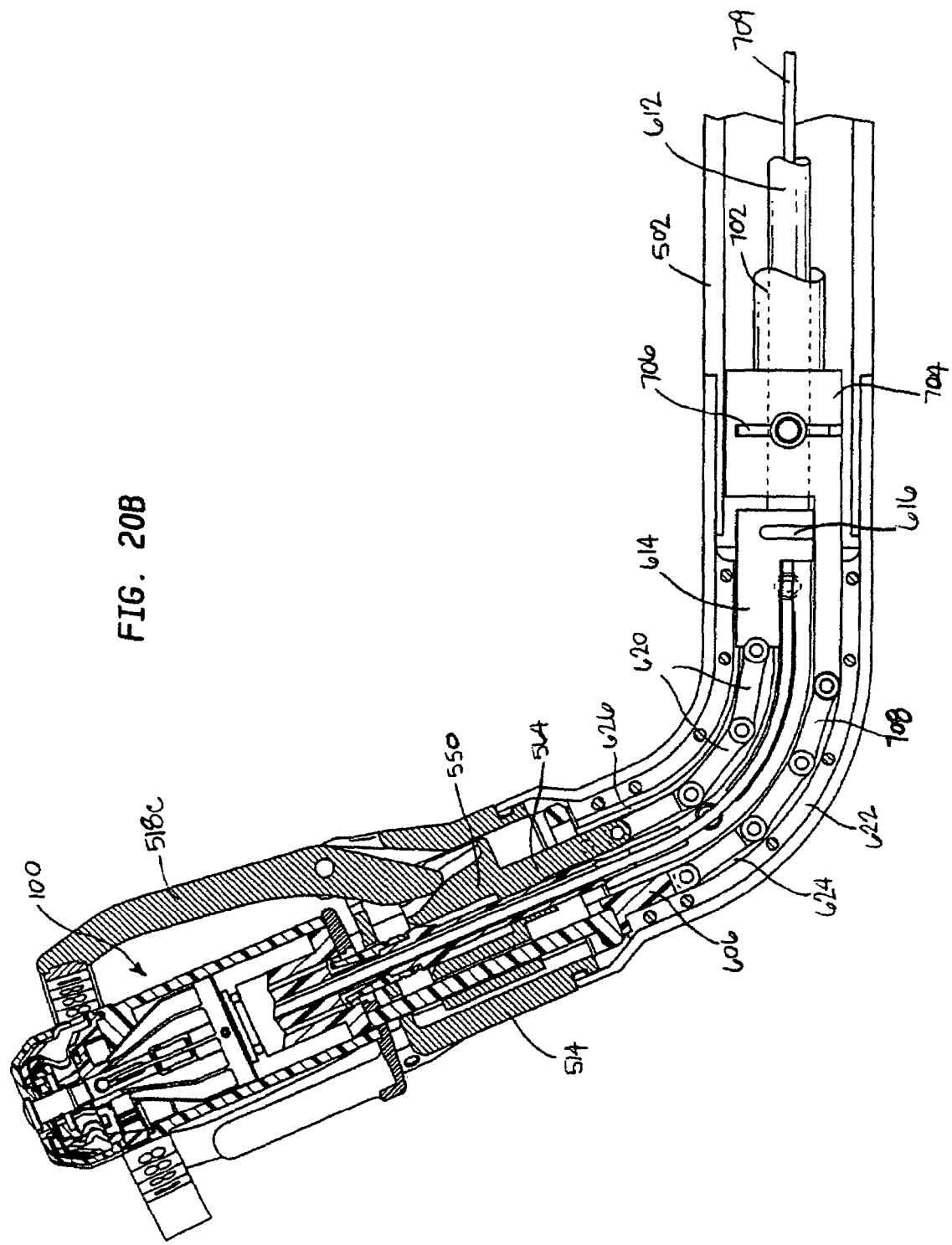

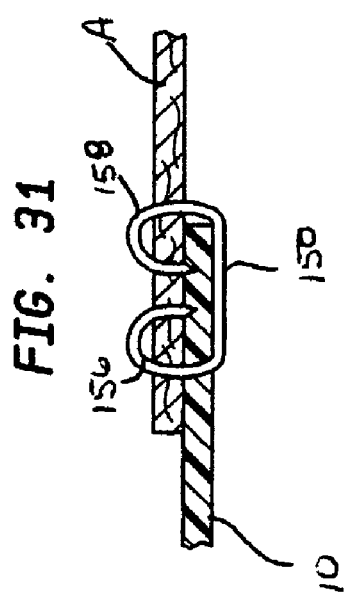
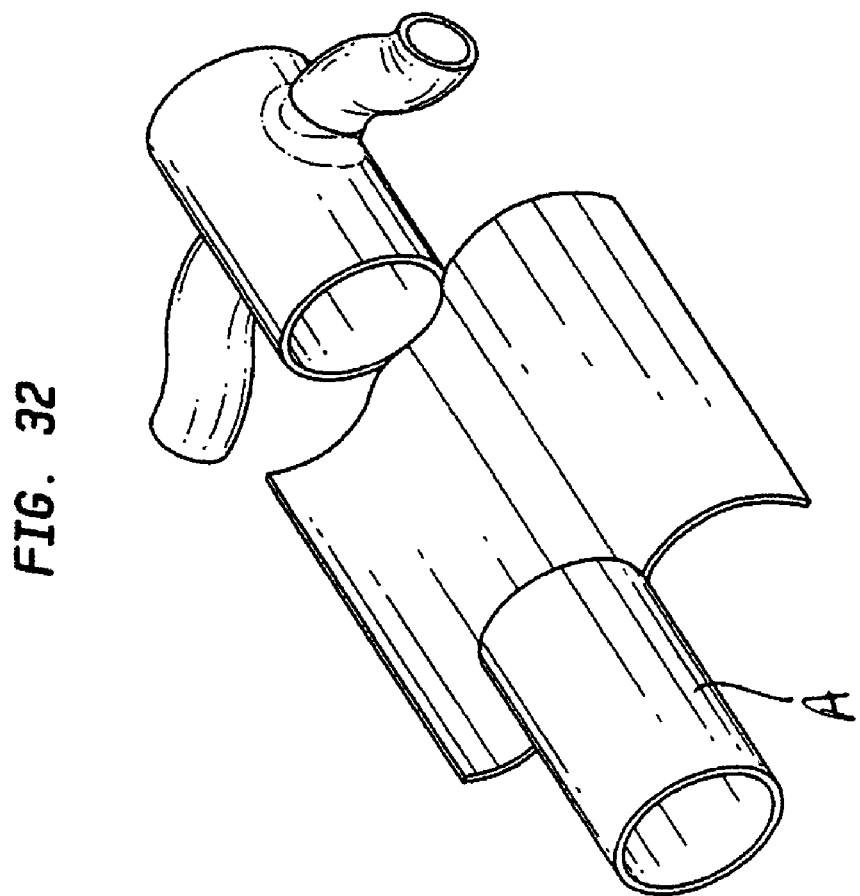

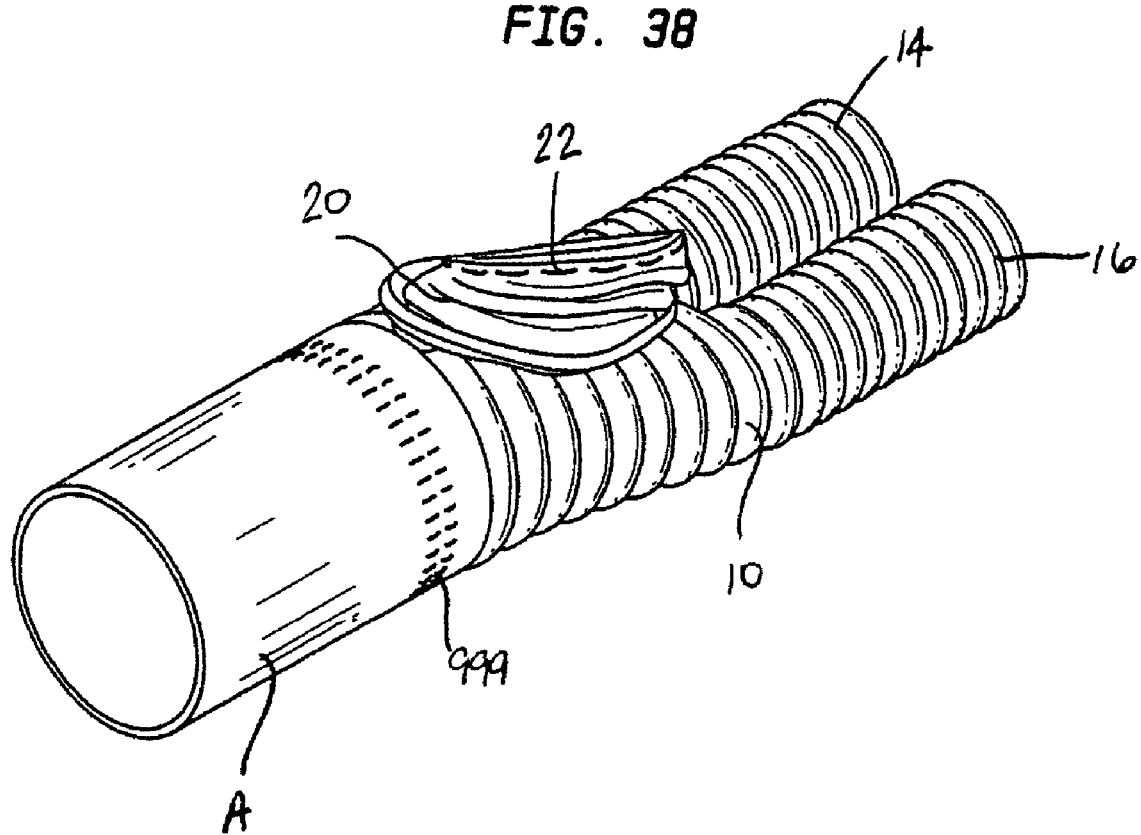

SURGICAL STAPLING SYSTEM

CROSS-REFERENCE TO RELATED APPLICATIONS

The present application claims the benefit of U.S. Provisional Patent Application Ser. No. 60/571,738 filed May 17, 2004, the disclosure of which is hereby incorporated by reference herein.

BACKGROUND OF THE INVENTION

The present invention relates generally to a surgical stapling system, and more particularly to a system for joining two tubular structures using surgical staples. Still more particularly, the present invention relates to an apparatus and method for stapling together two tubular structures either through an open surgical procedure or laparoscopically.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 7C is the same view as FIG. 7A, but showing the loading unit with a graft loaded thereon;

FIG. 14A is a cross-sectional perspective view of the distal end of the tourniquet of FIG. 13 showing the band in an unlocked condition;

FIG. 14B is the same view as FIG. 14A, but showing the band being inserted into the retaining block;

FIG. 15 is a perspective view of a surgical stapling instrument of the present invention;

FIG. 20B is a longitudinal cross-sectional view of the head of the surgical stapling instrument having a loading unit mounted thereon, with the anvils of the surgical stapling instrument in the open condition;

FIG. 31 is a partial cross-sectional view showing a deployed staple joining a graft to an aorta;

FIG. 32 is a highly schematic perspective view showing a transected aorta;

FIG. 38 is a highly schematic perspective view showing a circumferential line of staples joining the graft to the aorta.

DETAILED DESCRIPTION

In the detailed description that follows, the features of the present invention will be described in connection with the anastomosis of a prosthetic graft to the aorta, such as may be performed in the repair of an abdominal aortic aneurysm. It will be appreciated, however, that the various features of the present invention may be readily utilized to connect a tubular prosthetic graft to any body lumen. Each of the various components of the surgical stapling system of the present invention is described in separate headings below.

Prosthetic Graft

Figure 1:
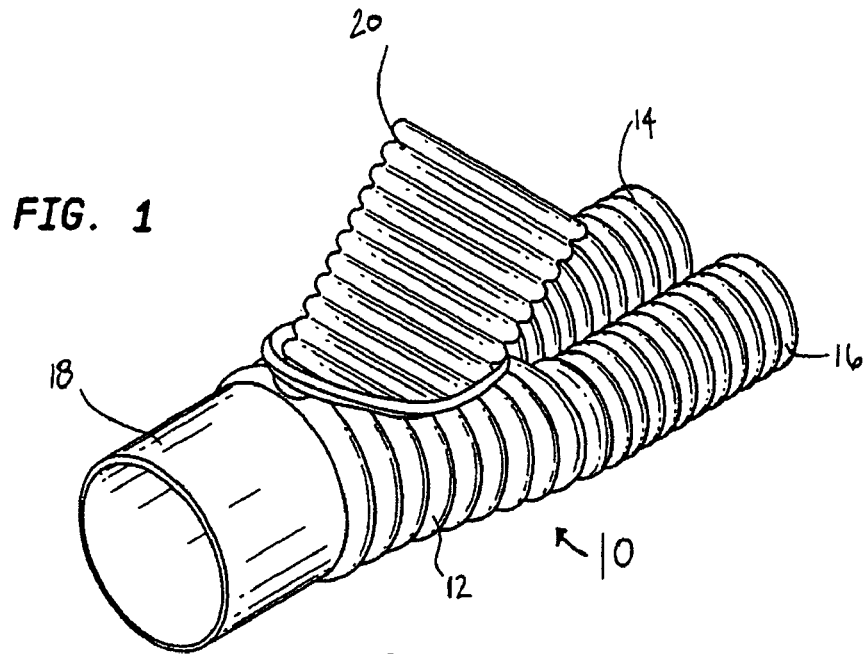
FIG. 1 is a perspective view of a first embodiment of prosthetic graft for use with the surgical stapling system of the present invention.

Referring to FIG. 1, there is illustrated one preferred embodiment of a prosthetic graft 10 for use in the present invention. Graft 10 is a hollow generally Y-shaped structure formed by a tapered main body 12, which branches into two legs 14 and 16. Legs 14 and 16 may have a generally cylindrical shape with a substantially uniform diameter from their juncture with main body 12 to their respective free ends. Opposite legs 14 and 16, main body 12 includes a cuff 18 having a substantially uniform diameter, the free end of which defines a blood flow inlet on one end of graft 10, while the free ends of legs 14 and 16 define blood flow outlets from graft 10.

Figure 2:
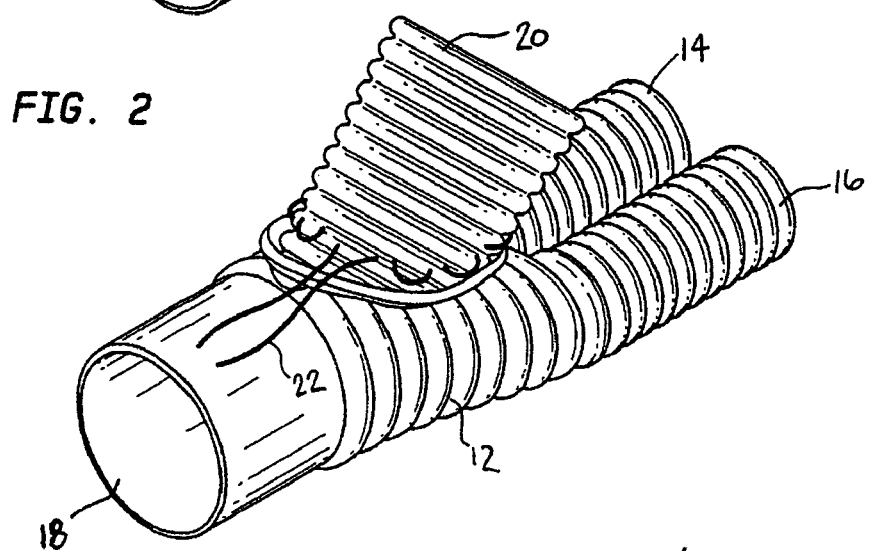
FIG. 2 is a perspective view of the prosthetic graft of FIG. 1 having optional sutures for closing the side port following deployment of the graft.
Figure 4:
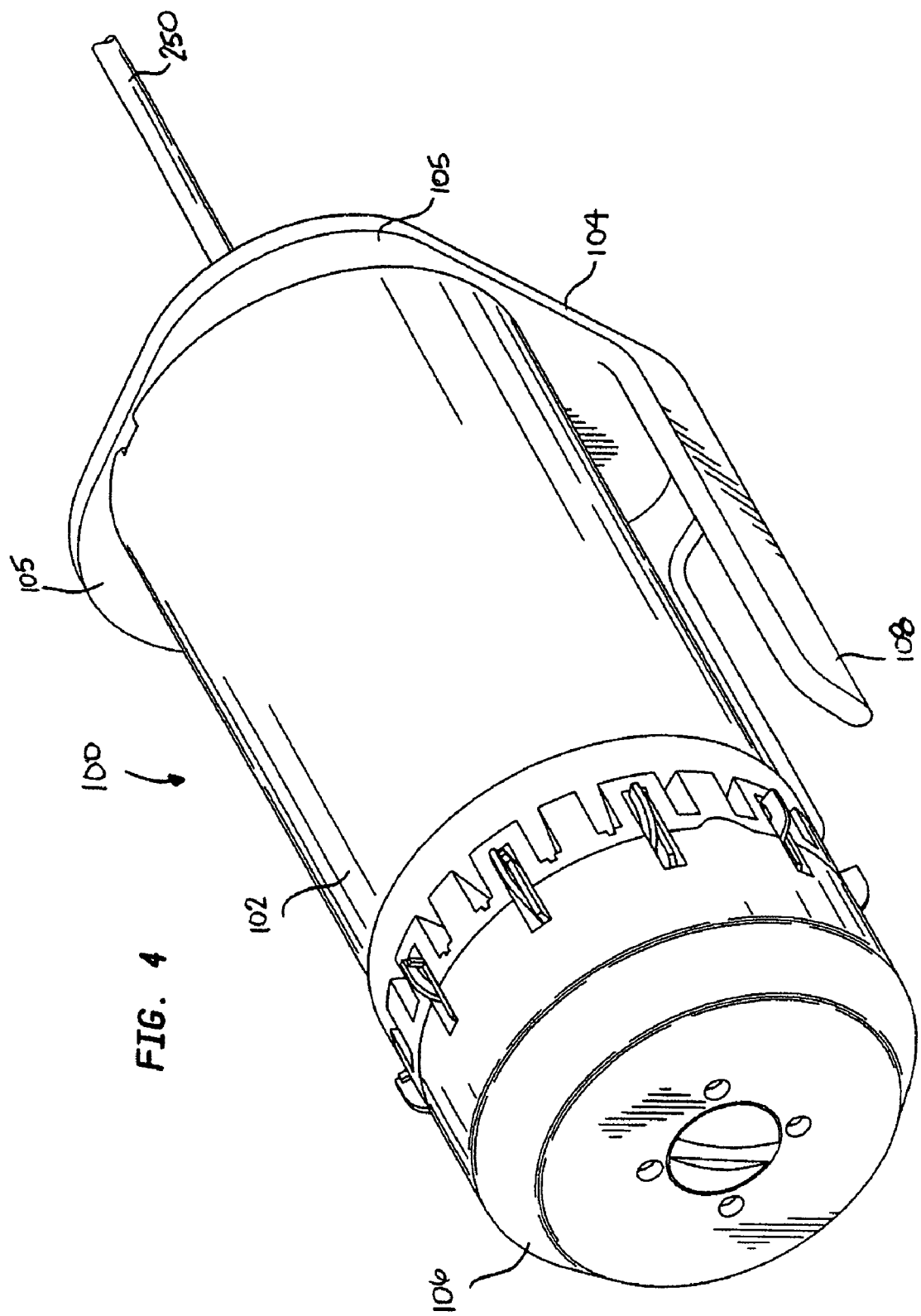
FIG. 4 is a perspective view of a loading unit in accordance with the present invention.

A generally cylindrical side port 20 is provided on one side of main body 12, generally between legs 14 and 16. Side port 20 provides a feature by which graft 10 may be inserted into a patient and held in place during a stapling procedure. In that regard, side port 20 preferably projects from graft 10 at an acute angle relative to legs 14 and 16 to facilitate the insertion of a loading unit 100 (see FIG. 4) therein. As will be explained below, loading unit 100 supports graft 10 and holds it in place relative to the aorta or other tubular body so that the graft may be connected to the body organ by stapling. Optionally, referring to FIG. 2, side port 20 may be provided with one or more sutures 22 adjacent the connection of the side port to main body 12. Suture 22 may be threaded through side port 20 so as to provide a purse string tie by which the side port may be quickly and easily closed following deployment of graft 10. Where graft 10 is not provided with one or more sutures 22, side port 20 may be closed by stapling or by a conventional suturing procedure. Once side port 20 has been closed, any excess graft material may be removed by cutting.

Graft 10 is preferably formed from a biocompatible material having sufficient strength to withstand the surgical implantation procedure described more fully below, as well as the blood flow and other biomechanical forces, which will be exerted on the graft. Such materials may include, for example, polyester materials, such as DACRON©, polytetrafluoroethylene, expanded polytetrafluoroethylene, polyester materials coated with polytetrafluoroethylene, polyurethane, expanded polyurethane and silicone.

Graft 10 may be provided in a range of sizes sufficient to accommodate the arterial morphology, which the surgeon is likely to face in the vast majority of patients. In that regard, graft 10 may be provided with a cuff 18 having a diameter of approximately 16 m, 18 mm or 20 mm, although grafts 10 having larger or smaller diameters are also possible.

Figure 3:
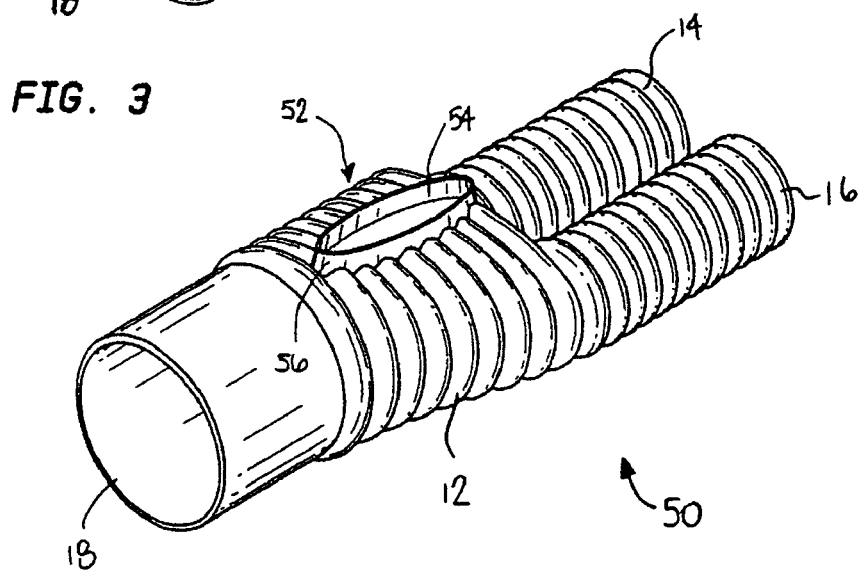
FIG. 3 is a perspective view of a second embodiment of a prosthetic graft for use with the surgical stapling system of the present invention.

A second embodiment of a prosthetic graft 50 for use in the surgical stapling system of the present invention is shown in FIG. 3. Graft 50 is substantially the same as graft 10 described above. However, rather than side port 20, graft 50 includes an elongated flap 52 projecting substantially perpendicularly from main body 12. Flap 52 may be formed by sewing or otherwise connecting individual portions of graft material 54 and 56 in opposed relationship along a longitudinal slit formed in main body 12. Following deployment of graft 50, flap 52 may be closed by stapling or suturing. However, since flap 52 projects from main body 12 by a lesser amount than side port 20, there may be no need to remove any excess material from the flap after it has been closed.

Loading Unit

A loading unit 100 for use in connection with the present invention is shown in FIGS. 4-8. Loading unit 100 has a generally cylindrical body 102 extending in an axial direction, with a generally thin cap 104 at a proximal end thereof and a tapered cap 106 at a distal end thereof. As used herein, the term "proximal" refers to the end of a component or device, which is closest to the actuating handle or surgeon, and the term "distal" refers to the end of a component or device that is farthest away from the actuating handle or surgeon. Cap 104 may have portions that protrude beyond the diameter of body 102 so as to define flanges 105. The tapered portion of cap 106 facilitates the assembly of a graft 10 onto loading unit 100 at one end, while flanges 105 act as a stop to prevent the graft from being pushed off the loading unit at the other end. A pair of fingers 108 projecting from cap 104 in the axial direction of body 102 but at a spaced distance therefrom help keep the graft in its assembled position on loading unit 100 and keep the legs 14 and 16 of the graft in a controlled position. A plurality of apertures 107 formed in cap 104 are sized and positioned to receive the fingers of a pusher 600 to be described below in connection with the stapling instrument.

Figure 5:
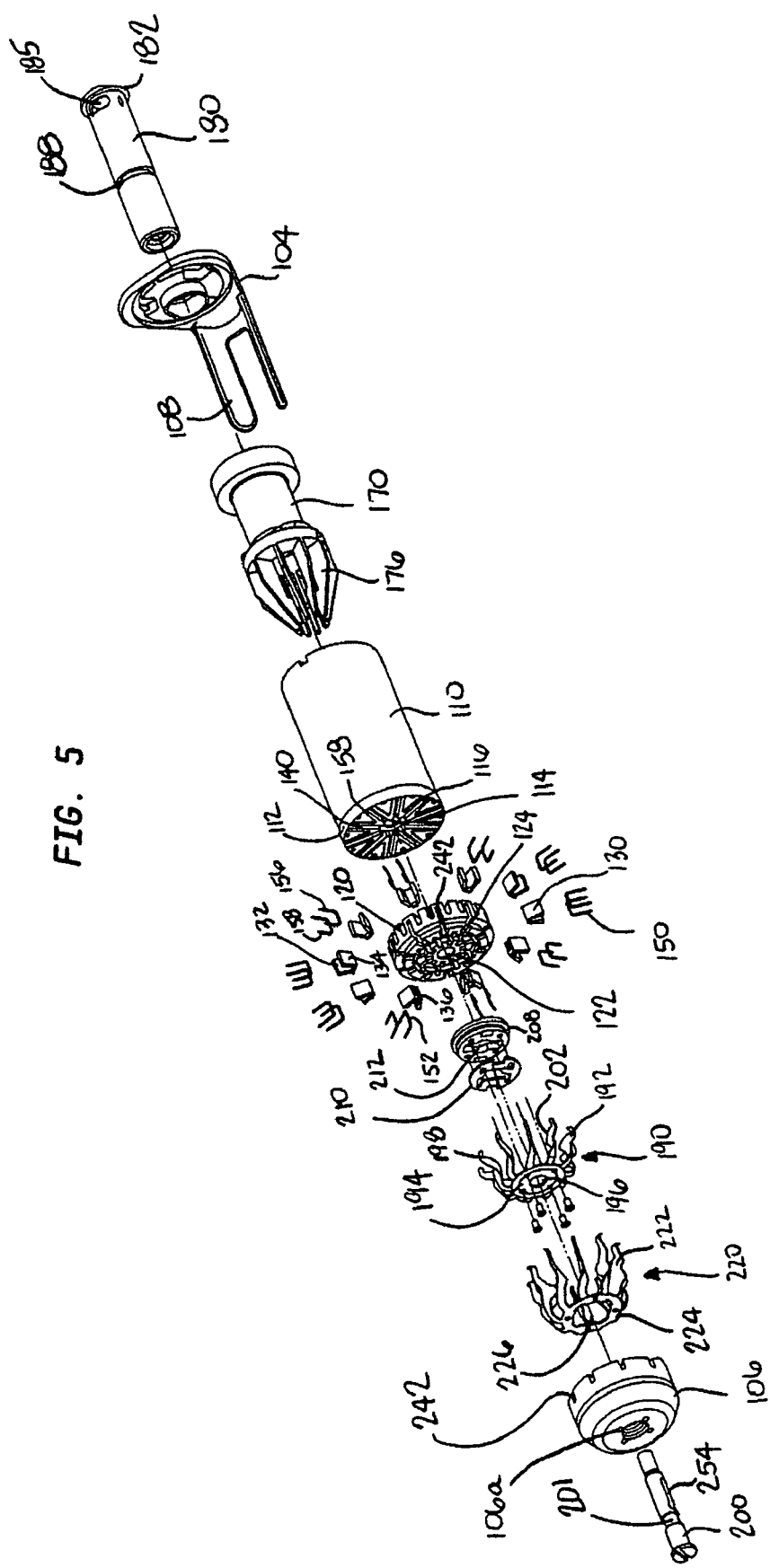
FIG. 5 is a front perspective exploded view of the loading unit shown in FIG. 4.
Figure 6:
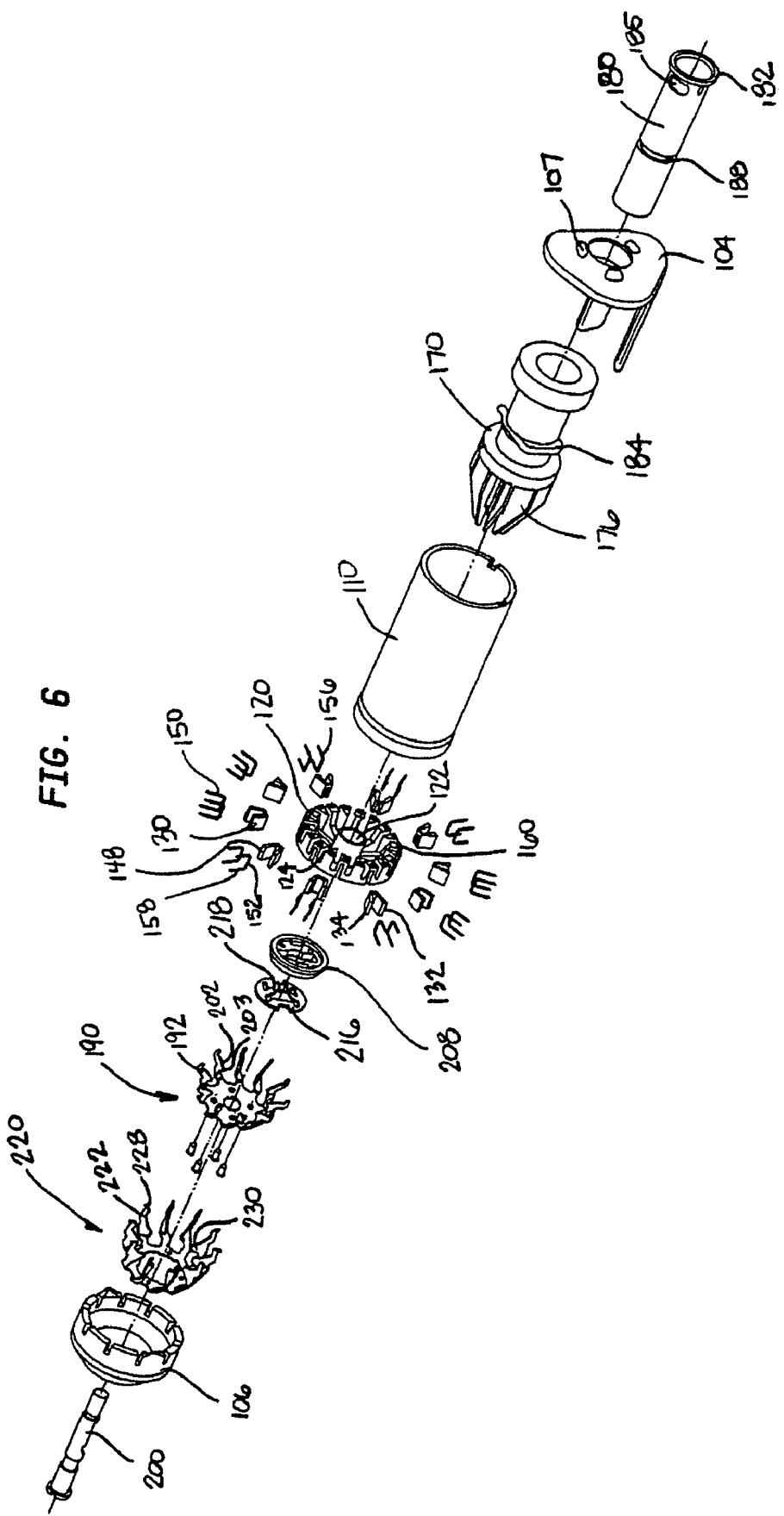
FIG. 6 is a rear perspective exploded view of the loading unit shown in FIG. 4.

Referring to the exploded views of FIGS. 5 and 6, loading unit 100 includes a hollow, generally cylindrical cartridge 110. Cartridge 110 is open at its proximal end for slidably receiving an actuator 170, and has an end member 112 at its distal end. End member 112 has a central aperture 114 and a plurality of radially projecting slots 116 for receiving elongated fingers 176 provided on the distal end of actuator 170.

At its distal end, cartridge 110 mates with a second cylindrical cartridge 120. Cartridge 120 has a central aperture 122 that aligns with aperture 114 of cartridge 110, and a plurality of radially extending slots 124, each of which aligns with a corresponding slot 116 in the distal end of cartridge 110 for receiving the elongated fingers 176 of actuator 170. A plurality of projections (not shown) on the proximal surface of cartridge 120 mate with corresponding recesses (not shown) formed in the end member 112 of cartridge 110 so as to maintain cartridge 120 in registry with cartridge 110.

A plurality of staple pushers 130 are arranged between cartridge 110 and cartridge 120 for radial sliding movement between an inner staple holding position and an outer staple ejecting position. The number of staple pushers 130 utilized will depend on the number of staples to be simultaneously deployed during a stapling procedure. The preferred embodiment of the invention described herein includes ten staple pushers 130 for deploying twenty staples. It will be appreciated, however, that a greater or lesser number of staple pushers may be utilized depending on the number of staples to be deployed and physical constraints dictated by the size and operation of loading unit 100.

Each staple pusher 130 has a generally U-shaped profile consisting of first and second legs 132 and 134 connected by an intermediate portion 136. Intermediate portion 136 has a first laterally projecting tab 138 that slidably engages in one of a plurality of recessed channels 140 formed in the end member 112 of cartridge 110. Recessed channels 140 coincide with radially projecting slots 116, but are larger in width and length. The opposite side of intermediate portion 136 has a second laterally projecting tab 142 that slidably engages in one of radial slots 124 formed in cartridge 120. Tab 142 projects from intermediate portion 136 adjacent the inner end 144 of staple pusher 130. Tab 138, on the other hand, projects from intermediate portion 136 at a spaced distance from end 144 of staple pusher 130. A recessed slanted cam surface 146 is formed in intermediate portion 136 between tabs 138 and 142, the purpose of which will be described below.

Prior to a stapling operation, with staple pushers 130 in their inner staple holding positions, loading unit 100 includes a plurality of surgical staples 150. Staples 150 are loaded in loading unit 100 so that the crossmember 152 of each staple rests against the free end of one of legs 132, 134 of staple pushers 130, with staple legs 154 and 156 projecting radially outward. More particularly, the crossmember 152 of each staple rests in an elongated recess 148 formed in the free ends of the legs 132 and 134 of each staple pusher 130. Further, the legs 154 and 156 of staples 150 reside within opposed radially extending guide channels 158 and 160, respectively, guide channel 158 being formed in end member 112 of cartridge 100, and guide channel 160 being formed in cartridge 120. Recesses 148 locate the staples and hold them in place with respect to the free ends of legs 132 and 134, while guide channels 158 and 160 guide the staples as they are deployed from loading unit 100. It will be appreciated from the foregoing that a loading unit 100 having ten staple pushers 130, and therefore twenty legs 132, 134, will be able to simultaneously deploy twenty staples 150.

Legs 132, 134 of staple pushers 130 each include a pair of lateral ribs 162 positioned in linear alignment with recess 148. Ribs 162 are aligned substantially collinearly with legs 154 and 156 of staples 150 so that, upon outward radial movement of staple pushers 130, the force exerted by the staple pusher is distributed along the entire length of crossmember 152, with a portion of the force being exerted in substantial linear alignment with the staple legs. As a result, any resistance to this outward movement as the free ends of staple legs 154 and 156 contact and pierce the aorta and graft 10 and strike the stapling anvils (to be described below) will not result in significant distortion to crossmember 152.

Staple pushers 130 are moved from their inner staple holding positions to their outer staple ejecting positions by actuator 170. Actuator 170 has a generally tubular main body 172 with an annular flange 174 at the proximal end thereof, and a plurality of elongated fingers 176 at the distal end thereof. Fingers 176 are sized and shaped to be slidably received in the slots 116 of cartridge 110 and the slots 124 of cartridge 120. Each of fingers 176 includes a tapered surface 178, which cooperates with the cam surface 146 of a corresponding staple pusher 130 to move the staple pusher radially outward during a stapling operation, as will be described below.

Actuator 170 is mounted on a tubular shaft 180 for sliding movement in the axial direction of loading unit 100. Shaft 180 has an enlarged annular flange 182 at its proximal end to prevent cap 104 from sliding axially beyond the proximal end of the shaft. A retaining clip 184 is assembled over a pair of transverse slots 186 formed in the main body 172 of actuator 170 and cooperates with an annular groove 188 formed in shaft 180 to temporarily prevent actuator 170 from sliding on shaft 180. The spring force of retaining clip 184 is only sufficient to prevent the unintended relative movement of actuator 170 on shaft 190 during shipping and handling of loading unit 100. During a stapling operation, however, the force exerted axially on actuator 170 is sufficient to overcome the spring force of retaining clip 184. That is, during a stapling operation, the axial force exerted on actuator 170 causes retaining clip 184 to spread open as it is pushed against the side of annular groove 188 until the retaining clip is pushed out of the groove, thereby enabling actuator 170 to slide axially along shaft 180. A pair of cutouts 185 are formed on the opposite sides of shaft 180 near its proximal end, the purpose of which will be discussed below.

Between cartridge 120 and cap 106, loading unit 100 includes an assembly for gripping the distal edge of graft 10 and holding it in place during shipment of the stapling system of the present invention and during a stapling procedure. The assembly includes an external graft retainer 190 having a plurality of fingers 192 which may be extended radially outward from loading unit 100 to grip the outer distal edge of graft 10, and an internal graft retainer 220 having a plurality of fingers 222 which may be extended radially outward from the loading unit to pierce the inner distal edge of graft 10. Retainers 190 and 220 are assembled over the shaft of an elongated screw 200 which extends through an aperture in cap 106, the central apertures in cartridges 110 and 120, and actuator 170, and which ultimately connects at its proximal end to the distal end of shaft 180 to hold all of the components of loading unit 100 in assembled relationship. Screw 200 may be joined to shaft 180 by any technique, including, for example, threaded engagement.

External graft retainer 190 includes a generally flat, circular hub 194 having a central aperture 196 for receiving the shaft of crew 200. Fingers 192 may be formed integrally with hub 194 and extend in a direction proximally and radially outward thereof. Each finger 192 terminates in a generally L-shaped tip 198 having a surface 198a extending in a generally radial direction and a surface 198b extending proximally therefrom in a generally axial direction. An angled cam surface 202 provided between tip 198 and hub 194 includes a protruding portion or bump 203 at the end of the cam surface farthest from tip 198. Retainer 190 is preferably formed from spring steel or a similar material and shaped so that fingers 192 will be biased toward their rest positions when displaced radially outward therefrom.

A cam ring 208 is mounted to hub 194 of retainer 190 by a plurality of screws or other known fastening technique, with a spring member 210 sandwiched therebetween. Cam ring 208 has an elongated central aperture 212 and a shaped surface 214 along its outer periphery. More particularly, the outer periphery of cam ring 208 includes a smaller diameter annular surface 208a, a larger diameter annular surface 208b, and a tapered surface 208c therebetween, the purpose of which surfaces will be described below. Spring member 210 has a generally flat body portion 216 and a pair of tabs 218 bent in a proximal direction. Tabs 218 reside in an annular channel 201 formed in the shaft of screw 200, thereby limiting the amount by which retainer 190 may move in the axial direction.

Internal graft retainer 220 includes a generally flat circular hub 224 having an enlarged opening 226. Opening 226 has enlarged regions that receive bosses 240 projecting from the interior of cap 106. Bosses 240 are undercut so that retainer 220 may be rotated relative to cap 106 to lock it in place on the interior of the cap.

Fingers 222 of retainer 220 may be formed integrally with hub 224 and extend in a direction proximally and radially outward thereof. Each finger 222 terminates in a needle-like tip 228 which projects radially outward. A radially inward projecting cam 230 formed on each finger 222 intermediate tip 228 and hub 224 has an angled distal cam surface 230a, a cam surface 230b which extends generally in the axial direction, and an angled proximal cam surface 230c. Cam 230 is adapted to cooperate with the shaped peripheral surface 214 of cam ring 208 as will [sic] described further below. Retainer 220 is preferably formed from the same spring steel or similar material as retainer 190 and shaped so that fingers 222 will be biased toward their rest positions when displaced radially outward therefrom.

In the assembled condition of loading unit 100, retainers 190 and 220 are positioned relative to one another so that each finger 192 of retainer 190 lies adjacent a finger 222 of retainer 220. Each pair of fingers 192, 222 resides in one of a plurality of radial recesses 242 formed in the distal surface of cartridge 120 and continuing in the proximal surface of cap 106. Each recess 242 includes a first surface 242a extending generally in an axial direction, and a cam surface 242b extending at an angle to surface 242a. The surfaces 242a and 242b of each recess 242 are intended to interact with the cam surface 202 and bump 203 of the finger 192 residing in that recess, as will be explained further below.

A guidewire 250 is connected at one end to loading unit 100 and projects outward from the proximal end thereof. Guidewire 250 has an enlarged end 252 formed in a conventional fashion. End 252 is receivable in a slot 254 having an enlarged end 256 formed in the shaft of screw 200. The guidewire then extends through an axial bore (not shown) in the shaft of screw 200, through the hollow center of shaft 180 and out the proximal end of loading unit 100. The engagement of the enlarged end 252 of guidewire 250 in the enlarged end 256 of slot 254 locks the guidewire in place and prevents it from being pulled proximally out from loading unit 100.

Figure 7A:
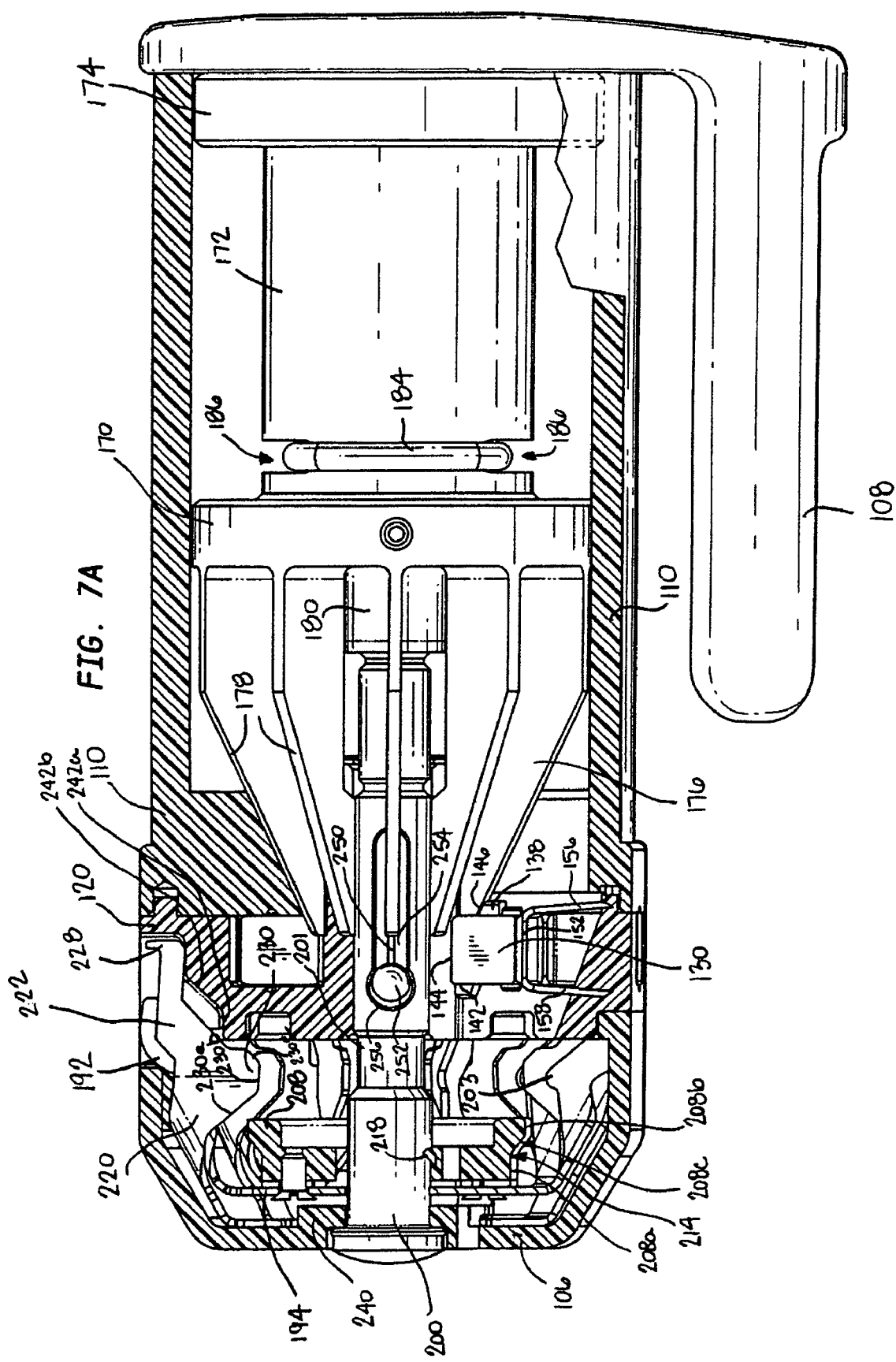
FIG. 7A is a longitudinal view, in partial cross-section of the loading unit in a state for loading a graft thereto.
Figure 7B:
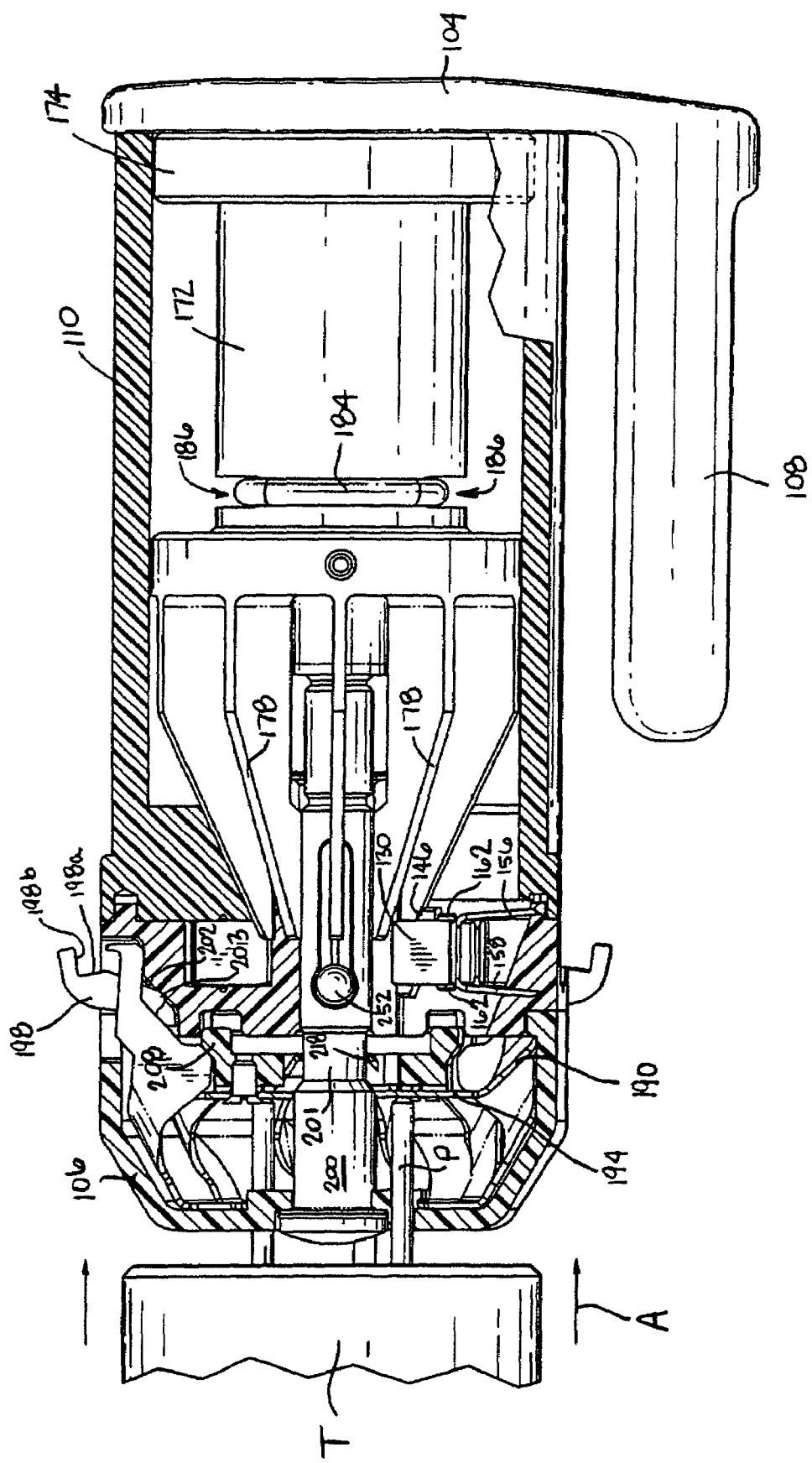
FIG. 7B is the same view as FIG. 7A, but showing the loading unit in a state for loading a prosthetic graft therein.

A procedure will now be described for mounting a graft 10 onto loading unit 100, which procedure is typically performed in a factory prior to shipment of the stapling system of the present invention. FIG. 7A shows a cross-sectional view of loading unit 100 in an initial state for loading a graft thereto. In this position, fingers 192 on retainer 190 are positioned in recesses 242 spanning cartridge 120 and cap 106 so that bumps 203 on fingers 192 lie distally of the cartridge, i.e., they are not located on any cam surface. As a result, fingers 192 are positioned so that the tips 198 thereof lie below the outer surface of the loading unit. With retainer 190 positioned as described, the cam ring 208 will be positioned axially so that the cams 230 on the fingers 222 of retainer 220 are proximal of the cam ring, i.e., they are not supported by any of the surfaces of the cam ring. As a result, the tips 228 of fingers 222 are positioned below the outer surface of the loading unit.

In this initial condition, loading unit 100 may be inserted into side port 20 of graft 10 until the distal end of cartridge 110 protrudes from cuff 18. With graft 10 being held in this position, an actuating tool T may be used to advance retainer 190 to the loading position shown in FIG. 7B. Actuating tool T has a series of pins P that may be inserted into corresponding apertures 106a in cap 106. As actuating tool T is moved in the axial direction of arrow A shown in FIG. 7B, pins P engage the hub 194 of retainer 190, forcing the retainer in the proximal direction. As retainer 190 moves proximally, cam surfaces 202 on fingers 192 engage the edge of cartridge 120 in the recesses 242, thereby forcing fingers 192 radially outward. Continued movement of retainer 190 will cause bumps 203 on fingers 192 to travel across cam surface 242a and to begin traveling up cam surface 242b to the position shown in FIG. 7B, at which the tips 198 of the fingers are spaced outwardly from the loading unit. The movement of retainer 190 proximally also causes spring member 210 to move proximally, whereupon spring tabs 218 will enter channel 201 formed in the shaft of screw 200. It should be noted that channel 201 has a width in the axial direction, which is sufficiently large that spring tabs do not contact the proximal wall of the channel before fingers 192 have moved radially outward by a far enough distance.

The proximal movement of retainer 190 also causes cam ring 208 to proximally, whereupon the proximal edge of the cam ring will ride along the cam surfaces of the cams 230 on fingers 222 until cam surfaces 230c slide down tapered surface 208c on the cam ring and cam surfaces 230b come to rest on smaller diameter annular surface 208a. As in the initial starting position, the tips 228 of fingers 222 will be positioned below the outer surface of loading unit 100.

With fingers 192 and 222 in these positions, graft 10 can be positioned so that the free edge of cuff 18 rests against surface 198a and below surface 198b at the tip of each finger 192. At this point, actuating tool T may be moved in the direction of arrows B shown in FIG. 7C and removed from loading unit 100. With the actuating tool T no longer holding retainer 190 in place, the radially inward biasing force of fingers 192, through the interaction of bumps 203 with cam surfaces 242b, biases retainer 190 in the distal direction. At the same time, the tapered surface 208c on cam ring 208 will engage the cam surfaces 230c on fingers 222 to push fingers 222 radially outward against the radially inward biasing force of the fingers. The biasing force exerted by fingers 192 preferably is deliberately designed to be greater than the biasing force exerted by fingers 222 so that retainer 190 moves in the distal direction. Optionally, a spring element (not shown) may be assembled between cam ring 208 and cartridge 120 to assure that retainer 190 moves in the distal direction upon removal of actuating tool T from loading unit 100. The distal movement of retainer 190 continues until spring tabs 218 strike the distal wall of annular channel 201. Alternatively, where graft 10 has sufficient strength, retainer 190 may move distally until the surfaces 198b at the tip of fingers 192 contact the graft, whereupon the graft prevents further inward movement of the fingers and, hence, further distal movement of retainer 190.

Figure 8:
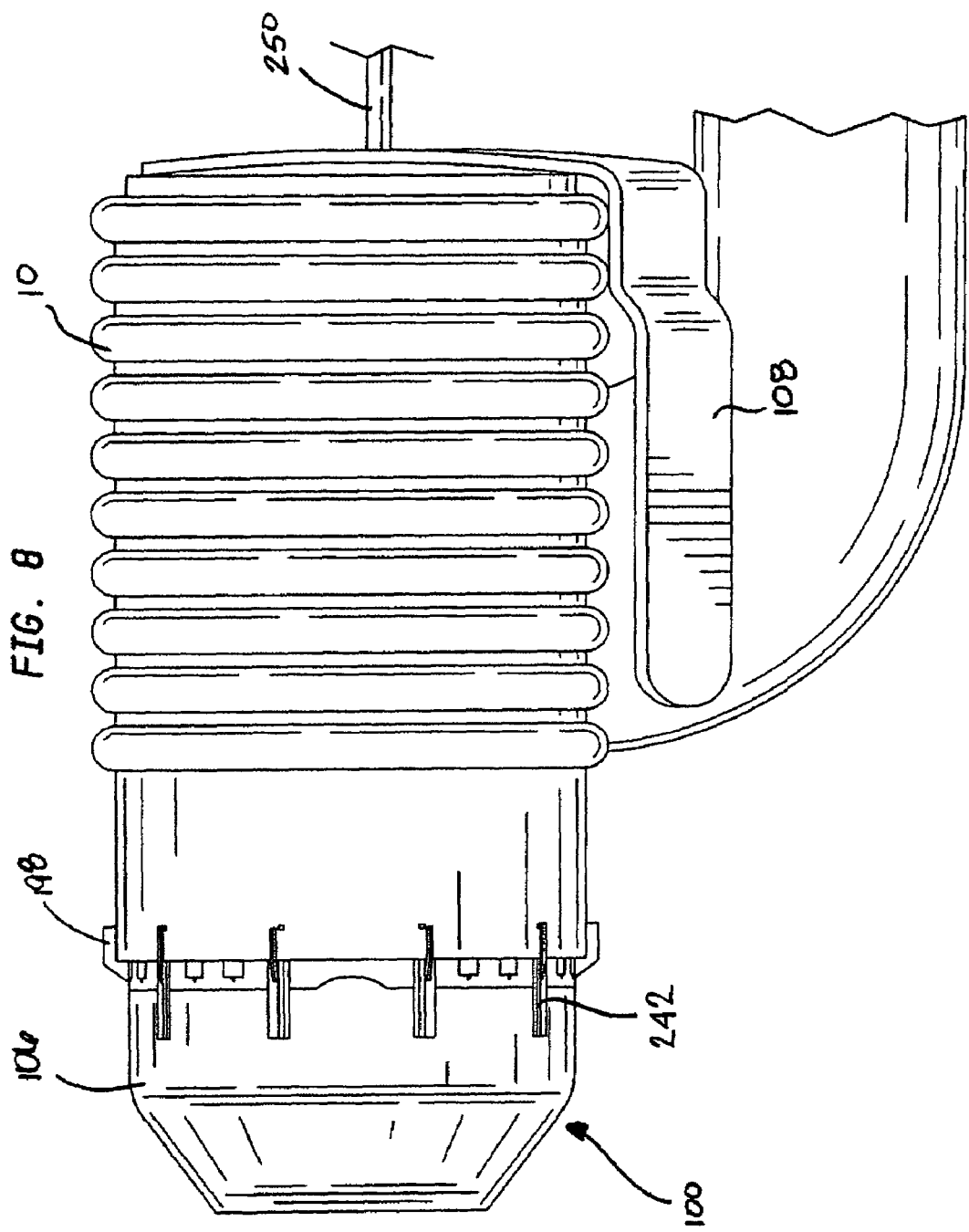
FIG. 8 is an elevational view of the loading unit showing a prosthetic graft loaded thereon.

In either event, as retainer 190 moves distally, cam ring 208 moves distally with it. This movement causes the cam surfaces 230c on fingers 222 to ride up the tapered surface 208c on cam ring 208, with cam surfaces 230b ultimately coming to rest on larger diameter annular surface 208b. This action causes fingers 222 to expand radially outward of loading unit 100 so that the tips 228 thereof pierce graft 10 from the inside. The interaction of the tips 198 of fingers 192 and the tips 228 of fingers 222 with graft 10 hold the graft securely on loading unit 100. That is, with tabs 218 of spring member 210 abutting the distal wall of annular channel 201, retainer 190 is prevented from moving further in the distal direction. Furthermore, the interaction of the bumps 203 on fingers 192 with cam surfaces 242b prevents retainer 190 from moving proximally in the axial direction since any such movement would have to overcome the biasing force of fingers 192. With retainer 190 unable to move axially in either direction, the tips 198 of fingers 192 and the tips 228 of fingers 222 remain in fixed positions and hold graft 10 securely in place. An elevational view of the loading unit 100 having a graft 10 loaded thereon is shown in FIG. 8.

In a variant of loading unit 100 described above, rather than relying upon the relative biasing forces exerted by fingers 192 and 222, or upon an optional spring assembled between cam ring 208 and cartridge 120, the pins P of actuating tool T may be provided with a feature which engages a corresponding feature in the hub 194 of retainer 190 so that actuating tool T may be used to manually pull retainer 190 distally to an appropriate position.

It will be appreciated that loading unit 100 may be provided in a series of different diameters which correspond to the diameters in which graft 10 is provided. Thus, graft 10 and loading unit 100 are typically provided as a unit, with graft 10 mounted on a loading unit in condition for ready use by the surgeon.

Wand

Figure 9:
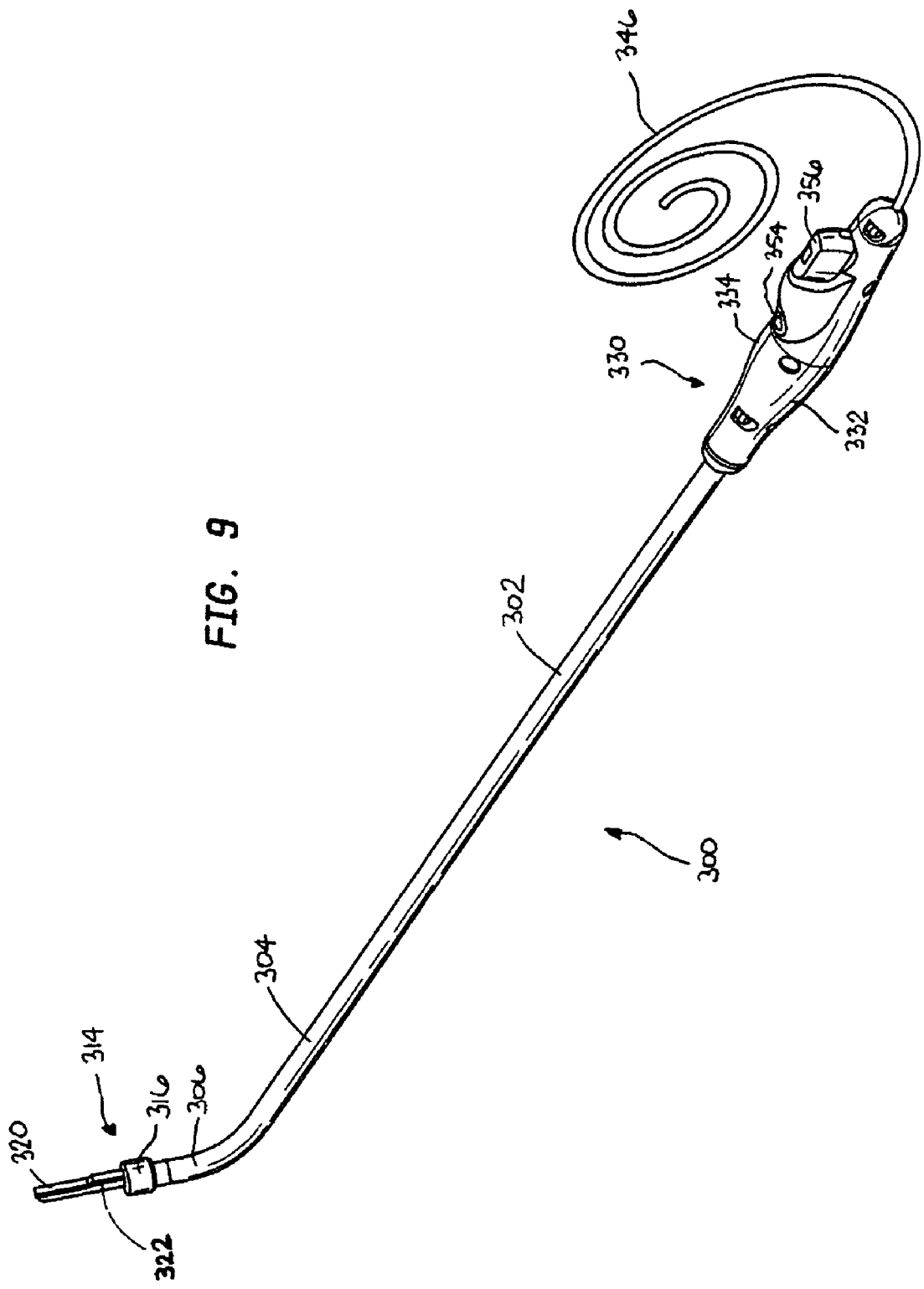
FIG. 9 is a perspective view of a placement wand in accordance with a first embodiment of the present invention.

FIGS. 9-10 illustrate a placement wand 300 in accordance with one embodiment of the present invention. Wand 300 is a lightweight, maneuverable tool used to insert loading unit 100 and its associated graft into the proper surgical position and to hold them in place as the graft is temporarily secured to the aorta for a subsequent stapling procedure. Wand 300 includes a shaft 302 having a substantially straight elongated portion 304 and a distal end portion 306, which is oriented at an angle relative to elongated portion 304. End portion 306 may form an angle of between about 90° and about 180° with elongated portion 304. In preferred embodiments, end portion 306 forms an angle of between about 105° and about 125° with elongated portion 304, with an angle of about 115° being most preferred. A bore 308 extending through the entire length of shaft 302 is sized to receive guidewire 250 as loading unit 100 is assembled to wand 300.

An attachment mechanism 314 is connected to the distal end of shaft 302. Attachment mechanism 314 has a cylindrical end portion 316 having a counterbore sized for receiving the distal end of shaft 302. A flat may be formed in the counterbore so as to mate with a corresponding flat formed on the distal end of shaft 302, thereby defining the proper rotational relationship between attachment mechanism 314 and shaft 302. Attachment mechanism 314 may be held in assembled relationship on shaft 302 by a set screw (not shown) or any other known fastening technique.

Projecting distally from end portion 316 of attachment mechanism 314 is an elongated finger 320. Finger 320 has a pair of flat side surfaces 322, a curved upper surface 326 and a flat lower surface. The shapes of these surfaces coincide with the internal shape of shaft 180 of loading unit 100 so that the loading unit is unable to rotate once assembled to wand 300. A bore (not shown) extending through attachment mechanism 314 aligns with bore 308 in shaft 302 when these components are assembled together.

At its proximal end, wand 300 includes an operating handle 330 having first and second handle portions 332 and 334 that may be assembled together using any conventional technique. Handle 330 may be assembled to the proximal end of shaft 302 by capturing a reduced diameter portion 336 of shaft 302 between the handle portions when they are assembled together. A pair of projections 338 and 340 formed in each of handle portions 332 and 334 engage a pair of grooves 342 and 344, respectively, formed transversely in shaft 302 to locate shaft 302 in the proper rotational orientation relative to handle 330 and to prevent the shaft from sliding out of the handle when in the assembled position. Coiled guidewire tubing 346 is held in the proximal end of handle 330 by the assembly of handle portions 332 and 334. Guidewire tubing 346 receives the excess length of guidewire 250, which protrudes out from the proximal end of wand 300 and holds it in a manageable position. When wand 300 is removed from loading unit 100, as explained below, coiled tubing 346 may first be removed from handle 330 by pulling to expose guidewire 250. Alternatively, guidewire tubing 346 may remain connected to handle 330, and guidewire 250 may simply be pulled out from the tubing as wand 300 is removed from loading unit 100.

Handle 330 includes a locking mechanism 350 operable between a locked position for engaging guidewire 250 so as to prevent sliding movement between wand 300 and the guidewire, and an unlocked position for releasing the wand for movement relative to the guidewire. In the embodiment shown in FIGS. 9-10, locking mechanism 350 may operate as a toggle. Thus, locking mechanism 350 may include a trigger lock 352 having a first operating button 354 and a second operating button 356 provided on either side of a pivot member (not shown). The ends of the pivot member are held by handle portions 332 and 334 so that trigger lock 352 is free to pivot between the locked and unlocked positions. A brake 360 having a pivot member (not shown) at one end thereof is pivotably mounted in handle 330 below trigger lock 352, and a friction member 364 is mounted below brake 360. Friction member 364 is preferably formed from a soft, resilient material which, when pressed with sufficient force against guidewire 250, will prevent wand 300 from sliding relative to the guidewire. In that regard, friction member 364 may be formed from a resilient plastic, rubber or like material. Preferably, friction member 364 is formed from silicone rubber, and more preferably, is formed from a length of silicone rubber tubing. Brake 360 cooperates with friction member 364 to lock wand 300 to guidewire 250 in the locked position of locking mechanism 350 and to release wand 300 for movement relative to guidewire 250 in the unlocked position of locking mechanism 350.

Figure 10A:
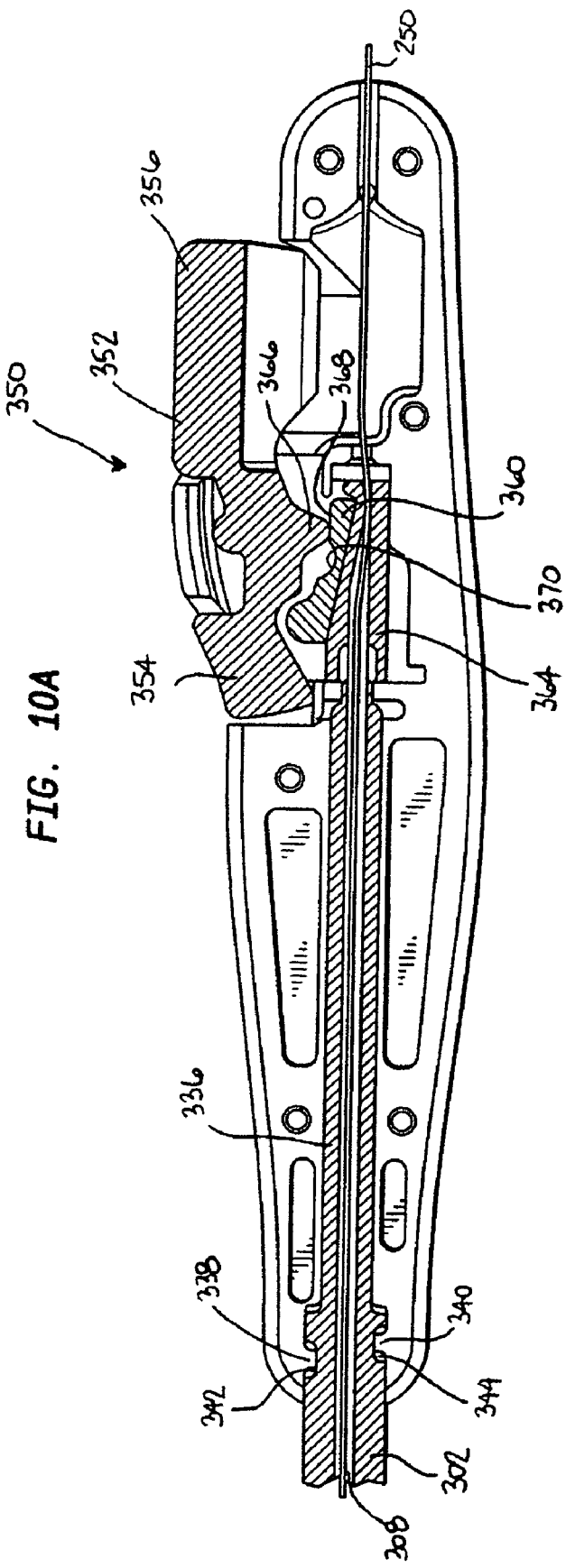
FIG. 10A is cross-sectional view of the handle of the wand of FIG. 9 in a locked condition.

More particularly, in the locked condition of locking mechanism 350, button 354 is in the depressed position shown in FIG. 10A. In this position, an arcuate locking protrusion 366 formed on trigger lock 352 below its pivot member rests on a raised flat region 368 on the upper surface of brake 360. As a result, brake 360 is forced downwardly against friction member 364, forcing it tightly against guidewire 250 and preventing relative movement between the guidewire and wand 300. Where friction member 364 has a tubular structure, the downward force exerted by brake 360 causes the tubular structure to collapse, thereby engaging guidewire 250 between the opposed inner walls of the tube.

Figure 10B:
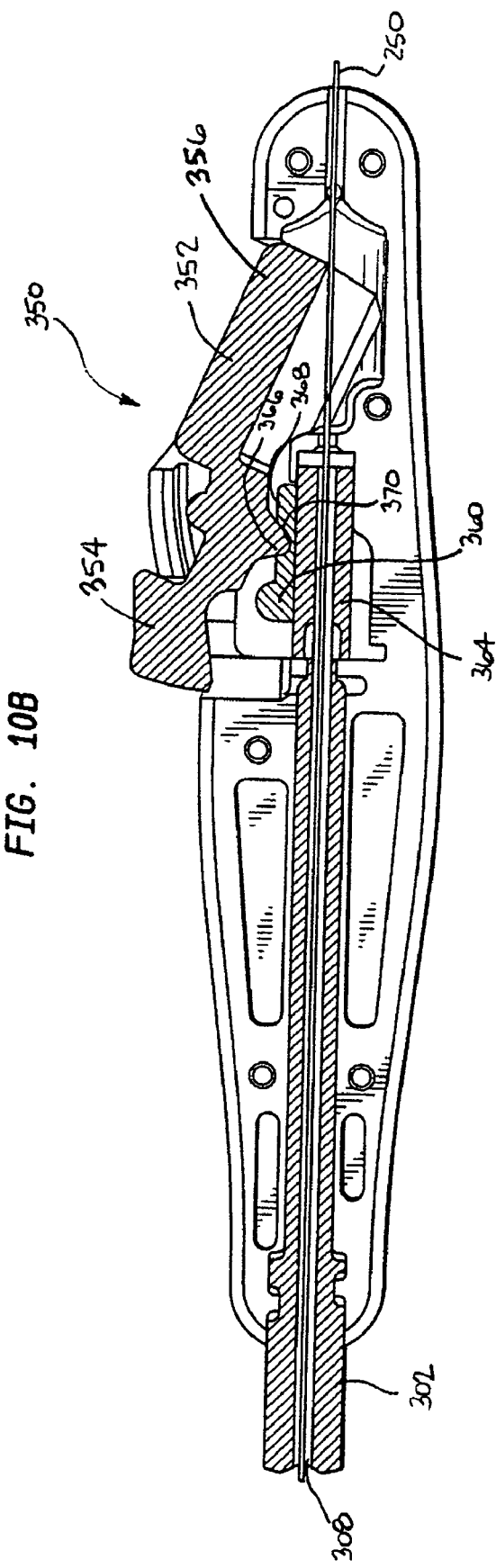
FIG. 10B is the same view as FIG. 10A, but showing the wand handle in an unlocked condition.

Depressing button 356 to move trigger lock 352 to the unlocked position shown in FIG. 10B causes locking protrusion 366 to rotate about its pivot member until it lies over a recessed region 370 formed in the upper surface of brake 360. With brake 360 no longer held tightly against friction member 364, the resiliency of the friction member pushes brake 360 upwardly until locking protrusion 366 rests within recessed region 370. As a result, friction member 364 is no longer compressed against guidewire 250, and the guidewire is released for sliding movement relative to wand 300.

Figure 11:
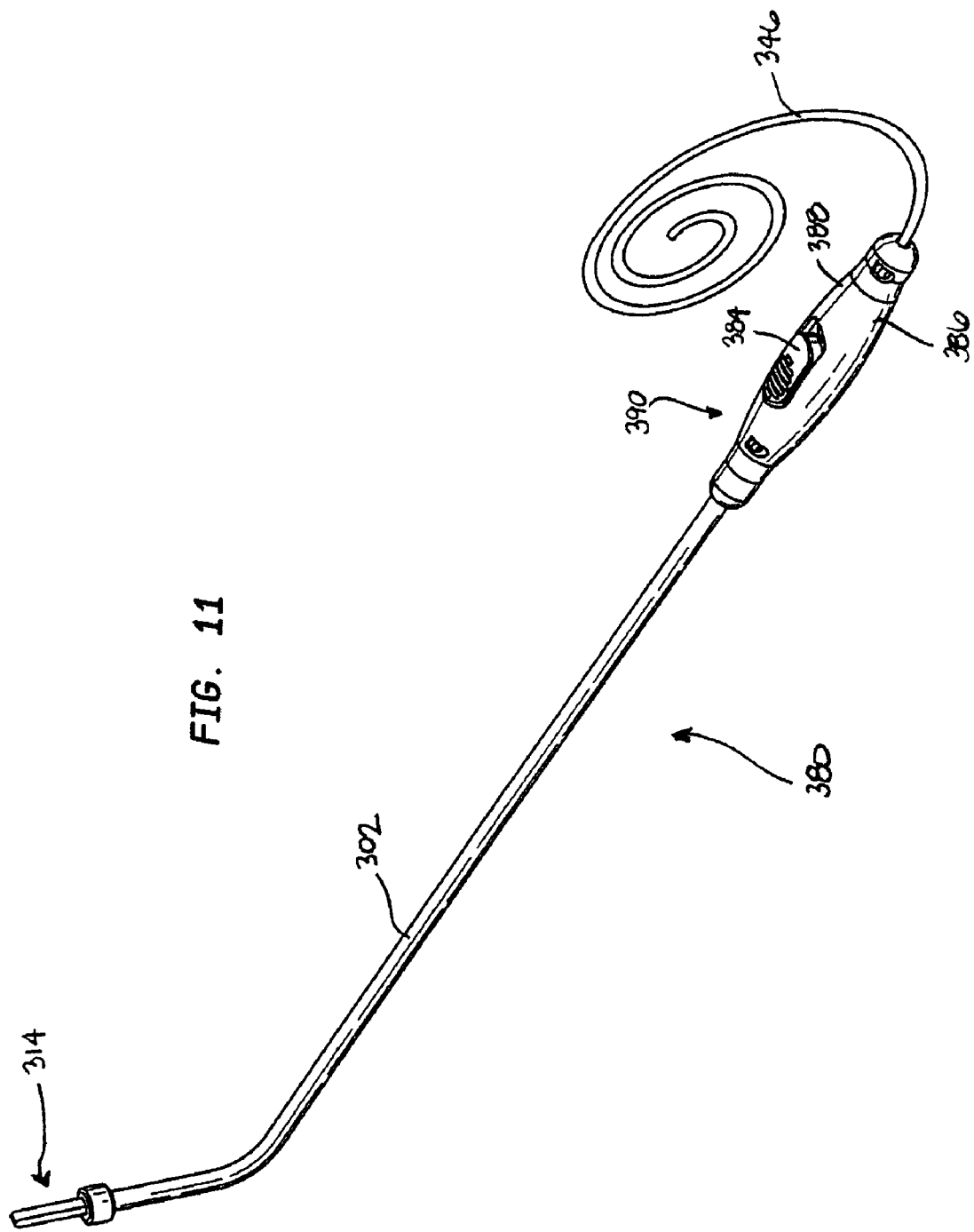
FIG. 11 is a perspective view of a placement wand in accordance with a second embodiment of the present invention.

A second embodiment of a placement wand 380 for use with the present invention is shown in FIGS. 11-12. Wand 380 is substantially the same as wand 300, but has a locking mechanism 382 which uses a slidable trigger lock 384 rather than the trigger lock 352, which operates in a toggle, fashion. Trigger lock 384 slides between locked and unlocked positions in an elongated cavity 385 formed in first and second handle portions 386 and 388 of operating handle 390. A locking protrusion 392 projects downwardly from trigger lock 384 at the proximal end thereof. A brake 394 having a pivot member (not shown) at one end thereof is pivotally mounted in handle 390 below locking protrusion 392, and a friction member 398 is mounted below brake 394. Friction member 398 is preferably formed from the same silicone rubber tubing as described above in connection with friction member 364 of wand 300.

Figure 12A:
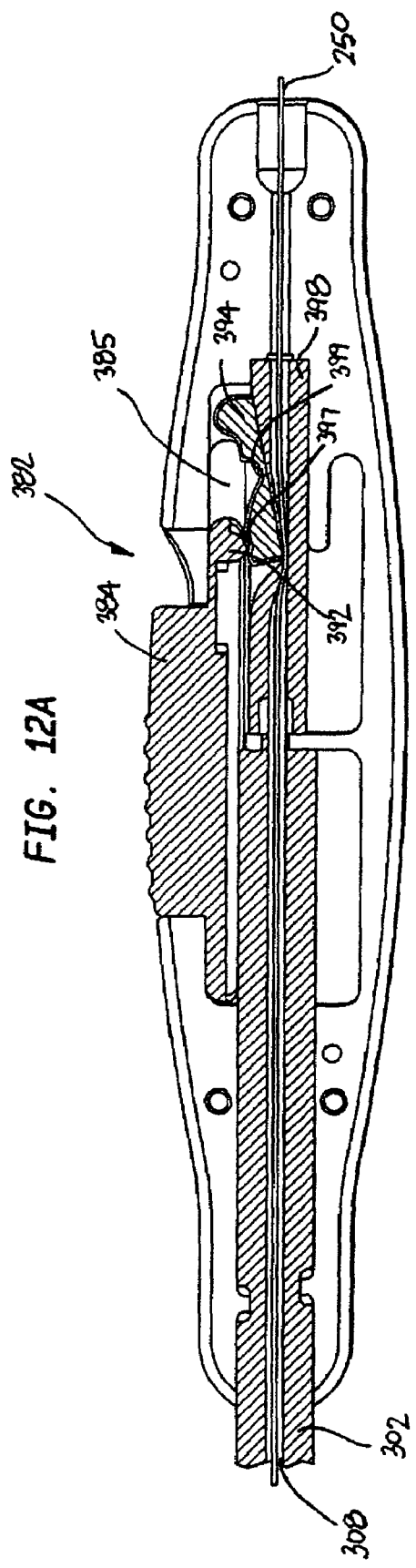
FIG. 12A is a cross-sectional view of the handle of the wand of FIG. 11 in a locked condition.

In the locked condition of locking mechanism 382, the trigger lock 384 is slid to the distal position shown in FIG. 12A. In this position, locking protrusion 392 rests in a shallow depression formed in a raised region 397 on the upper surface of brake 394. As a result, brake 394 is forced downwardly against friction member 398, engaging guidewire 250 and preventing its movement relative to wand 380.

Figure 12B:
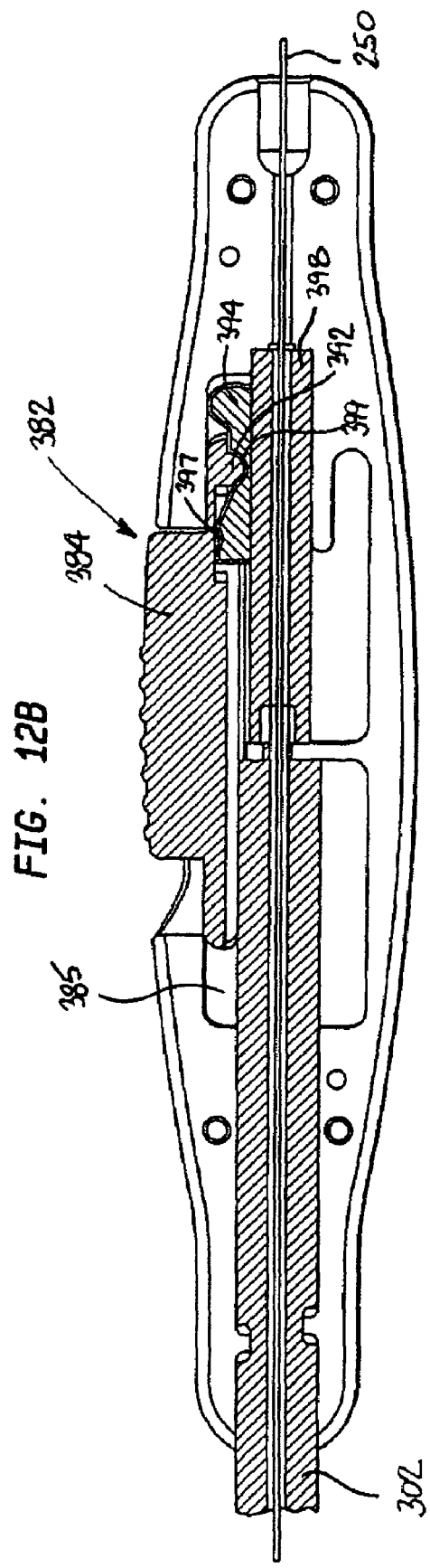
FIG. 12B is the same view as FIG. 12A, but showing the wand handle in an unlocked condition.

Sliding trigger lock 384 in the proximal direction to the unlocked position shown in FIG. 12B moves locking protrusion 392 to a position overlying a recessed region 399 formed in the upper surface of brake 394. The resiliency of friction member 398 thus pushes brake 394 upwardly until locking protrusion 392 rests within recess region 399. As a result, friction member 398 is no longer compressed against guidewire 250 and the guidewire is released for sliding movement relative to wand 380.

Tourniquet

Figure 13:
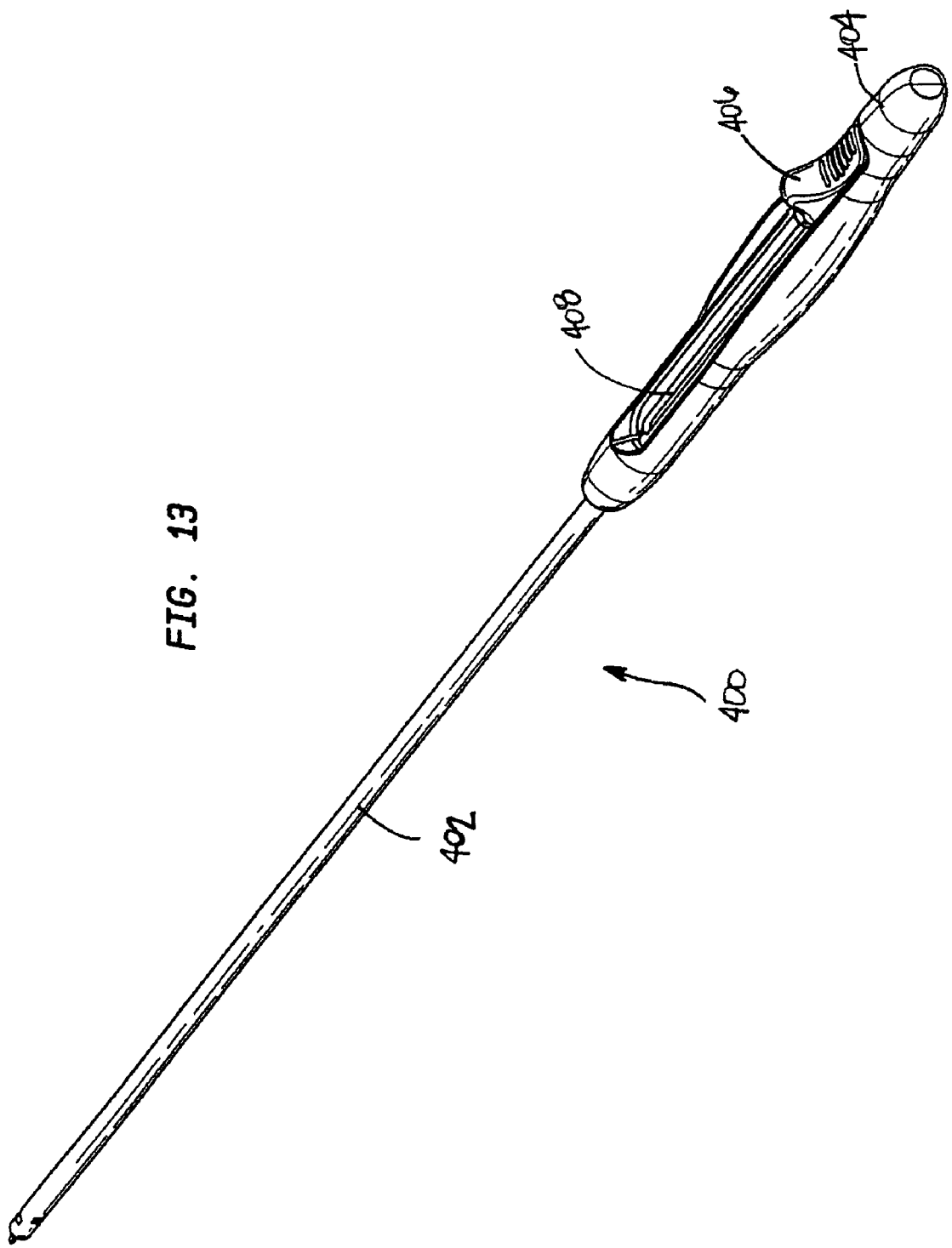
FIG. 13 is a perspective view of a tourniquet for use in the present invention.
Figure 14C:
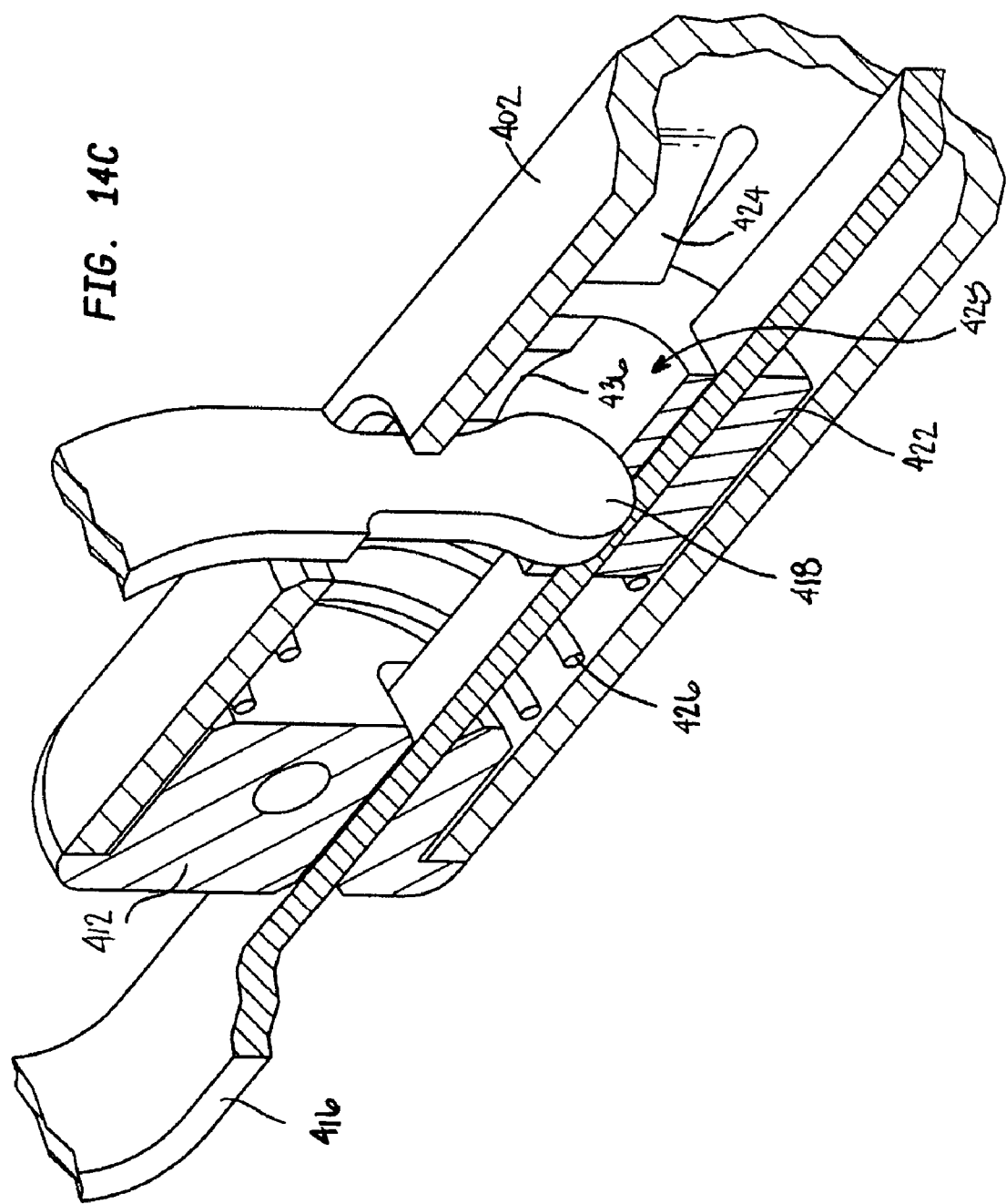
FIG. 14C is the same view as FIG. 14A, but showing the band in a locked condition.

FIGS. 13-14 illustrate a tourniquet 400 for use in the present invention. Tourniquet 400 is used to temporarily hold the cuff 18 of graft 10 in an appropriate position within the exposed aorta so that a stapling operation may be performed. It will be appreciated, however, that tourniquet 400 may be used in any surgical procedure where there is a need to place a clamp around a tubular or cylindrical structure.

Tourniquet 400 has a generally straight hollow shaft 402 with a handle 404 provided at a proximal end thereof. A button 406 is mounted in handle 404 for sliding movement in an axial direction along an elongated slot 408. Within handle 404, button 406 is connected to the proximal end of an elongated rod 410, which is arranged for sliding movement within shaft 402.

At its distal end, shaft 402 is enclosed by an end plug 412 having a through slot 414. Through slot 414 is sized to slidably receive an elongated flexible band 416. At one end, band 416 is fixedly connected to the distal end of rod 410, such as by a screw 417 or any other conventional connecting technique. At its other end, band 416 has a rounded tip 418 and opposed notches 420 defining a narrowed neck spaced from tip 418, the purpose of which will be described below. Band 416 preferably is wider than it is thick so as to define a rectangular cross-section that will hold an annular shape better than the round cross-section of a conventional suture. Band 416 may be formed from any material having sufficient flexibility to conform smoothly around loading unit 100, graft 10 and the aorta, and sufficient tensile strength to securely hold graft 10 and the aorta in overlapping relationship during a stapling operation. In that regard, particularly preferred materials for forming band 416 are nitinol or other shape memory materials, polypropylene, polyethylene, Mylar™ polyester, nylon and other suitable materials. Nitinol or other shape memory materials are particularly preferred since they permit band 416 to be preformed with a curvature that will facilitate the maneuvering of band 416 around the graft and artery.

A retaining block 422 is assembled in the distal end of shaft 402 for sliding movement in the axial direction between end plug 412 and one or more tangs 424 bent inwardly from shaft 402. A spring 426 disposed between retaining block 422 and end plug 412 biases the retaining block in the proximal direction against tangs 424.

Retaining block 422 has an axial bore 428, which is sized and shaped to receive the rounded tip 418 of band 416. Below bore 428, retaining block 422 has an axial slot 430 aligned with the through slot 414 in end plug 412 and sized and shaped to receive band 415 for sliding movement relative to the retaining block. The upper wall 432 of retaining block 422 has an axial slot 434, which extends the length of the retaining block and communicates with axial bore 428. A keyhole 436 is formed in the upper wall 432 of retaining block 422 in a direction transverse to slot 434. Keyhole 436 is sized to receive tip 418 of band 416 and to permit its insertion into axial bore 428.

To operate tourniquet 400, button 405 is initially pushed in the distal direction to deploy band 416 through the slot 414 in end plug 412. When formed from a shape memory material, band 416 will form a curved shape so that tip 418 will approach the distal end of shaft 402. When not formed from a shape memory material, band 416 may be manually manipulated to place tip 418 near the distal end of shaft 402.

Tourniquet 400 may then be operated to capture the tip 418 of band 416. More particularly, button 406 may be pushed further in the distal direction so that the distal end of rod 410 contacts retaining block 422. Further movement of button 406 in the distal direction will cause rod 410 to push retaining block 422 in the distal direction against the biasing force of spring 425 until the keyhole 436 in retaining block 422 is aligned with an aperture 438 in shaft 402. At this point, tip 418 of band 416 may be inserted through aperture 438 and keyhole 436 until the tip resides within the axial bore 428 in retaining block 422 and notches 420 are aligned with the slot 434 in the upper wall 432 of the retaining block. As button 406 is released, the biasing force of spring 426 will push retaining block 422 proximally, whereupon notches 420 will reside in slot 434, keyhole 436 will no longer be aligned with aperture 438, and tip 418 will be captured within the bore 428 in the retaining block.

To tighten band 416 around loading unit 100, graft 10 and the aorta, button 406 is moved in the proximal direction so as to draw band 416 into shaft 402. As button 406 is retracted, a plurality of teeth (not shown) provided on button 406 may engage with a similar plurality of teeth (not shown) provided on handle 404. The engagement of the teeth on these respective components may act as a ratchet mechanism enabling button 406 to be retracted, but blocking it from movement relative to handle 404 in the distal direction. Therefore, as band 416 is progressively tightened, it will be locked in place and prevented from loosening at each step in the tightening process. The teeth on the respective components may be biased into engagement with one another by a spring (not shown) interposed between button 405 and handle 404. Thus, by depressing button 406 to overcome the biasing force of the spring, the teeth may be separated from one another so that button 406 may be moved distally to release band 416.

Stapling Instrument

One embodiment of a stapling instrument 500 which attaches to loading unit 100 and is operable to actuate a stapling procedure, is illustrated in FIGS. 15-22. Instrument 500 includes a hollow outer shaft 502 having a substantially straight elongated portion 504 and a smoothly curved distal and portion 506 which terminates at an angle relative to elongated portion 504. End portion 506 may terminate at an angle of between about 90° and about 180° relative to elongated portion 504. Preferably, end portion 506 terminates an angle of between about 105° and about 125° relative to elongated portion 504, with an angle of about 115° being most preferred. An anvil assembly 510 is provided at the distal end of shaft 502, while a handle 512 is provided at the proximal end thereof. Optionally, a bushing 508 having a flange 509 at a proximal end thereof may be assembled over a reduced diameter portion at the proximal end of outer shaft 502 and held in place thereon by a retaining ring 507 so as to be rotatable relative to the shaft. Handle 512 may be assembled to shaft 502 by capturing flange 509 between handle portions 511 and 513 when they are assembled together. By connecting handle 512 to bushing 508, the handle is able to rotate without binding relative to the remainder of instrument 500, and therefore may be maneuvered by the surgeon to an appropriate position to effect a stapling procedure.

Figure 16:
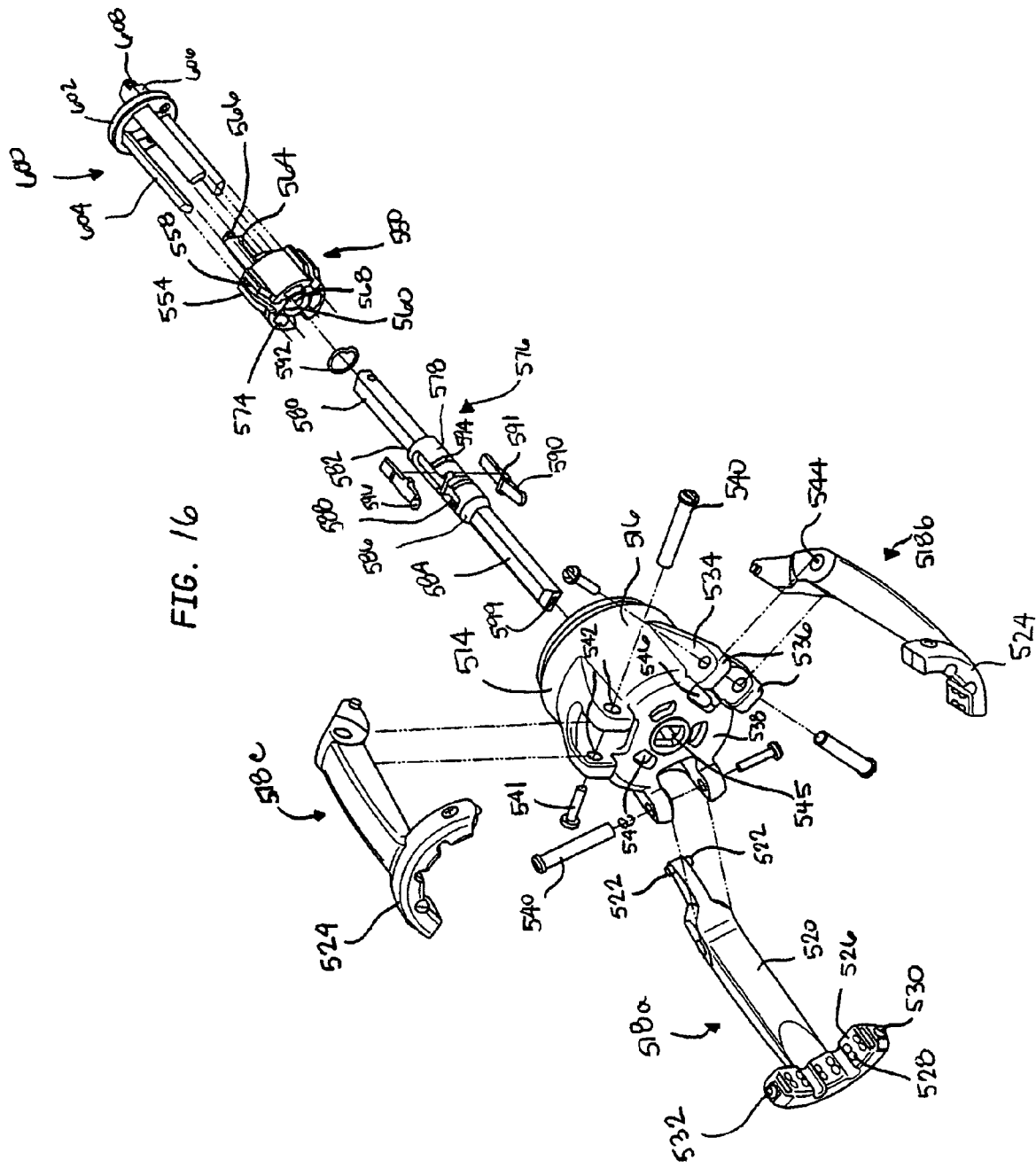
FIG. 16 is a front perspective exploded view of the head of the surgical stapling instrument shown in FIG. 15.
Figure 17:
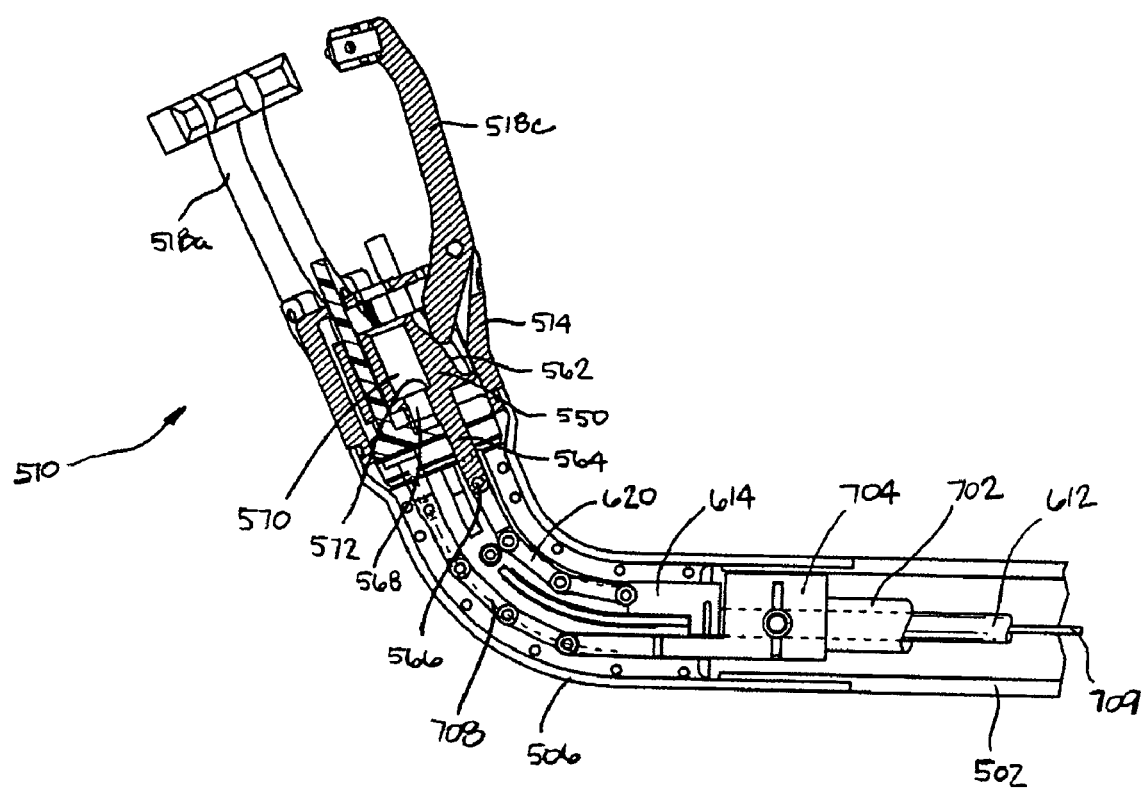
FIG. 17 is a longitudinal cross-sectional view of the head of the surgical stapling instrument with the anvils in the open condition.

Referring specifically to FIG. 16, anvil assembly 510 includes a generally hollow anvil hub 514 having a cylindrical side wall 516 to which right anvil 518a, left anvil 518b, and center anvil 518c are pivotably mounted. Each anvil includes an elongated arm 520 having a dog-leg configuration with a pair of laterally projecting guide pins 522 at the proximal end thereof and an arcuate-shaped bracket 524 at the distal end thereof. An anvil insert 526 having a plurality of spaced staple returns 528 may be mounted to each bracket 524. Instrument 500 has a total of twenty staple returns 528, six each on right anvil 518a and left anvil 518b, and eight on center anvil 518c, which has a bracket 524 with a slightly larger arcuate length. Each staple return has depressions for guiding the free ends of a staple 150 into a bent configuration. Alternatively, staple return 528 may be formed directly in brackets 524.

The brackets 524 on the ends of anvils 518a, 518b and 518c each define an arc such that, in the closed position of anvil assembly 510, these brackets collectively define a complete circle. Each bracket 524 includes a male locating member 530 at one end thereof and a female locating member 532 at the opposite end thereof, the male and female locating members on adjacent brackets 524 engaging with one another in the closed position of anvil assembly 510 so as to properly locate and align staple returns 528 relative to one another.

Figure 19:
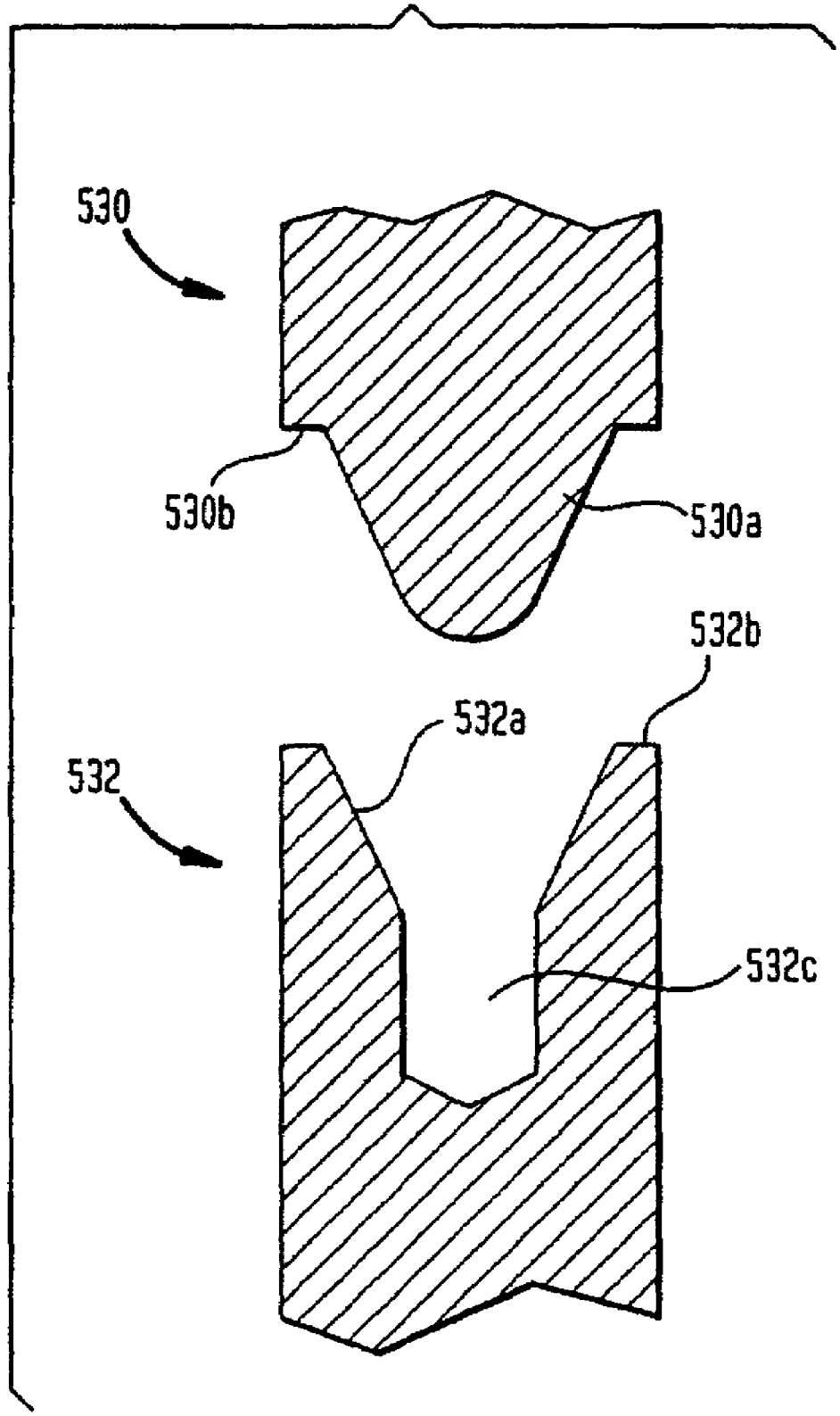
FIG. 19 is an enlarged cross-sectional view showing the male and female anvil locating members.

In a preferred embodiment hereof shown in FIG. 19, male locating member 530 may have a conical portion 530a with a rounded tip and a substantially flat ring 530b formed around its base. Female locating member 532 may have a tapered recess 532a shaped to mate with the tapered walls of portion 530a, and a substantially flat ring 532b formed around recess 532a. An extended bore 532c may be formed at the bottom of recess 532a. When anvil assembly 510 is closed, conical portion 530a fits within recess 532a and surfaces 530b and 532b are pressed tightly against one another. The small area of surfaces 530b and 532b, combined with the high compressive force developed on the closing of the anvils, cause any tissue which may be captured between surfaces 530b and 532b to be pulverized. Furthermore, any miscellaneous tissue, which may be captured between conical portion 530a and tapered recess 532a upon the closing of anvil assembly 510, may be pushed into the extended bore 532c at the bottom of recess 532a. Hence, this structure of male locating member 530 and female locating member 532 helps assure that anvils 518a, 518b and 518c achieve a fully closed condition and are not prevented from doing so by any extraneous tissue which may be present during the surgical procedure.

Anvils 518a, 518b, and 518c are pivotably mounted to anvil hub 514 by a series of yokes 534 formed at spaced distances on the outer surface of side wall 516. Each yoke 534 includes a pair of supports 536 which project beyond the distal end 538 of anvil hub 514, and which are spaced apart so as to receive one of anvil arms 520 therebetween. A barrel nut 540 may be inserted through a pair of axially aligned apertures 542 formed in supports 536 and through an aperture 544 provided at the dog leg in an anvil arm 520 and mate with a screw 541 for holding the anvil in assembled relationship to anvil hub 514. Alternatively, anvils 518 may be held to yokes 534 through any other technique allowing pivoting of the anvil arms, such as through a pivot pin or the threaded engagement of one end of a shoulder bolt with threads formed in one of apertures 542. Access openings 546 are formed in side wall 516 in the spaces between each pair of supports 536 in a yoke 534, the access openings continuing radially inward by a predetermined amount in the distal end 538 of anvil hub 514. Access openings 546 enable the proximal ends of anvil arms 520 to project into the interior of anvil hub 514 and provide clearance for the movement of anvils 518 between open and closed positions. The distal end 538 of anvil hub 514 includes a central aperture 545 having curved top and bottom surfaces and flat side surfaces, and a series of apertures 548 arranged substantially symmetrically around central aperture 545 for slidably receiving the fingers of a pusher 600, the purpose of which will be described below.

A cam element 550 is slidably assembled in the open proximal end of anvil hub 514. Cam element 550 has a generally cylindrical structure with a series of ribs 554 projecting radially outward therefrom. Ribs 554 are oriented in the axial direction of anvil assembly 510 and engage in similarly oriented channels (not shown) formed in the interior of anvil hub 514. Each channel is positioned so as to be radially inward of a corresponding yoke 534.

Ribs 554 are formed with a central slot 558 having a width sufficient to receive the proximal end of an anvil arm 520, and an undercut 560 on each side of the slot for receiving the guide pins 522 on anvils 518. The bottom surface of each slot 558, including undercut portions 560, defines a tapered cam surface 562 so that axial movement of cam element 550 relative to anvil hub 514 causes anvils 518 to move between the open and closed positions. An arm 564 projects axially from the proximal end of cam element 550. Arm 564 has a transverse aperture 566 at its free end for connection to a drive mechanism for effecting axial movement of cam element 550, as will be explained below.

Cam element 550 includes a central bore 568 having flat top and bottom surfaces and curved side surfaces, and a generally cylindrical counterbore 570 extending inwardly from the distal end of the cam element to an end wall 572. A series of through openings 574, similar in size and shape to apertures 548 in anvil hub 514, are arranged substantially symmetrically around central opening 568 for slidably receiving the fingers of pusher 600.

An anvil hub shaft 576 is mounted in anvil assembly 510 between anvil hub 514 and cam element 550. Shaft 576 has a large intermediate portion 578 having a substantially cylindrical cross-section, and a proximal end portion 580, which is smaller in cross-section so as to define a step 582 therebetween. Similarly, shaft 576 has a distal end portion 584, which is smaller in cross-section than intermediate portion 578 so as to define a step 586 therebetween. The intermediate portion 578 of shaft 576 has similar recesses 588 formed in its upper and lower surfaces, each of which is sized and shaped to receive a catch member 590. Catch members 590 have a protruding transverse rib 591 so that the catch members rest in recesses 588 in a see-saw fashion. A spring catch 592 in the form of a split ring may be assembled in an annular groove 594 formed by the circumferential alignment of groove portions in the intermediate portion 578 of shaft 576 and in each of catch members 590. The assembly of spring catch 592 around the catch members 590 and the intermediate portion 578 of shaft 576 holds the catch members in assembled relationship to shaft 576 so that the distal ends of the catch members are biased outwardly, while permitting the distal ends of the catch members to pivot inwardly upon the application of a radially inward compressive force thereto. At their distal ends, catch members 590 each have a radially projecting prong 596 having a sharply tapered distal surface and a slightly tapered proximal catch surface. Prongs 596 secure loading unit 100 to instrument 500, as will be explained below.

The distal end portion 584 of shaft 576 has a shape similar to that of the elongated finger 320 at the end of wand 300. That is, the distal end portion 584 of shaft 576 has flat side and lower surfaces and a curved upper surface for mating engagement within shaft 180 of loading unit 100. An axial bore 599 is provided along the length of shaft 576 for receiving guidewire 250, as will be explained below.

Shaft 576 is assembled in anvil hub 514 so that the distal end portion 584 of shaft 576 extends through the central aperture 545 in the anvil hub, with step 586 abutting the inside wall of the distal end 538 of the anvil hub adjacent aperture 545. The shape of the aperture 545 in anvil hub 514 assures that the anvil hub is assembled in the proper orientation on shaft 576 and is unable to rotate once assembled thereon. In this assembled position, the distal end portion 584 of shaft 576 extends outwardly from anvil hub 514, as do the radially projecting prongs 596 on catch members 590.

Cam element 550 is assembled in anvil hub 514 so as to capture the intermediate portion 578 of shaft 576 therebetween. That is, cam element 550 is assembled over the proximal end portion 580 of shaft 576 until the end wall 572 of counterbore 570 is engaged with step 582 on shaft 576. The corresponding shapes of the proximal end portion 580 of shaft corresponding shapes of the proximal end portion 580 of shaft 576 and the central bore 568 in cam element 550 assures that these elements are assembled in the proper orientation and that the cam element is unable to rotate once assembled on the shaft.

A pusher 600 having a disk-shaped base member 602 and a plurality of axially extending fingers 604 is assembled in anvil assembly 510 so that fingers 604 extend through openings 574 in cam element 550 and apertures 548 in anvil hub 514. Fingers 604 are of a sufficient length that when pusher 600 is displaced fully in the distal direction, the free ends of fingers 604 protrude outwardly from the distal end 538 of anvil hub 514 and into a loading unit 100 mounted on instrument 500. As will be explained below, pusher 600 acts on actuator 170 to deploy staples 150 during a stapling operation. A link 606 having a transverse aperture 608 is connected to the proximal end of base member 602 for joining pusher 600 to a drive mechanism for effecting axial movement of the pusher.

Anvils 518 may be moved between the open and closed positions by an adjustment knob 610 provided at the handle end of instrument 500. Adjustment knob 610 actuates a drive mechanism that transfers rotational movement of knob 610 into axial movement of cam element 550, thereby displacing anvils 518. Referring to FIGS. 17-22, the drive mechanism may include an elongated tube 612 slidably disposed within the hollow shaft 502 of instrument 500. At its distal end, tube 612 may be connected to a link coupler 614 using any conventional arrangement. In a preferred arrangement, the distal end of tube 612 fits within a bore formed in the proximal end of link coupler 614. These elements may be held together by an suitable means, including by sliding a retaining ring (not shown) into a slot 616 formed transversely in link coupler 614 and engaging it in an annular groove formed adjacent to the distal end of tube 612.

Link coupler 614 may be joined to arm 564 on cam element 550 by a plurality of links 620. A pair of track inserts 622 assembled in the opposite sides of curved distal end portion 506 of shaft 502 may define first and second pairs of laterally spaced guide tracks 624 and 626. Links 620 may ride in guide tracks 626 so that any axial movement of tube 612 is transferred along the curved portion of shaft 502 to cam element 550. Links 620 may take any form capable of transmitting the compressive force exerted by tube 612 and link coupler 614 to cam element 550 as anvil assembly 510 is placed in a closed condition, and capable of transmitting the tensile force from tube 612 and link coupler 614 to cam element 550 as tube 612 is retracted to place anvil assembly 510 in an open condition. Thus, links 620 may consist of individual links joined together in a conventional fashion, or may be in the form of a solid band having periodic thinned sections defining a plurality of living hinges. Alternatively, links 620 may not be links at all, but may be a solid band having the requisite compressive and tensile strength, while at the same time having sufficient flexibility to bend smoothly and uniformly along the curved portion of shaft 502.

At its proximal end, tube 612 may be connected to a coupling element 628. In a preferred embodiment, the proximal end of tube 612 may be inserted into a bore formed in the distal end of coupling element 628, and these elements may be held together in the same manner as tube 612 and link coupler 614, that is, by sliding a retaining ring (not shown) into a slot 630 formed transversely in coupling element 628 and engaging it in an annular groove formed adjacent to the proximal end of tube 612. Alternatively, the distal end of tube 612 may be joined to link coupler 614 and the proximal end of tube 612 may be joined to coupling element 628 by any other known connection techniques. Coupling element 628 may have a pair of elongated bosses (not shown) extending in the axial direction on either side of the coupling element. Each of the bosses may be slidably held in an elongated slot provided in each of handle portions 511 and 513. The elongated slots have a predetermined length so as to define the extent of axial travel of coupling element 628.

At its proximal end, coupling element 628 may be threadedly engaged with a shaft 642. Shaft 642 has a stepped structure so as to define an intermediate portion 644, which is smaller in diameter than a threaded distal portion 646 and larger in diameter than a proximal portion 648. A bushing 650 may be assembled over intermediate portion 644 and may be held in place by the step between the intermediate portion 644 and distal portion 646 of shaft 642 and a retaining ring 652 assembled in an annular groove formed in the intermediate portion 644 proximally of the bushing. The outer circumference of bushing 650 may be formed with an annular groove 654, which enables the bushing to be captured in a circular opening formed in the proximal end of handle 512 when handle portions 511 and 513 are assembled together.

Adjustment knob 610 has an internal elongated annular boss 656 for receiving the proximal portion 648 of shaft 642. A pair of diametrically opposed teeth 658 formed on the free end of boss 656 may engage recesses 660 formed in the intermediate portion 644 of shaft 642 so that any rotational movement of knob 610 results in a corresponding rotation of shaft 642. A barrel nut 662 engages a threaded portion 664 formed on the proximal portion 648 of shaft 642 so as to hold knob 610 in assembled relationship to the shaft. Barrel nut 662 resides in a counterbore 666 formed in the proximal end of knob 610 so that it does protrude outwardly from the knob.

Optionally, a conventional clutch mechanism (not shown) may be provided between knob 610 and shaft 642 to prevent the overloading of anvil assembly 510. Thus, once a threshold to the further closure of anvils 518a, 518b and 518c has been met (either because the anvils are fully closed or because there is interfering tissue), the clutch mechanism will enable knob 610 to rotate without further movement of the anvils, thereby preventing damage to instrument 500 or damage to tissue from the closing anvils.

Figure 20A:
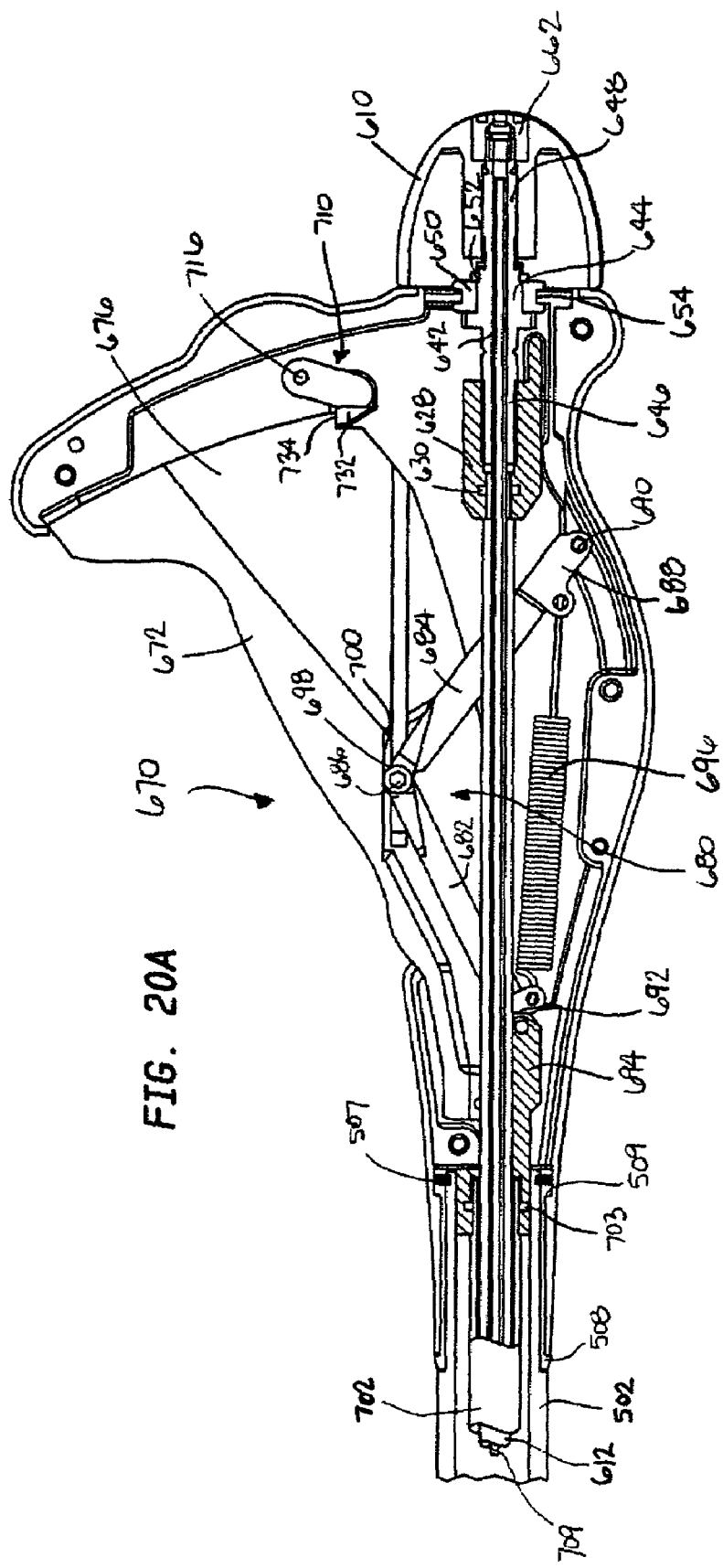
FIG. 20A is a longitudinal cross-sectional view of one embodiment of the actuating handle of the surgical stapling instrument in a condition in which the anvils are in the open condition and the stapling mechanism is not actuated.
Figure 21A:
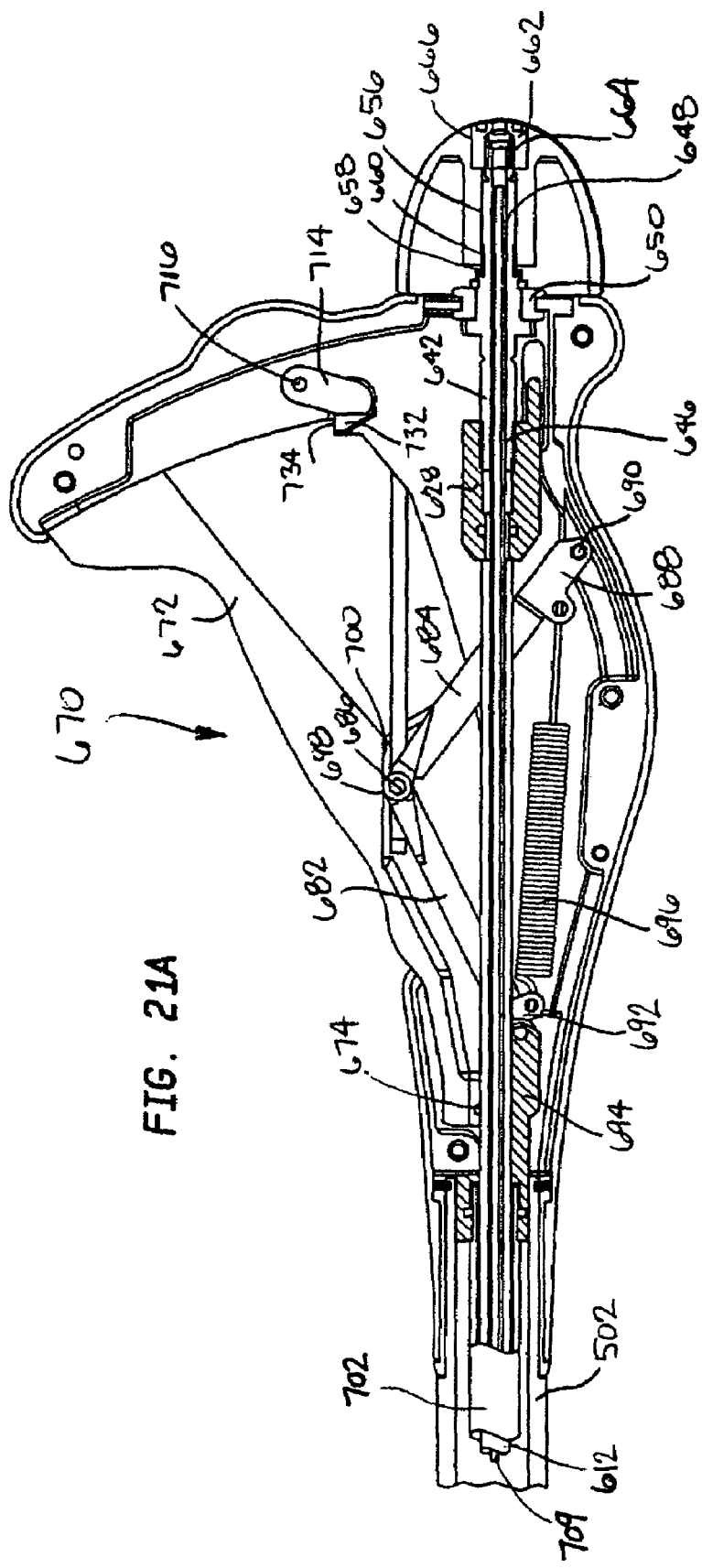
FIG. 21A is a longitudinal cross-sectional view of the actuating handle of FIG. 20A in a condition in which the anvils are in the closed condition and the stapling mechanism is not actuated.
Figure 21B:
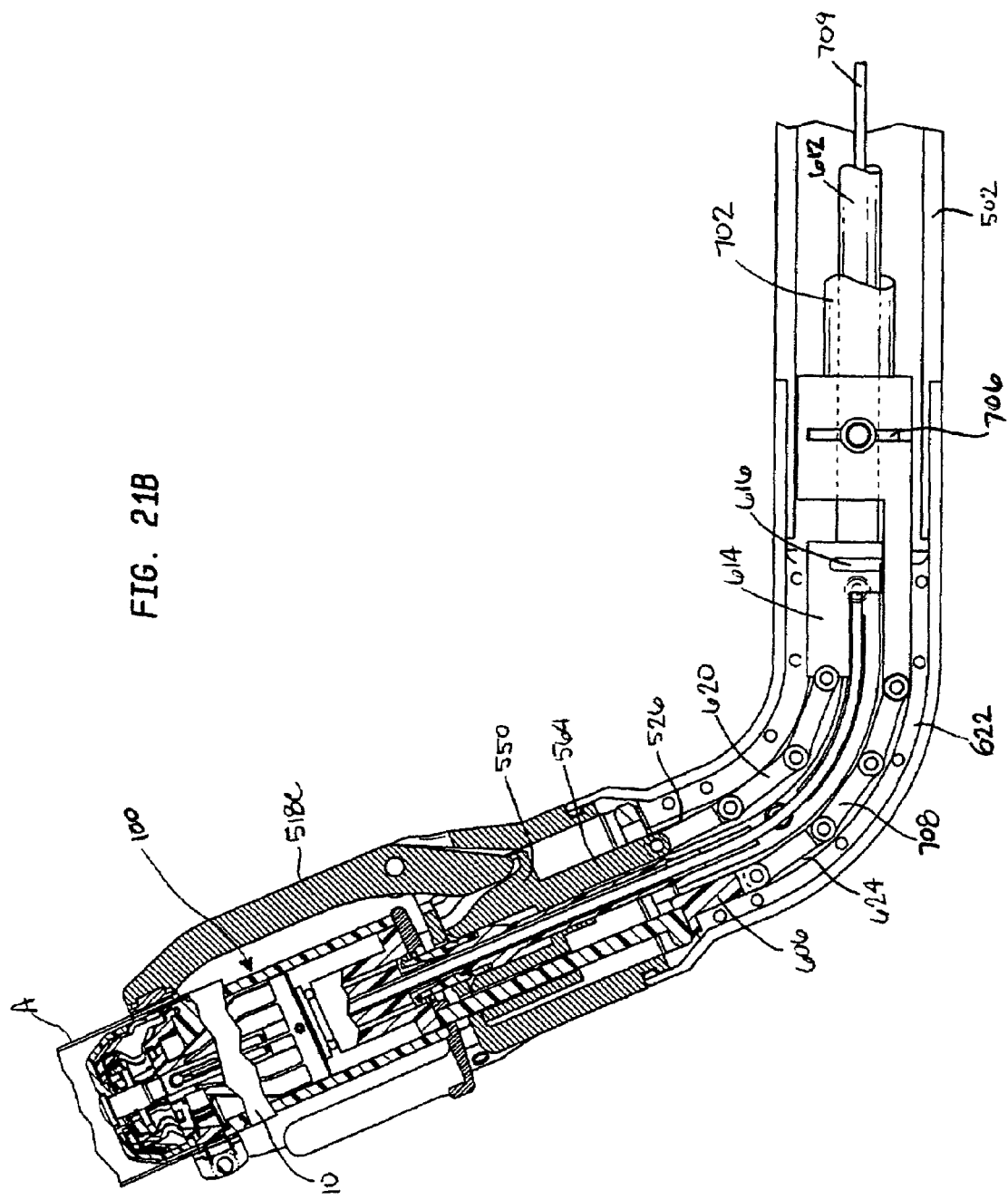
FIG. 21B is the same view as FIG. 20B, but showing the anvils of the surgical stapling instrument in the closed condition.
Figure 22A:
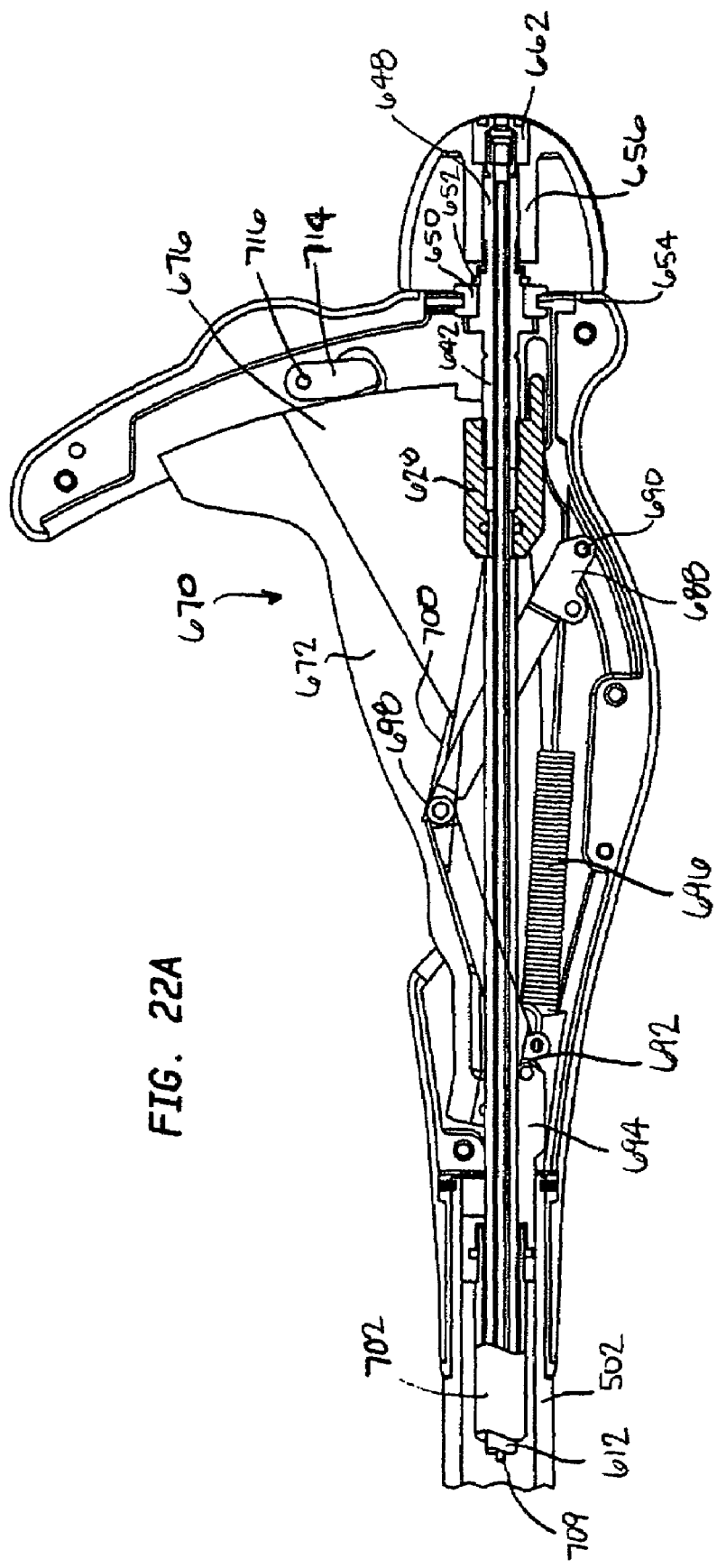
FIG. 22A is a longitudinal cross-sectional view of the actuating handle of FIG. 20A in a condition in which the anvils are in the closed condition and the stapling mechanism has been actuated.
Figure 22B:
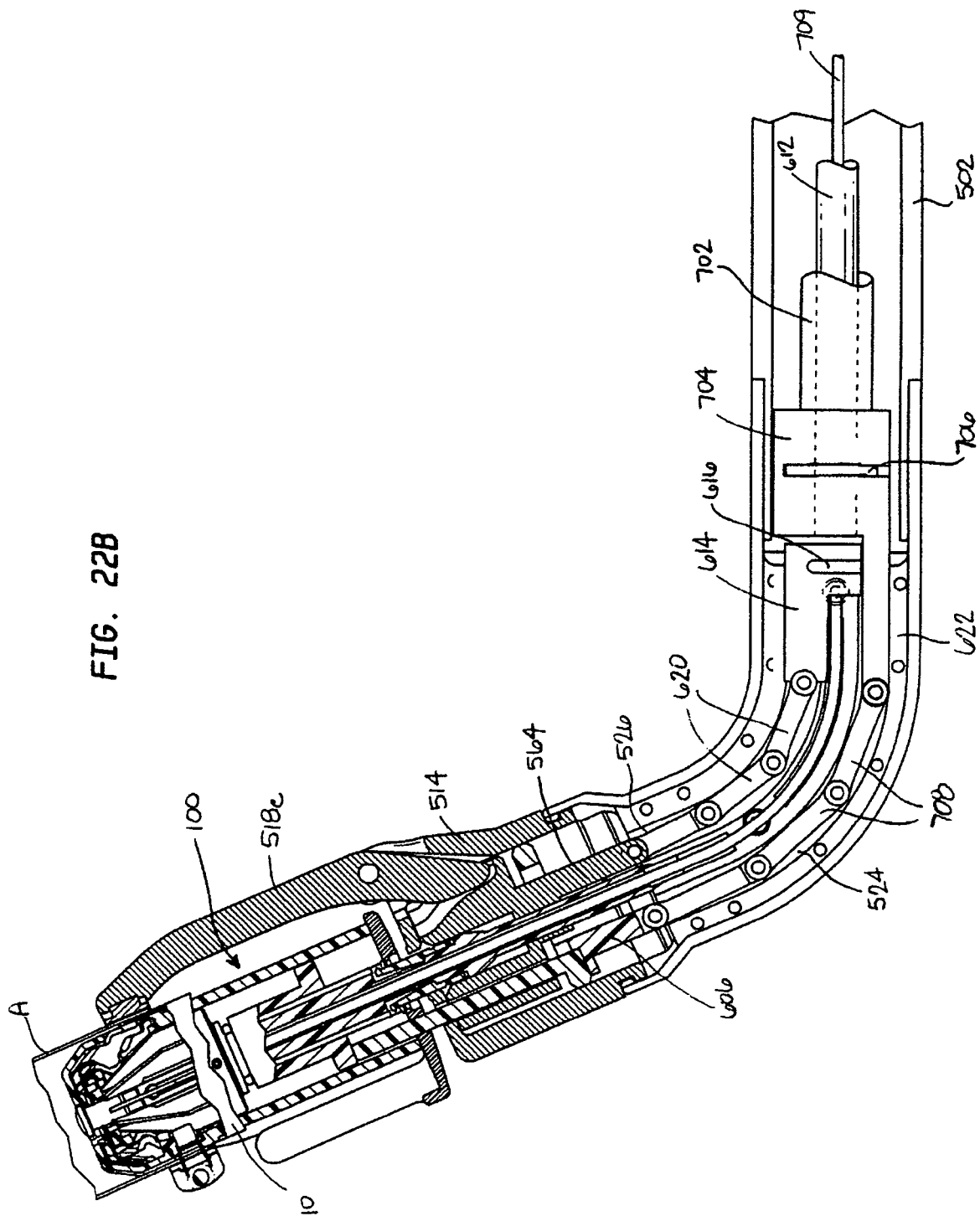
FIG. 22B is the same view as FIG. 20B, but showing the loading unit in the position following staple deployment.

Handle 512 of instrument 500 is further provided with a trigger mechanism 670 for actuating a stapling operation. Referring to FIGS. 20A, 21A and 22A, trigger mechanism 670 may include a trigger 672 pivotably mounted between handle portions 511 and 513 by a pivot pin 674. Trigger 672 has a generally hollow, molded construction including a pair of spaced side walls 676. Trigger mechanism 670 may further include a linkage assembly 680 including a pair of links 682 and 684 joined together by a pivot pin 686. One end 688 of linkage assembly 680 is pivotably held in a fixed position between handle portions 511 and 513 by a pivot pin 690. The opposite end 692 of linkage assembly 680 is pivotably joined to a coupling element 694. A spring 696 connected between links 682 and 684 bias linkage assembly 680 to the rest position shown in FIG. 20A. In this rest position, the distal end of link 682 is relatively close to the proximal end of link 684, such that the links form a relatively small angle therebetween. Furthermore, an apex 698 defined at the connection of link 682 to link 684 is biased against an engagement surface 700 formed between the side walls 676 of trigger 672.

An elongated tube 702 slidably disposed within outer shaft 502 of instrument 500 and over tube 612 may be connected at its proximal end to coupling element 694. More particularly, the proximal end of tube 702 may be inserted in a bore formed in the distal end of coupling element 694. This assembly may be maintained in the same manner as the assembly of tube 612 to link coupler 614, that is, by sliding a retaining ring (not shown) into a slot 703 formed transversely in coupling element 694 and engaging it in an annular groove formed adjacent to the proximal end of tube 702. At its distal end, tube 702 may be connected to a coupling link 704. In a preferred arrangement, the distal end of tube 702 may be inserted in a bore formed in the proximal end of coupling link 704 and may be held in assembled relationship therein in the same fashion as the other tube/coupler connections described above, namely, by sliding a retaining ring (not shown) into a slot 706 formed transversely in coupling link 704 and engaging it in an annular groove formed adjacent to the distal end of tube 702. Alternatively, any other known connection techniques may be used both to join the distal end of tube 702 to coupling link 704, and to join the proximal end of tube 702 to coupling element 694. Coupling link 704 preferably is assembled over tube 612 and proximally of link coupler 614 so as to not interfere with the axial movement thereof, and may be joined to link 606 on pusher 600 by a plurality of links 708. Links 708 may ride in laterally spaced guide tracks 624 formed in track inserts 622 so that any axial movement of tube 702 is transferred along the curved portion of shaft 502 to pusher 600. Links 708 may have any of the structures described above in connection with links 620. Moreover, links 708 may have the same structure as links 620 or a structure different therefrom.

As will be appreciated from the foregoing description, trigger mechanism 670 may be actuated by pressing trigger 672 toward handle 512. This movement of trigger 672 will cause engagement surface 700 to push against the apex 698 of linkage assembly 680, thereby causing the angle between links 682 and 684 to be increased against the biasing force of spring 696. Since the end 688 of linkage assembly 680 is fixed relative to handle 512, the increased angle between links 682 and 684 will cause the other end 692 of linkage assembly 680 to move axially in the distal direction. This axial movement will be transferred through coupling element 694, tube 702, coupling link 704, and links 708 to pusher 600, resulting in the movement of the fingers 604 of the pusher into loading unit 100, and the resultant deployment of staples 150. Following the deployment of staples 150, the biasing force of spring 696 will cause trigger 672 to return to its rest position as the compressive force is released therefrom.

Instrument 500 may further include a guidewire tube 709, which is positioned within tube 612. At its distal end, guidewire tube 709 protrudes out from tube 612 and has a curved portion whose distal end is inserted in a counterbore formed in the proximal end of anvil hub shaft 576. At its proximal end, guidewire tube 709 extends out from tube 612, through coupling element 628 and into shaft 642. Guidewire tube 709 provides an uninterrupted channel for guidewire 250 from loading unit 100 through instrument 500.

To prevent the premature accidental deployment of staples 150, trigger mechanism 670 may be provided with a safety 710. Safety 710 may be in the form of an elongated pin (not shown) having a radially projecting tab 714 formed with an aperture 716. A shaft (not shown) may be inserted through aperture 716 to mount safety 710 for sliding movement in a transverse direction between handle portions 511 and 513. A first spring (not shown) mounted on the shaft between tab 714 and handle portion 511, and a second spring (not shown) mounted on the shaft between tab 714 and handle portion 513 bias safety 710 to a rest position which is in a substantially central location between the handle portions. In this rest position, one end of the elongated pin projects outwardly through an aperture in handle portion 511 to define a first button, and the other end of the elongated pin projects outwardly through an aperture in handle portion 513 to define a second button. With the ends of the elongated pin and the shaft constrained from movement by handle portions 511 and 513, safety 710 is prevented from moving pivotably relative to handle 512, but is free to move transversely with respect to the handle. Safety 710 further includes a pair of tangs 732, which, in the rest position of the safety, align with and engage notches 734 formed in the side walls 676, respectively, of trigger 672. Such engagement prevents trigger 672 from being depressed to actuate a stapling operation. Pressing either the first or the second button toward handle 512 moves tangs 732 out of alignment with side walls 676 of trigger 672, thereby clearing the path for the trigger to be depressed relative to handle 512 so that a stapling operation can be performed.

Figure 23:
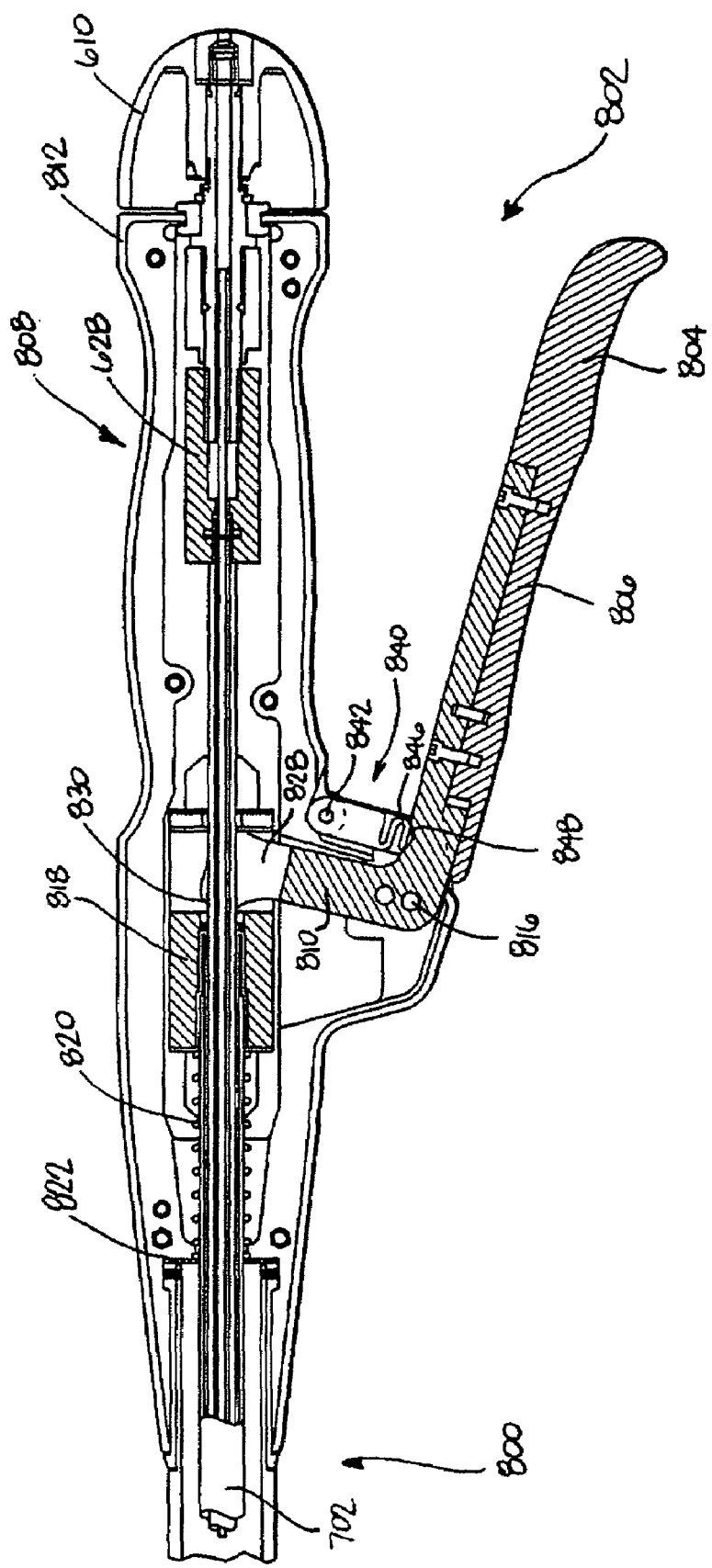
FIG. 23 is a longitudinal cross-sectional view of another embodiment of the actuating handle of the surgical stapling instrument in a condition in which the anvils are in the open condition and the stapling mechanism is not actuated.
Figure 24:
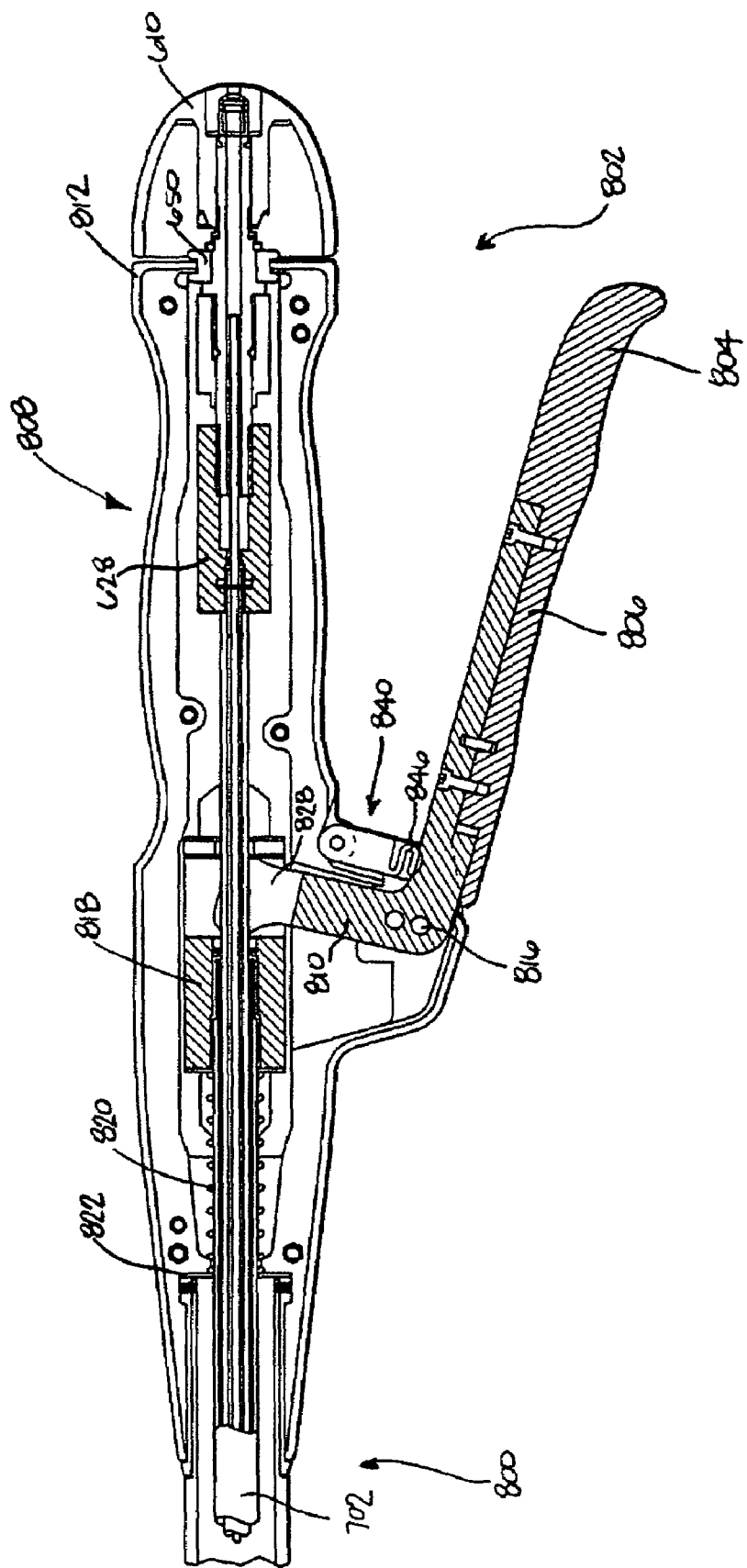
FIG. 24 is a longitudinal cross-sectional view of the actuating handle of FIG. 23 in a condition in which the anvils are in the closed condition and the stapling mechanism is not actuated.
Figure 25:
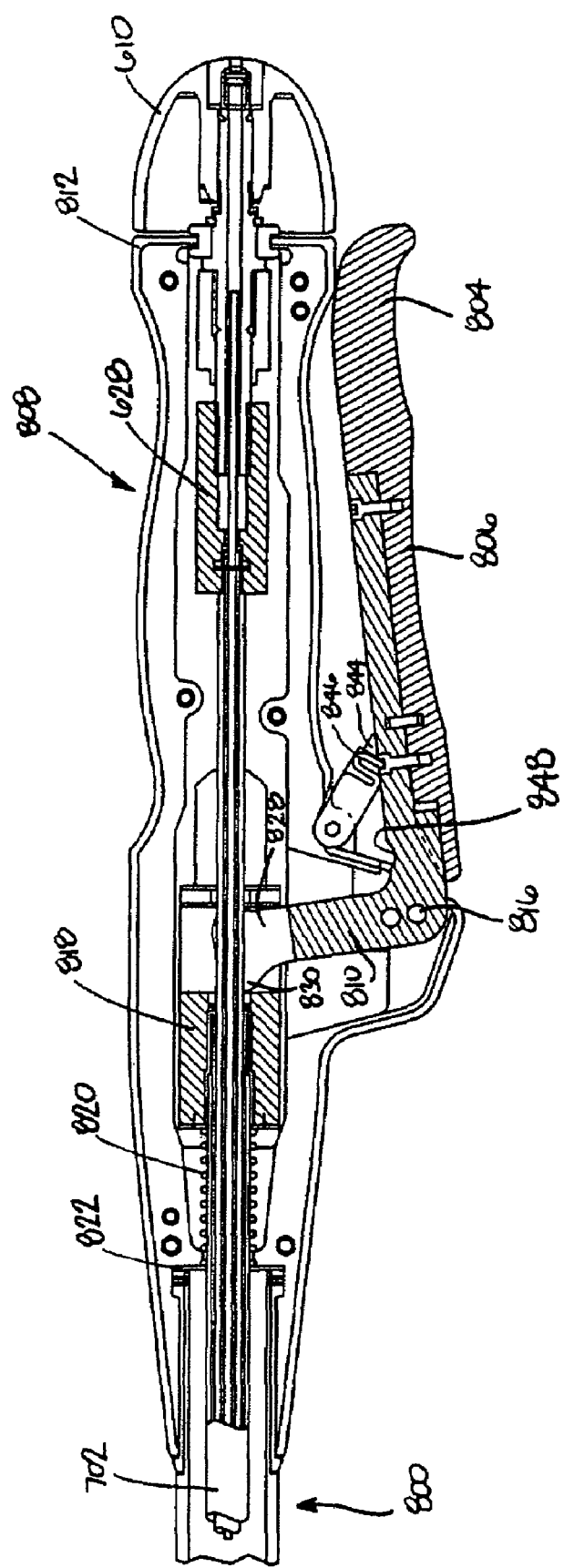
FIG. 25 is a longitudinal cross-sectional view of the actuating handle of FIG. 23 in a condition in which the anvils are in the closed condition and the stapling mechanism has been actuated.

A second embodiment of a handle and trigger mechanism for use with a stapling instrument 800 in accordance with the present invention is shown in FIGS. 23-25. Stapling instrument 800 is substantially the same as stapling instrument 500 described above, with the exception of the handle and the trigger mechanism used to actuate a stapling procedure. Thus, referring to FIG. 23, the trigger mechanism 802 of instrument 800 includes a trigger 804 having an elongated grasping portion 806 spaced from handle 808, and a drive portion 810 projecting laterally from one end of the grasping portion so as to define a generally L-shaped configuration. Trigger 804 is mounted between portions 812 of handle 808 for pivoting movement about a pivot pin 816 disposed at the intersection of grasping portion 806 and drive portion 810.

Instrument 800 includes the same tube 702, coupling link 704 and links 708 as instrument 500. However, the structure at the proximal end of tube 702 differs from that in instrument 500. More particularly, the proximal end of tube 702 may be connected to a coupling element 818 in any conventional manner, including that by which tube 612 is connected to coupling element 628 at its proximal end. Coupling element 818 may be assembled on tube 612 for sliding movement in the axial direction of the tube. A biasing spring 820 may be assembled over tube 702 between the distal end of coupling element 818 and an annular surface 822 formed transversely in handle 808. Coupling element 818 may have a pari of elongated bosses (not shown) extending in the axial direction on either side of the coupling element. Each of these bosses may be slidably held in an elongated slot (not shown) provided in each of handle portions 812. The elongated slots have a predetermined length so as to define the extent of axial travel of coupling element 818.

Drive portion 810 of trigger 804 may be formed with a pair of spaced walls 828 at the free end thereof. Each of walls 828 may include a curved cam surface 830 projecting in a distal direction therefrom. In the assembled position of trigger mechanism 802, walls 828 reside on either side of tube 612 with cam surfaces 830 contacting the proximal end of coupling element 818. In the rest position of trigger mechanism 802, shown in FIG. 23, the force exerted by spring 820 biases coupling element 818 in the proximal direction, thereby pivoting the grasping portion 806 of trigger 804 toward handle 808. The counterclockwise movement of trigger 804 (as shown in FIG. 25) will cause the drive portion 810 of the trigger to exert a force on coupling element 818 through cam surfaces 830, driving coupling element 818 in the distal direction against the biasing force of spring 820. This axial movement of coupling element 818 will be transferred through tube 702, coupling link 704 and links 708 to pusher 600, thereby resulting in the deployment of staples 150 as pusher fingers 604 are driven into loading unit 100. Following deployment of staples 150, spring 820 will again bias coupling element 818 proximally to return trigger 804 to its rest position once the compressive force has been released therefrom.

Instrument 800 may further include a safety 840 to prevent the premature accidental deployment of staples 150. Safety 840 may be pivotably connected between handle portions 812 by a pivot pin 842 so that safety 840 is positioned between handle 808 and the grasping portion 806 of trigger 804. At its free end, safety 840 has a recess 804 sized to receive the grasping portion of 806 of trigger 804. Recess 844 may include a resilient member 846 adapted to engage within a shallow recess 848 in grasping portion 806 in the locked condition of trigger mechanism 802. In a preferred embodiment, resilient member 846 may be in the form of an S-shaped member integrally molded with safety 840. Resilient member 846 causes safety 840 to fit tightly between handle 808 and grasping portion 806 in the locked condition. Such engagement prevents trigger 804 from being depressed to actuate a stapling operation. Pivoting safety 840 away from grasping portion 806, however, releases trigger 804 for movement toward handle 808 to actuate a stapling operation.

Sizer

Figure 26:
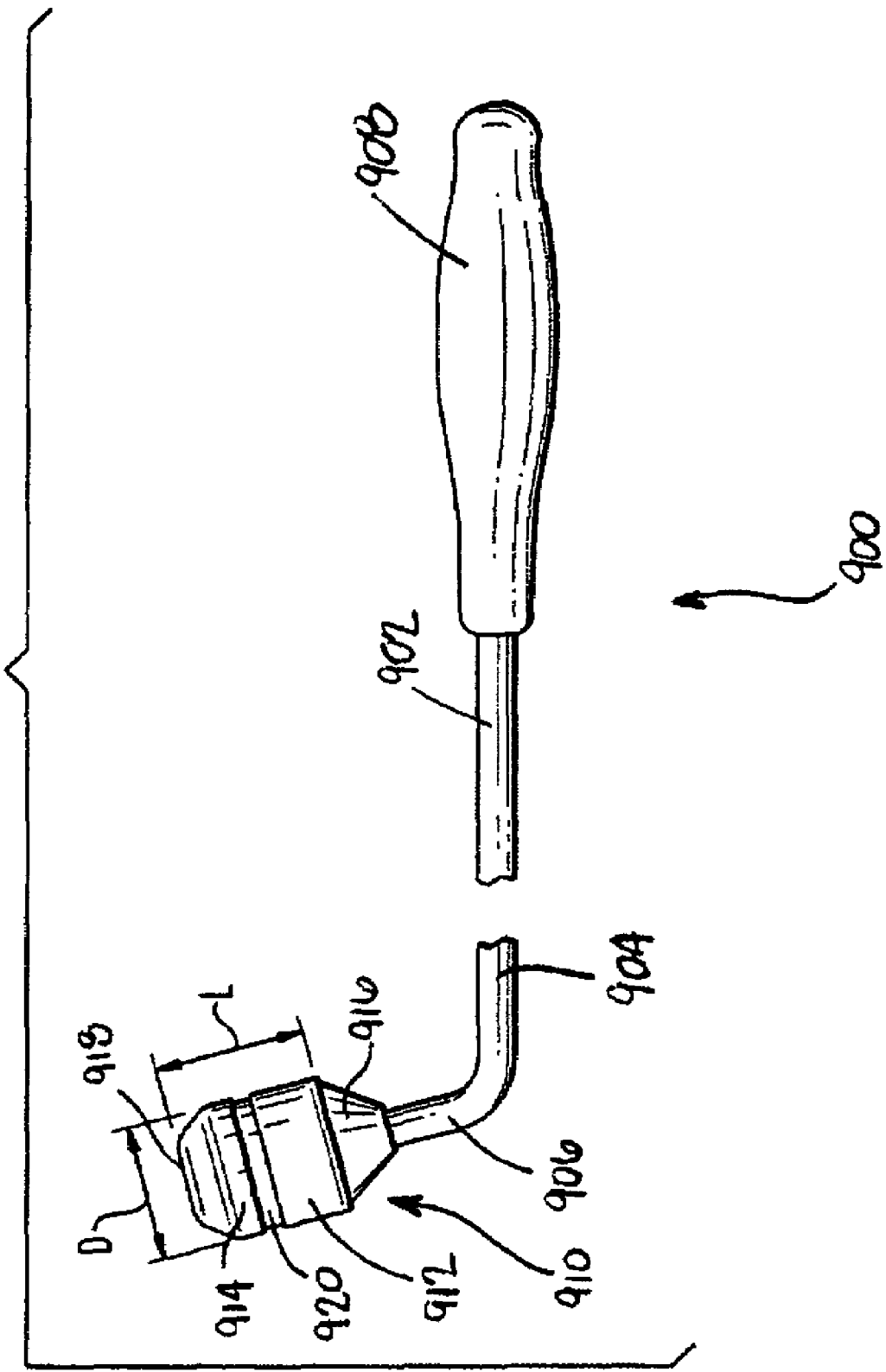
FIG. 26 is an elevational view of a sizer in accordance with the present invention.
Figure 27:
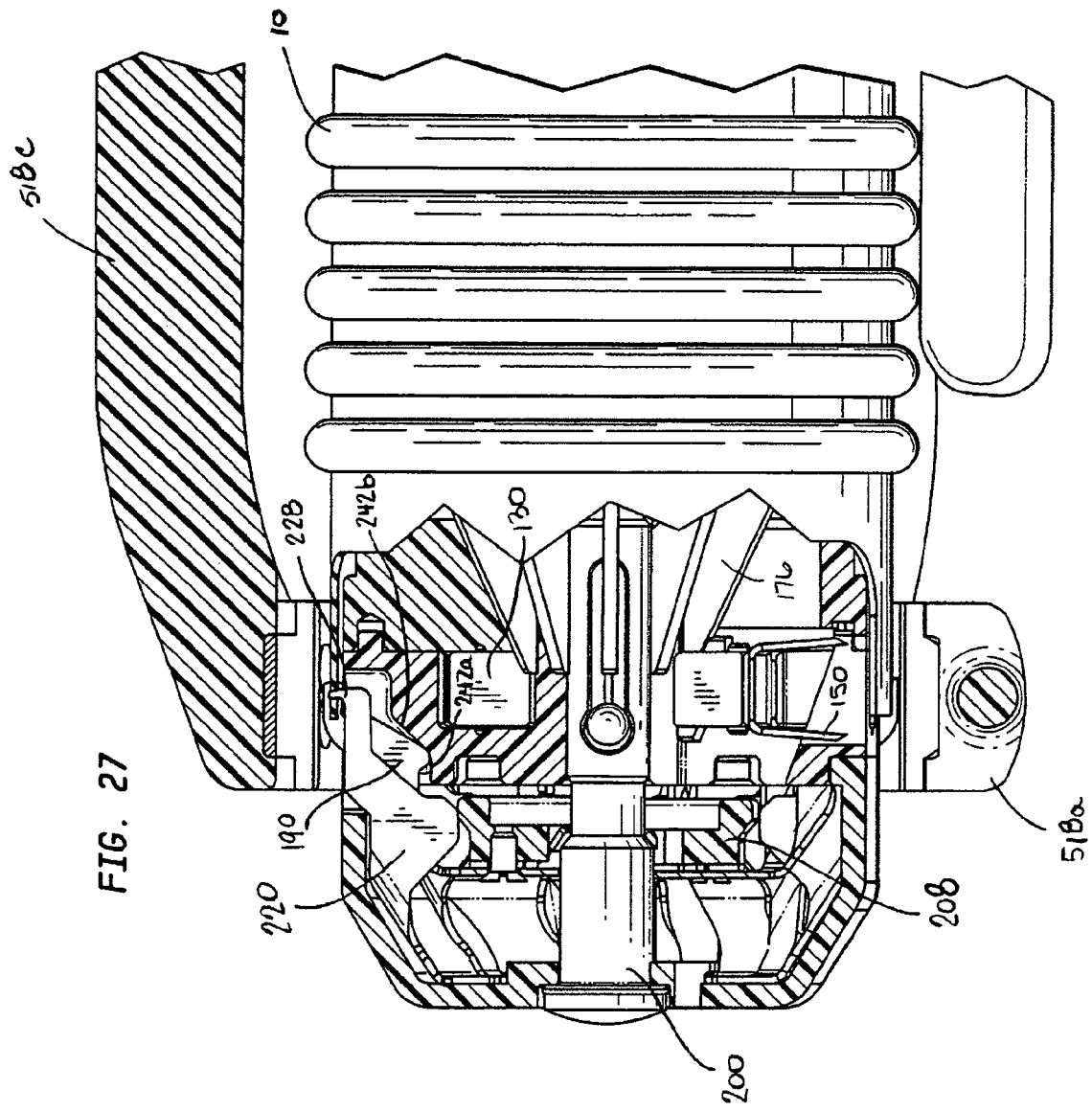
FIG. 27 is a longitudinal cross-sectional view showing the loading unit and a prosthetic graft assembled to the head of the surgical stapling instrument prior to staple deployment.
Figure 28:
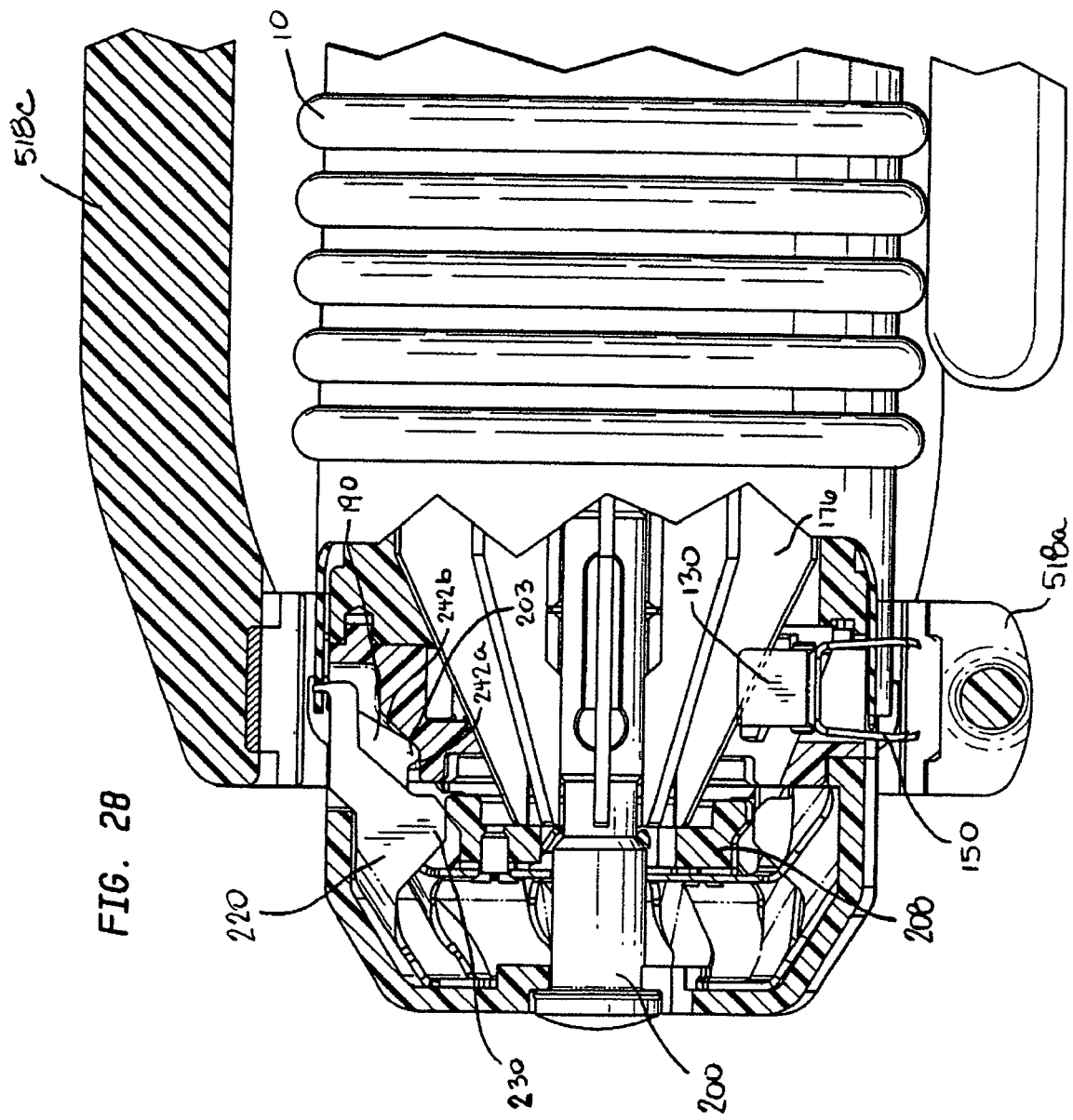
FIG. 28 is the same view as FIG. 26, but showing partial deployment of the staples.

FIG. 26 depicts a sizer 900 for use in the present invention. Sizer 900 has several functions, including (1) measuring the diameter of the aorta so that a graft 10 of a proper size may be connected thereto, (2) assuring that there is an adequate amount of transected aorta between the surgical clamp on the aorta and the point of transection for connecting graft 10 using the surgical stapling system of the present invention, and (3) identifying approximately where the staple line will be located on the aorta relative to the point of transection so that the surgeon can be sure that the staples will penetrate healthy aortic tissue.

Sizer 900 includes a shaft 902 having a substantially straight elongated portion 904 and a distal end portion 906, which is oriented at an angle relative to elongated portion 904. End portion 906 may form an angle of between about 90° and about 180° with elongated portion 904. In preferred embodiments, end portion 906 forms an angle of between about 105° and about 125° with elongated portion 904, with an angle of about 115° being most preferred.

A handle 908 is provided at the proximal end of shaft 902, and a measuring bulb 910 is provided at the distal end of the shaft. Measuring bulb 910 has a cylindrical central portion 912 with a generally frusto-conical portion 914 formed on the distal end thereof and another generally frusto-conical portion 916 formed on the proximal end thereof adjacent shaft 902. The frusto-conical shape of portions 914 and 916 facilitate the insertion and removal of sizer 900 through a surgical opening, as well as the insertion of sizer 900 into a transected aorta.

As shown in FIG. 26, bulb 910 has a diameter D at central portion 912, and a length L from the proximal end of central portion 912 to the distal tip 918 of the bulb. The diameter D is used to select a graft 10 of an appropriate size for attachment to the aorta. Thus, in a typical arrangement, a plurality of sizers 900 will be available, each with a bulb 910 having a different diameter D. Typically, bulbs 910 are provided having nominal diameters of approximately 16 mm, 18 mm, and 20 mm so as to accommodate the different sizes of aortas a surgeon may ordinarily encounter. If the bulb 910 of a sizer 900 fits too loosely within the transected end of the aorta, the selected sizer is too small, and a sizer having a larger diameter D should be tried. On the other hand, if the bulb 910 of a sizer 900 does not fit into the transected end of the aorta, the selected sizer is too large, and a sizer having a smaller diameter D should be tried. The proper size is indicated when the bulb 910 fits easily within the transected aorta without excess play.

The length L dimension of bulb 910 is used to determine whether there is an adequate amount of transected aorta available between the surgical clamp on the aorta and the point of transection to perform a stapling procedure. Thus, if the bulb 910 of a sizer 900 can be inserted into the transected aorta so that the entirety of central portion 912 lies within the aorta, the length of aorta available will be sufficient to perform a stapling procedure. However, if a length of central portion 912 remains exposed when bulb 910 has been inserted fully within the transected aorta (i.e., until the surgical clamp prevents further insertion of the bulb), there will not be a sufficient length of aorta available to perform the stapling procedure. In such event, the surgical clamp may be moved farther away from the point of transection to make more of the aorta available. If that is not possible, a conventional graft may be attached to the aorta using a conventional suturing technique. Since the length of the aorta available for a stapling procedure is independent of the diameter of the aorta, the length L is the same for each of bulbs 910, regardless of their diameters.

Bulb 910 is provided with a circumferential recess 920 in central portion 912. Recess 920 is located in the length direction of the bulb so as to indicate the position at which the circumferential line of staples will be deployed. Hence, a surgeon may position bulb 910 of sizer 900 adjacent the aorta prior to transecting same to ensure that the staples will be deployed in healthy aortic tissue relative to the point of transection.

Operation

The use of the surgical stapling system of the present invention to attach a graft to a transected aorta will now be described with reference to FIGS. 27-38. The surgical stapling system may be provided in the form of one or more kits—a first kit consisting of a series of sizers 900 having different diameters; a second kit consisting of a stapling instrument 500 and a tourniquet 400; and a third kit consisting of a graft 10, a loading unit 100, and a wand 300. Each of the kits may include ancillary tools and materials that may be needed to perform a stapling procedure. In the third kit, the graft 10 may be preloaded onto the loading unit 100, which, in turn, may be assembled to the distal end of the wand 300. The size of the graft and the loading unit may differ from kit to kit depending upon the size of the aorta to be repaired. The various components may be separated into multiple kits having the components noted above based on different levels of clean room requirements, which must be adhered to during manufacture, and packaging. Each of the components may be designed to be disposable after their use to perform a single surgical procedure.

Figure 33:
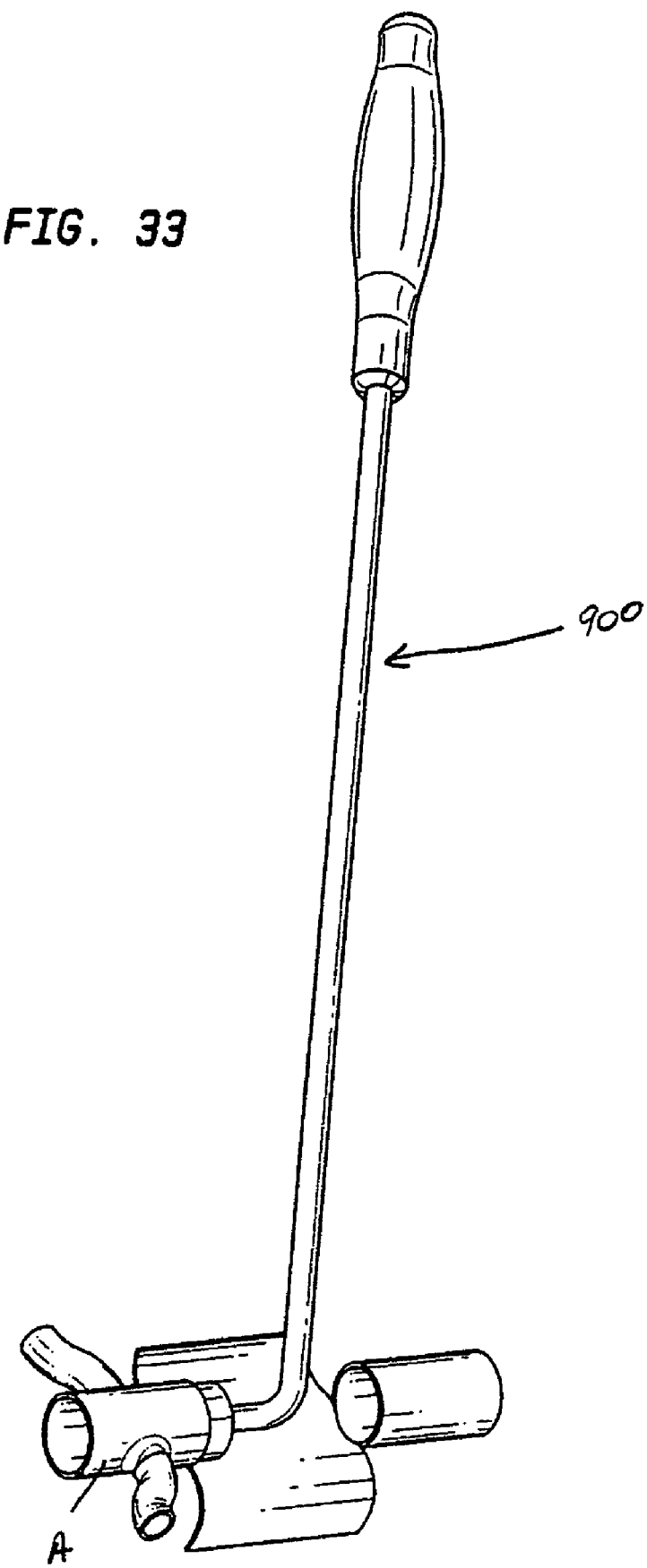
FIG. 33 is a highly schematic perspective view showing the use of a sizer to measure the transected aorta.

As a first step of the procedure, the surgeon may position a sizer 900 adjacent an aorta A to be repaired so as to determine, based on the anticipated point of transection, whether there will be healthy aortic tissue at the projected circumferential stapling line indicated by the circumferential recess 920 in the sizer. The surgeon may then clamp the aorta and form a transection as shown in FIG. 32. As shown in FIG. 33, sizer 900 of an appropriate diameter is then inserted into the transected aorta to determine the approximate diameter of the aorta as well as whether a sufficient length of transected aorta is available between the transection and the clamp to perform a stapling procedure.

Figure 34:
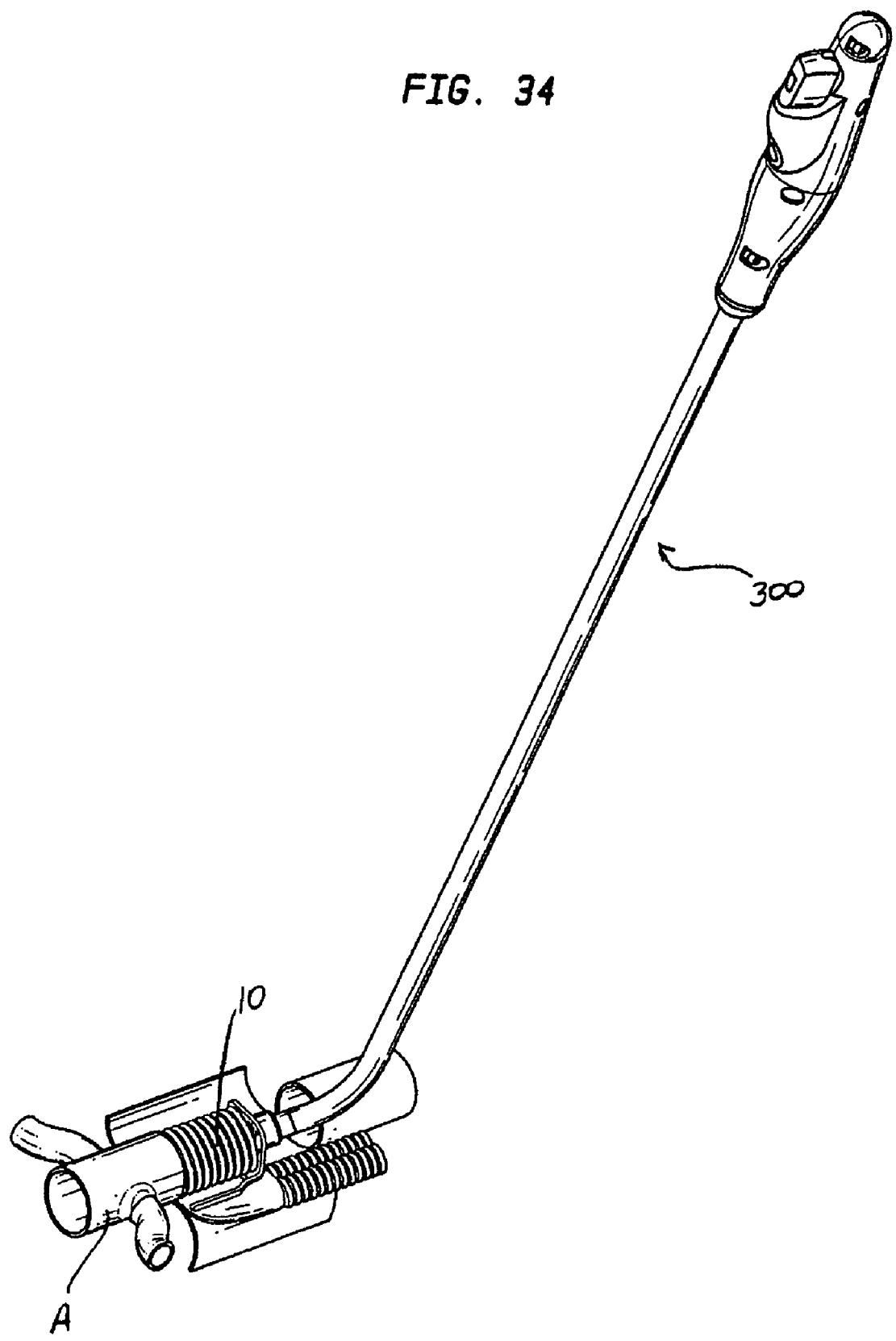
FIG. 34 is a highly schematic perspective view showing the use of a wand to position a loading unit and graft in the transected aorta.
Figure 35:
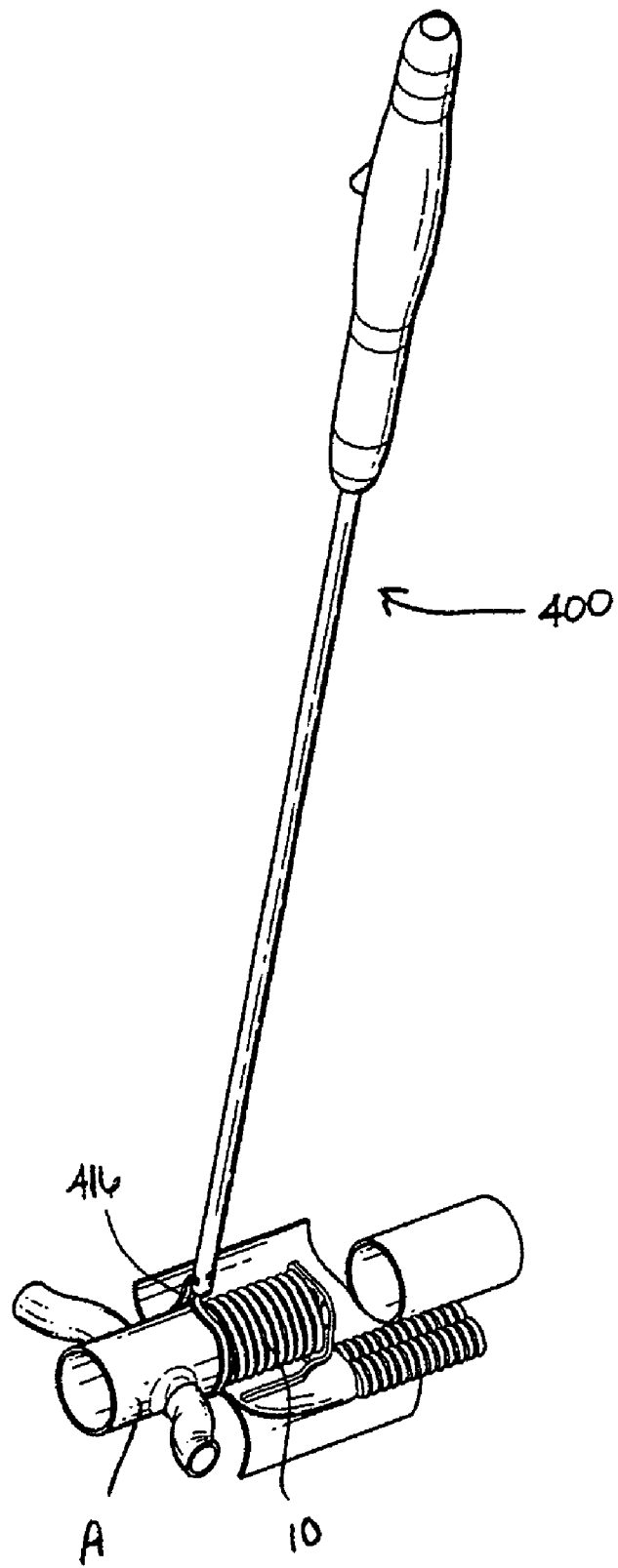
FIG. 35 is a highly schematic perspective view showing the use of a tourniquet to hold the loading unit and graft in place in the aorta.
Figure 36:
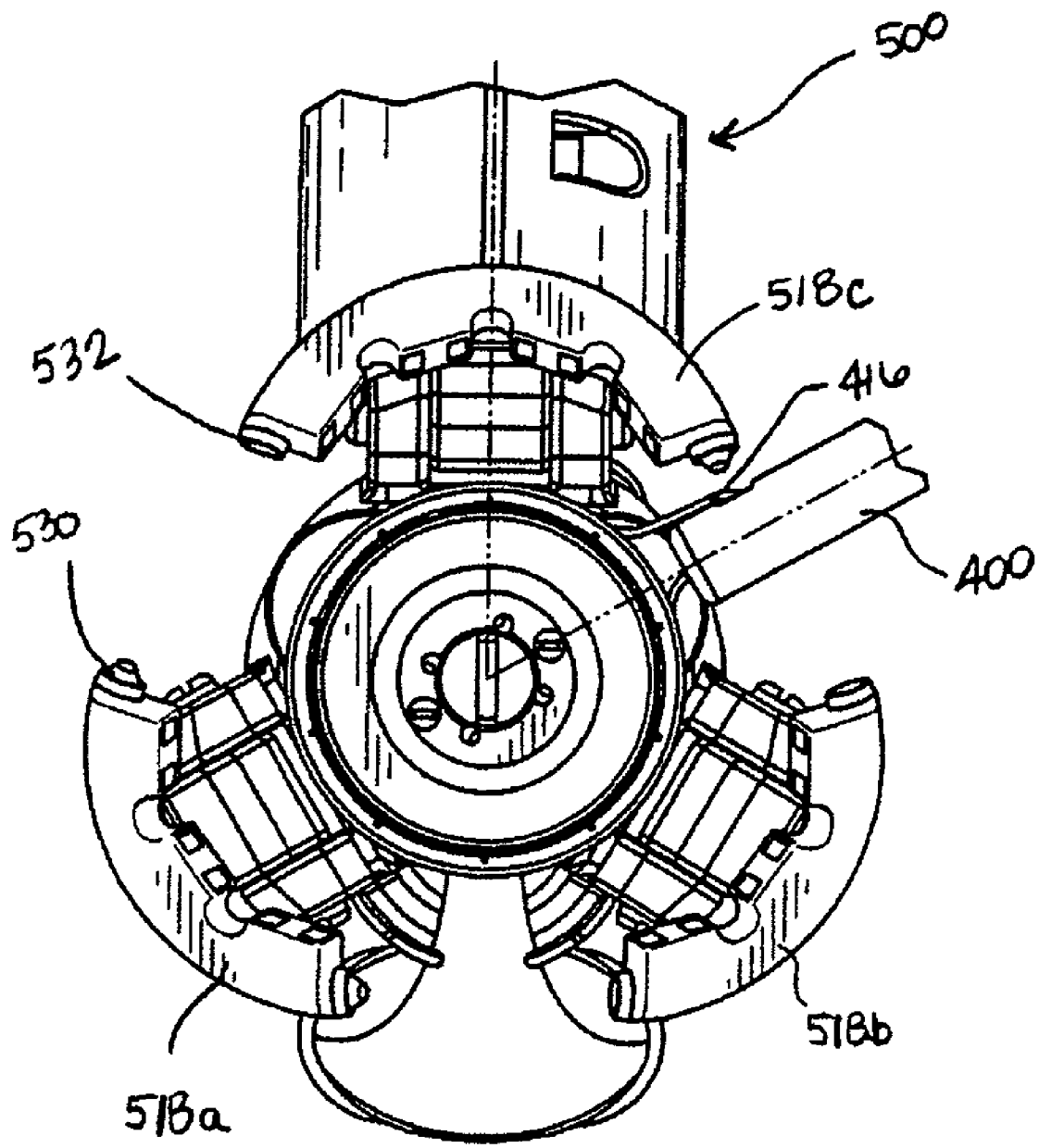
FIG. 36 is an end view showing the positioning of the stapling instrument relative to the tourniquet.

Once the approximate size of the aorta has been determined, and assuming the availability of a sufficient length of transected aorta, the surgeon uses wand 300 to insert a loading unit 100 and its associated graft 10 of the proper diameter into the transected aorta. Referring to FIG. 34, graft 10 is inserted until the cuff 18 of the graft is positioned entirely within the aorta. At this point, tourniquet 400 is used to deploy band 416 around the aorta and the underlying graft 10 and loading unit 100. Tourniquet 400 may be positioned so that the shaft 402 thereof is oriented at either the two o'clock or ten o'clock position, as can be seen in FIG. 36, so that the tourniquet does not interfere with either the assembly of instrument 500 to loading unit 100 or the closing of the anvils 518 of the instrument. As shown in FIG. 35, tourniquet 400 is used to deploy band 416 so that the band is positioned around the aorta in a region adjacent the point of transection. Tightening band 416 around the aorta holds the aorta and graft 10 in fixed overlapping relationship around loading unit 100.

Once band 416 has been placed around the aorta and tightened, wand 300 may be disconnected from loading unit 100. This may be accomplished by first pulling guidewire tubing 346 from the proximal end of handle 330 and off of guidewire 250, and then depressing button 356 on handle 330 to place locking mechanism 350 in the unlocked condition. As a result, wand 300 may be pulled proximally along guidewire 250, whereupon finger 320 will be drawn out from shaft 180 of the loading unit 100. Wand 300 may then be removed entirely from guidewire 250. Alternatively, wand 300 may be removed from guidewire 250 with guidewire tubing 356 attached thereto.

Figure 37:
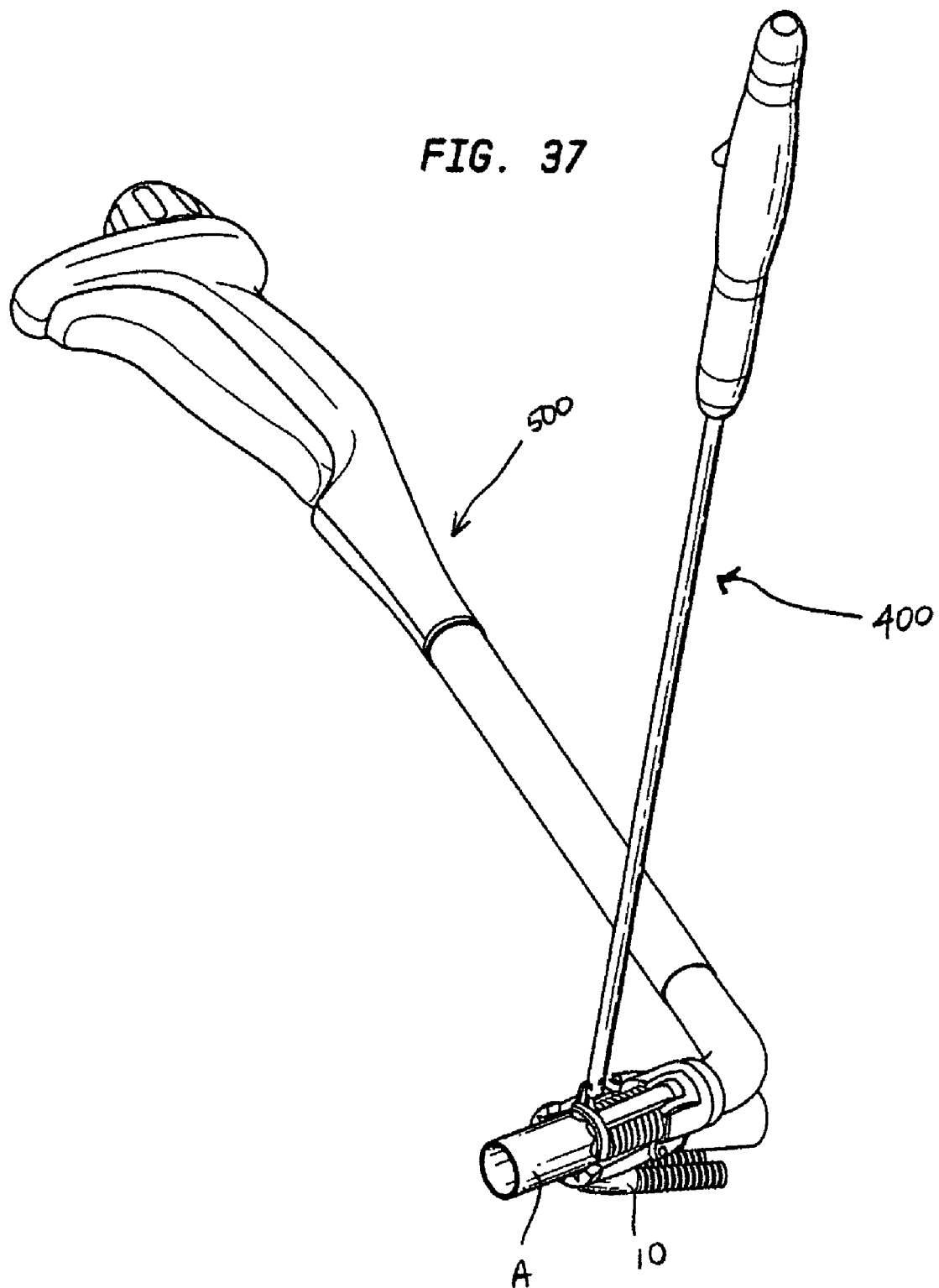
FIG. 37 is a highly schematic perspective view showing the use of a stapling instrument to staple the graft to the aorta.

As the next step, the surgeon may assemble instrument 500 to loading unit 100 as shown in FIG. 37. With anvils 518 in the opened condition (by appropriate rotation of knob 610), guidewire 250 may be inserted into the axial bore 599 in shaft 576, through guidewire tube 709 and out the proximal end of instrument 500. Instrument 500 may then be slid along guidewire 250 until the distal end of shaft 576 is inserted into shaft 180 of loading unit 100. As instrument 500 is advanced, the prongs 596 projecting radially outward from shaft 576 will encounter the cutouts 185 formed on the opposite sides of shaft 180. As they are received in cutouts 185, prongs 596 will be biased radially outward and snap into place, thereby creating an audible click to assure that instrument 500 is fully assembled to loading unit 100. As a further assurance of complete assembly, guidewire 250 may be formed with a colored band or other marker, which will be visible outside of handle 512 when instrument 500 has been assembled fully to loading unit 100.

Figure 18:
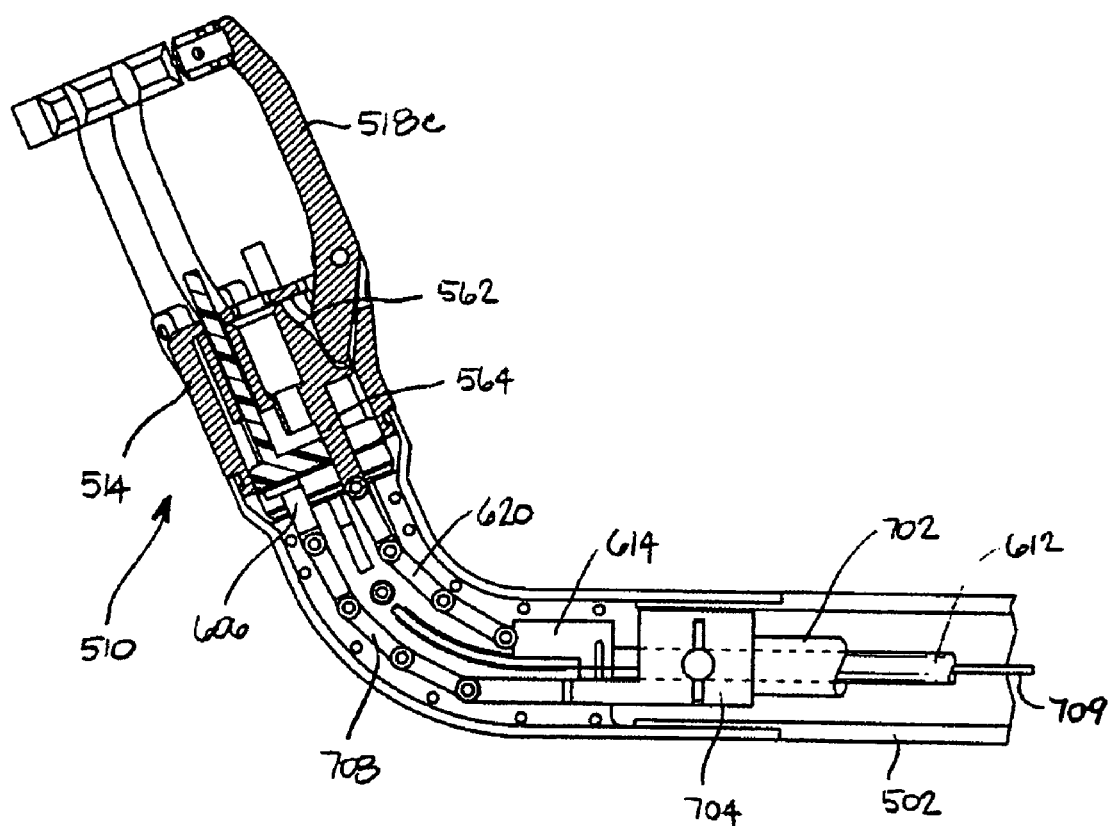
FIG. 18 is a longitudinal cross-sectional view of the head of the surgical stapling instrument with the anvils in the closed condition.

Anvil assembly 510 may then be placed in the closed condition shown in FIG. 18 by rotating adjustment knob 610. As adjustment knob 610 is rotated, shaft 642 is rotated in the same direction through the engagement of teeth 658 on the knob with recesses 660 on the shaft. The rotation of shaft 642 causes coupling element 628 to move distally as a result of its threaded engagement with shaft 642. The distal movement of coupling element 628 pushes tube 612 distally, and with it link coupler 614 and links 620. As a result of this distal movement, cam element 550 is also moved in the distal direction. The relative movement of cam element 550 into anvil bracket 514 causes the guide pins 522 on anvils 518 to move outwardly along tapered cam surface 562, resulting in the inward movement of brackets 524 at the distal ends of the anvils. Knob 610 is rotated until anvil assembly 510 is in the fully closed condition with brackets 524 defining a complete circle.

With anvil assembly 510 fully closed, trigger mechanism 670 may be actuated to deploy staples 150. As a first step, one of buttons 726 and 730 is depressed to release safety 710 from trigger 672. Trigger 672 may then be squeezed toward handle 512, whereupon engagement surface 700 within trigger 672 pushes against the apex 698 of linkage assembly 680. This movement causes the end 692 of linkage assembly 680 to move axially in the distal direction, thereby moving coupling element 694, tube 702, coupling link 704 and links 708 distally. The distal movement of links 708 drives the fingers 604 of pusher 600 out through apertures 548 of anvil hub 514, through apertures 105 in the cap 104 of loading unit 100, and against the annular flange 174 at the proximal end of actuator 170.

The continued distal movement of pusher 600 drives actuator 170 distally, overcoming the spring force exerted by retaining clip 184 to hold actuator 170 in a fixed axial position relative to shaft 180. The distal movement of actuator 170 causes the tapered surface 178 on each of the fingers 176 of the actuator to engage the cam surface 146 of a corresponding staple pusher 130. As a result of the interaction of tapered surfaces 178 with staple pushers 130, the staple pushers are driven radially outward, pushing staples 150 ahead of them. Staples 150 move radially outward until the free ends of the legs 154 and 156 of the staples contact the staple returns 528 on anvils 518. Staple returns 528 cause staple legs 154 and 156 to turn inwardly and back toward the crossmember 152 of the staple so as to form a "B" configuration, shown in FIG. 31, when the stapling operation has been completed. Staples 150 are deployed so that one leg 156 of each staple pierces graft 10 and aorta A is then turned back through the aorta. The other leg 158 of each staple pierces aorta A directly and is then turned back through the aorta, forming a loop around the free edge of graft 10 to hold it tightly to the aorta. The tips of the staple legs may or may not pierce graft 10 from the opposite side.

Figure 29:
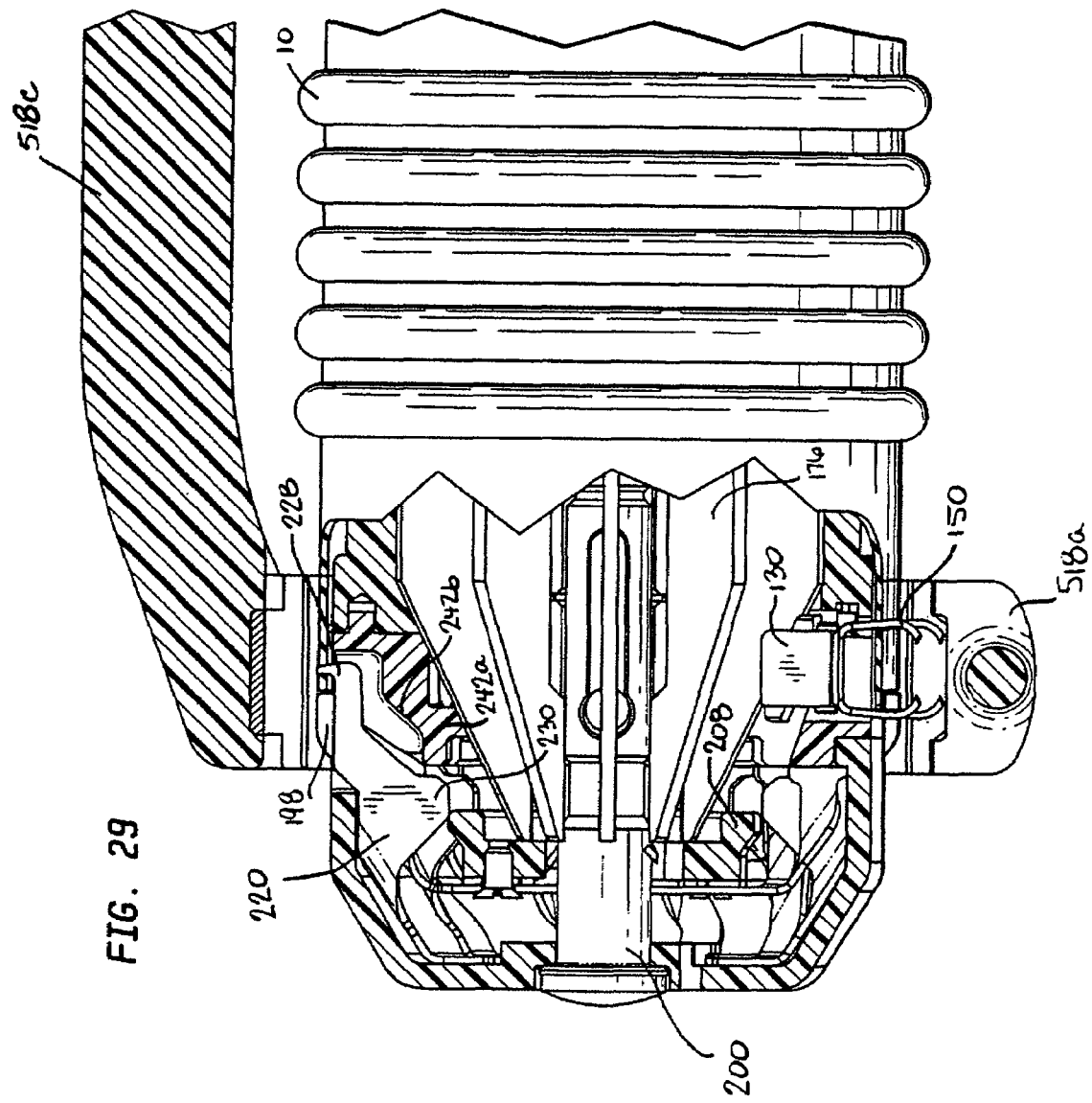
FIG. 29 is the same view as FIG. 26, but showing the staples in a more advanced state of deployment.
Figure 30:
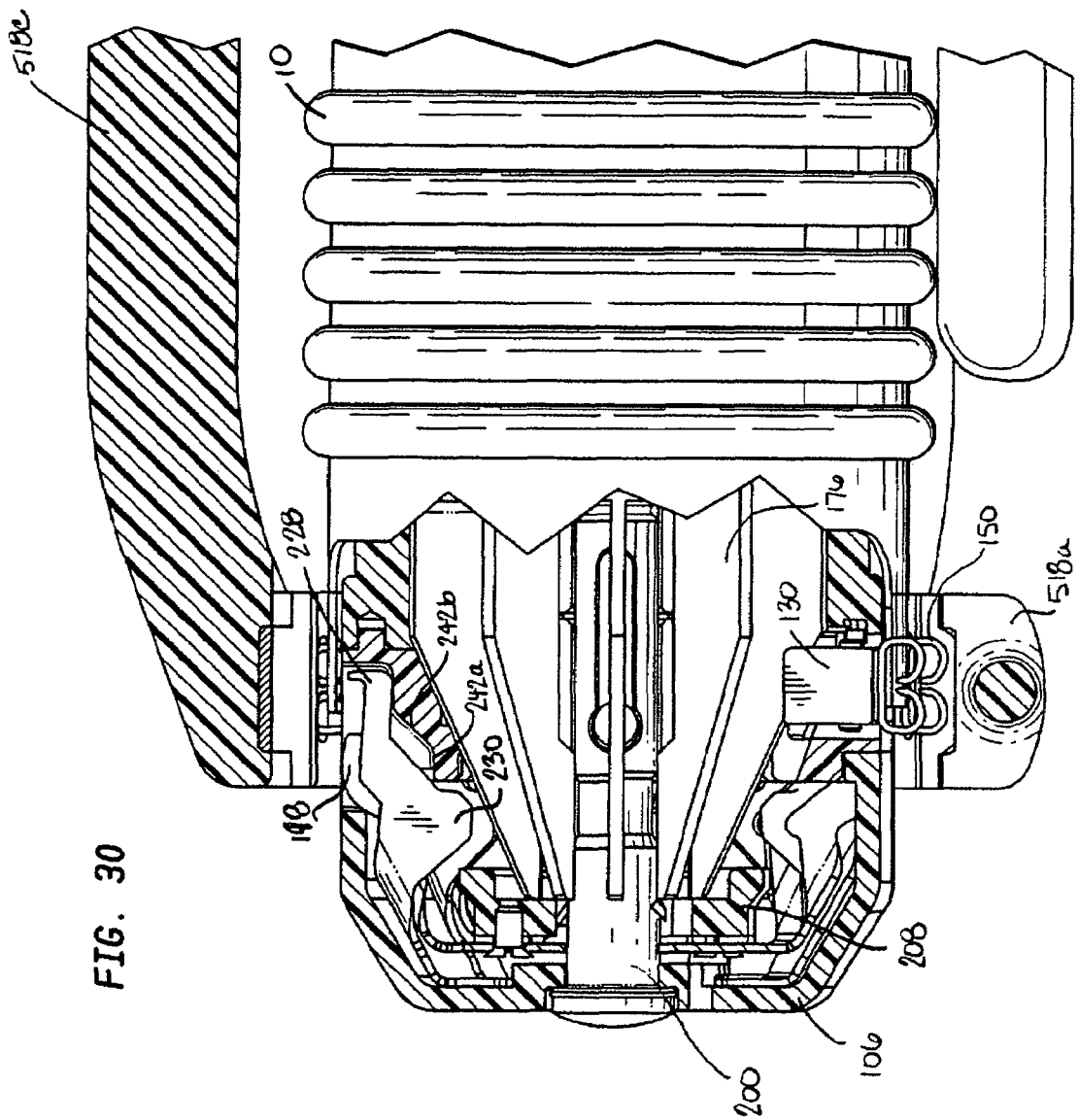
FIG. 30 is the same view as FIG. 26, but showing the staples fully deployed.

As the fingers 176 of actuator 170 progress distally, the tips of the fingers will engage the proximal surface of cam ring 208, driving the cam ring and retainer 190 connected thereto toward cap 106, as shown in FIG. 29. This movement will push the tips 198 of the fingers 192 of retainer 190 off of the cuff 18 of graft 10. At the same time, cam ring 208 will be moved distally relative to the cams 230 on the fingers 222 of retainer 220 until cam surface 230a is riding on the outer periphery of the cam ring. Continued distal movement of cam ring 208 will cause fingers 222 to move inwardly of loading unit 100 as a result of the inward biasing force exerted by the fingers, thereby releasing the tips 228 of the fingers from graft 10. Hence, the actuation of trigger mechanism 270 to deploy staples 150 simultaneously releases retainers 190 and 220 from the cuff 18 of the graft.

Following the deployment of staples 150, trigger 672 may be released, whereupon the biasing force of spring 698 will cause the trigger to return to its rest position. At the same time, the apex 698 of linkage assembly 680 will move away from handle 512, with the end 692 of the linkage assembly moving in the proximal direction. This proximal movement will cause coupling element 694, tube 702, coupling link 704, and links 708 to also move proximally, resulting in the withdrawal of the fingers 604 of pusher 600 from loading unit 100. Anvil assembly 510 may then be placed in the open condition by rotating knob 610 in the opposite direction, and instrument 500, with loading unit 100 connected thereto, may be removed from graft 10, leaving the graft attached to the aorta by a circumferential line of staples 999, as can be seen in FIG. 38. Subsequently, the legs 14 and 16 of graft 10 may be sutured in a conventional fashion to the patient's iliac arteries. The procedure is completed by closing side port 20 of graft 10 through the use of suture 22 to form a purse string tie, through a conventional suturing operation, or by a surgical stapling technique, and, where appropriate, by removing any excess portion of side port 20 from the graft.

The various components of the present invention may be used in a conventional open body surgical procedure. The instruments may also be used to perform a stapling operation laparascopically by providing the instruments with appropriate seals to prevent the escape of air used to expand the body cavity during a laparoscopic procedure.

In addition to the several embodiments described above, the various components of the stapling system of the present invention may be varied in many ways. For example, it will be appreciated that, where appropriate, any of the features described in connection with a particular embodiment hereof may be incorporated in any other embodiment described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A surgical stapler system for joining a graft and a tubular structure by a surgical stapling procedure, comprising:
   a detachable loading unit including a circumferential line of staples adapted to hold said graft in position in a body and deploy said staples through said graft and an overlapping end of said tubular structure;
   a wand for introducing said loading unit and said graft into said body, positioning said loading unit and said graft within said tubular structure, and holding said loading unit and said graft in place during at least a portion of said procedure;
   a guidewire joined with an end of said loading unit and extending from an opposite end of said loading unit, said guidewire being configured to extend out of said graft and said body; and
   a stapling instrument that is independent from said loading unit in a first position, said first position being exterior to said body while said loading unit is located inside said body, said stapling instrument adapted to be connected to said loading unit via said guidewire thereby positioning said stapling instrument in a second position, said second position being located inside said body, said stapling instrument having a plurality of anvils and a trigger mechanism for firing said staples in said loading unit when said stapling instrument is connected to said loading unit in said second position, wherein upon actuating said trigger mechanism said staples deploy radially outward through said graft and said tubular structure, strike said anvils, and bend inwardly.

2. A surgical stapler system according to claim 1, further comprising:
   one or more sizers for determining diameters of said tubular structure and a transected length of said tubular structure.

3. A surgical stapler system according to claim 1, further comprising:
   a surgical loop having a band formed from a flexible material and having a width greater than its thickness thereby forming an annular loop, said loop adapted to hold said graft and said tubular structure in relative overlapping positions.

4. A surgical stapler system according to claim 1, wherein said loading unit includes retractable fingers for holding temporarily joining said graft with said loading unit.

5. A surgical stapler system according to claim 1, wherein said staples in said loading unit cannot be fired unless said stapling instrument is connected to said loading unit and in said second position.

6. A surgical stapler system according to claim 1, wherein said trigger mechanism in said stapling instrument includes a safety that mechanically prevents actuation of said trigger mechanism and firing of said staples in said loading unit when said safety is in a first position.

7. A surgical stapler system according to claim 1, wherein said anvils in said stapling instrument are positioned on retractable fingers that are configured to be retractably positioned adjacent said overlapping end of said tubular structure when said trigger mechanism is actuated.

8. A surgical stapler system according to claim 1, said stapling instrument further comprises a pusher and said loading unit further comprises staple pushers, wherein said pusher engages said staple pushers when said trigger mechanism is actuated thereby causing said staple pushers to force staples radially outward from said loading unit.

9. A surgical stapler device for joining a graft and a tubular structure, said device comprising:
   a loading unit including a circumferential line of staples adapted to hold said graft in position in a body and deploy said staples through said graft and an overlapping end of said tubular structure;
   a wand for introducing said loading unit and said graft into said body and positioning and holding said loading unit and said graft within said tubular structure;
   a guidewire extending from said loading unit, said guidewire being configured to extend out of said graft and said body; and
   a stapling instrument that is independent from said loading unit in a first position, said first position being exterior to said body while said loading unit is located inside said body, said stapling instrument adapted to be connected to said loading unit via said guidewire thereby positioning said stapling instrument in a second position, said second position being located inside said body, said stapling instrument having a plurality of anvils and a trigger mechanism for firing said staples in said loading unit when said stapling instrument is connected to said loading unit in said second position, wherein upon actuating said trigger mechanism said staples deploy radially outward through said graft and said tubular structure, strike said anvils, and bend inwardly.

10. A surgical stapler device according to claim 9, wherein said loading unit includes retractable fingers for temporarily joining said graft with said loading unit.

11. A surgical stapler device according to claim 9, wherein said staples in said loading unit cannot be fired unless said stapling instrument is connected to said loading unit and in said second position.

12. A surgical stapler device according to claim 9, wherein said trigger mechanism in said stapling instrument includes a safety that mechanically prevents actuation of said trigger mechanism and firing of said staples in said loading unit when said safety is in a first position.

13. A surgical stapler device according to claim 9, wherein said anvils in said stapling instrument are positioned on retractable fingers that are configured to be retractably positioned adjacent said overlapping end of said tubular structure when said trigger mechanism is actuated.

14. A surgical stapler device according to claim 9, said stapling instrument further comprises a pusher and said loading unit further comprises staple pushers, wherein said pusher engages said staple pushers when said trigger mechanism is actuated thereby causing said staple pushers to force staples radially outward from said loading unit.

* * * * *